(12) United States Patent
Fukumoto et al.

(10) Patent No.: US 11,675,418 B2
(45) Date of Patent: Jun. 13, 2023

(54) PROGRAM, INFORMATION PROCESSOR, AND INFORMATION PROCESSING METHOD FOR BLENDING MOTIONS OF A PLURALITY OF ACTORS

(71) Applicant: SONY CORPORATION, Tokyo (JP)

(72) Inventors: Yasutaka Fukumoto, Tokyo (JP); Nobuhiro Saijo, Tokyo (JP); Kazuma Takahashi, Kanagawa (JP); Keita Mochizuki, Chiba (JP)

(73) Assignee: SONY CORPORATION, Tokyo (JP)

( * ) Notice: Subject to any disclaimer, the term of this patent is extended or adjusted under 35 U.S.C. 154(b) by 210 days.

(21) Appl. No.: 17/045,360

(22) PCT Filed: Apr. 15, 2019

(86) PCT No.: PCT/JP2019/016152
§ 371 (c)(1),
(2) Date: Oct. 5, 2020

(87) PCT Pub. No.: WO2019/203190
PCT Pub. Date: Oct. 24, 2019

(65) Prior Publication Data
US 2021/0166479 A1 Jun. 3, 2021

(30) Foreign Application Priority Data

Apr. 17, 2018 (JP) .............................. JP2018-079335

(51) Int. Cl.
*G06F 3/01* (2006.01)
*G06T 7/246* (2017.01)
(Continued)

(52) U.S. Cl.
CPC ............ *G06F 3/011* (2013.01); *A61B 5/1114* (2013.01); *A61B 5/1122* (2013.01);
(Continued)

(58) Field of Classification Search
None
See application file for complete search history.

(56) References Cited

U.S. PATENT DOCUMENTS 6,088,042 A * 7/2000 Handelman ............. G06T 13/40
345/475
8,437,506 B2 * 5/2013 Williams .............. A63F 13/213
348/46

(Continued)

FOREIGN PATENT DOCUMENTS

JP    2003-259214 A    9/2003
JP    2006177749 A     7/2006
(Continued)

OTHER PUBLICATIONS

Uchida et al., Sports program viewing support system using sign language CG, Proceedings of the 16th Forum on Information Technology 2017, Sep. 12-17, 2017, pp. 169-174 (see European Search Report below for concise relevance).
(Continued)

*Primary Examiner* — Hilina K Demeter
(74) *Attorney, Agent, or Firm* — Paratus Law Group, PLLC

(57) ABSTRACT

There is provided a program, an information processor, and an information processing method that make it possible to blend motions of a plurality of actors captured by using a motion capture technique and to reproduce the blended motions in real time in an avatar or the like on a virtual space. The program causes a computer to implement a control function of dynamically controlling a motion of an avatar in a virtual space or a robot on a real space, the control function being configured to: capture motions of a plurality of actors on the real space from respective motion sensors attached to the actors; blend the motions of the plurality of actors on the basis of a predetermined algorithm; and (Continued)

dynamically control the motion of the avatar or the robot on the basis of the blend result to cause the avatar or the robot to make a motion reflecting the motions of the plurality of actors.

15 Claims, 40 Drawing Sheets

(51) Int. Cl.
| | | |
|---|---|---|
| G06F 3/04815 | (2022.01) | |
| G06T 19/00 | (2011.01) | |
| A61B 5/11 | (2006.01) | |
| A61B 5/00 | (2006.01) | |
| A63F 13/428 | (2014.01) | |
| G06T 13/40 | (2011.01) | |
| G01B 21/00 | (2006.01) | |
| A61B 5/0205 | (2006.01) | |

(52) U.S. Cl.
CPC ............ *A61B 5/1126* (2013.01); *A61B 5/744* (2013.01); *A63F 13/428* (2014.09); *G01B 21/00* (2013.01); *G06F 3/04815* (2013.01); *G06T 7/251* (2017.01); *G06T 13/40* (2013.01); *G06T 19/003* (2013.01); *A61B 5/0205* (2013.01); *A61B 5/7267* (2013.01); *A61B 2562/0219* (2013.01)

(56) References Cited

U.S. PATENT DOCUMENTS

| | | | | |
|---|---|---|---|---|
| 9,381,426 | B1* | 7/2016 | Hughes | ............... H04L 67/06 |
| 2002/0103610 | A1* | 8/2002 | Bachmann | ............ G01C 17/38 |
| | | | | 702/94 |
| 2011/0007079 | A1* | 1/2011 | Perez | ...................... A63F 13/56 |
| | | | | 345/473 |
| 2015/0029097 | A1* | 1/2015 | Craig | ..................... G06F 18/21 |
| | | | | 345/156 |
| 2015/0030305 | A1* | 1/2015 | Moon | ................... A63F 13/211 |
| | | | | 386/230 |
| 2015/0192413 | A1* | 7/2015 | Bellusci | ................ G01C 21/16 |
| | | | | 702/152 |
| 2016/0241768 | A1* | 8/2016 | Lokshin | ................. H04N 23/66 |
| 2017/0189752 | A1 | 7/2017 | Mohrman et al. | |
| 2018/0033190 | A1 | 2/2018 | Ma et al. | |
| 2020/0060602 | A1 | 2/2020 | Wagner et al. | |

FOREIGN PATENT DOCUMENTS

| | | |
|---|---|---|
| JP | 2007-072194 A | 3/2007 |
| JP | 2013125024 A | 6/2013 |
| JP | 2015-184689 A | 10/2015 |
| JP | 2017511906 A | 4/2017 |
| WO | WO-2017043181 A1 | 3/2017 |
| WO | WO 2018/051540 A1 | 3/2018 |

OTHER PUBLICATIONS

Oct. 8, 2021, European Search Report for related EP Application No. 19788605.4.

* cited by examiner

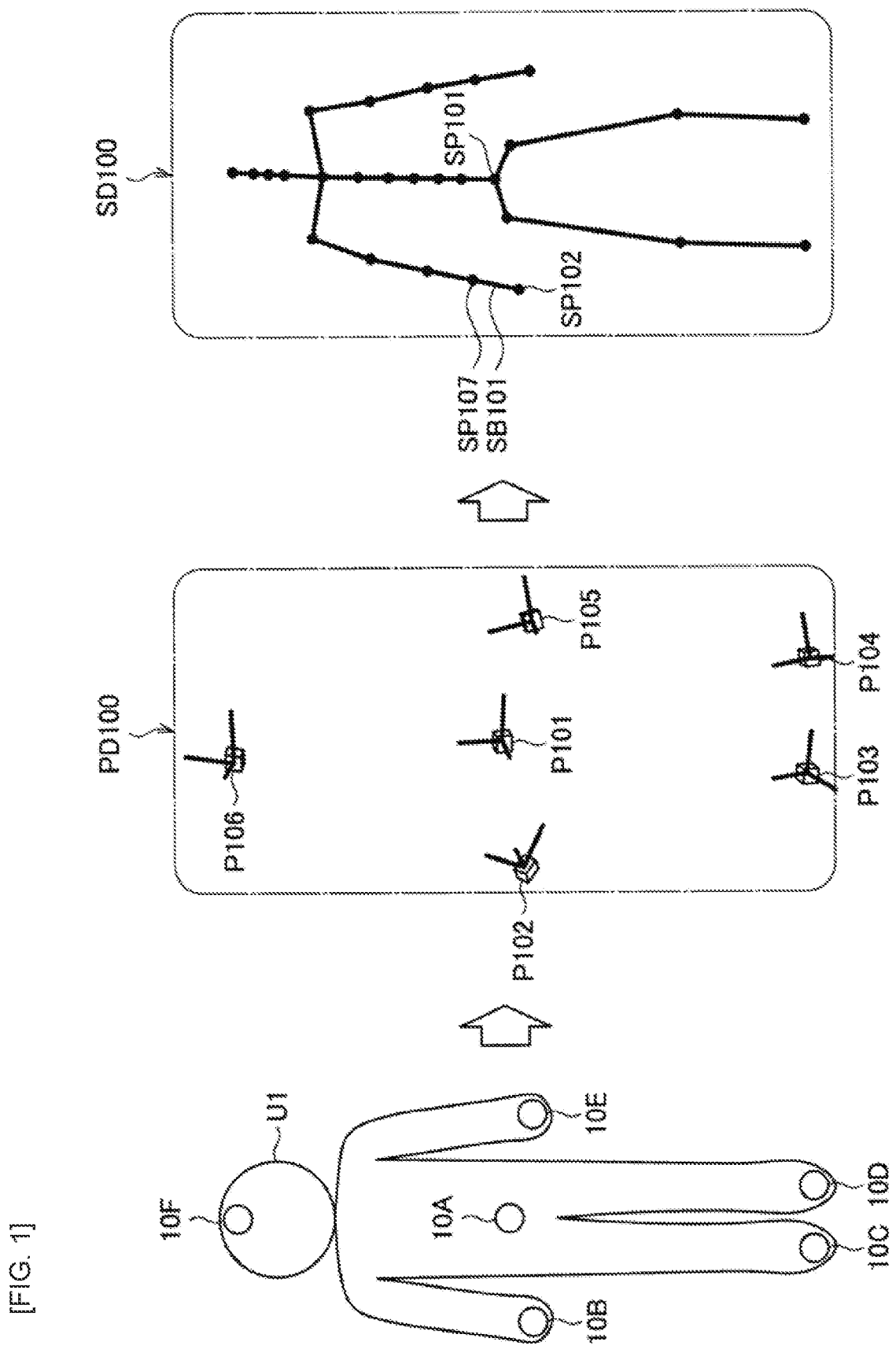

[ FIG. 2 ]
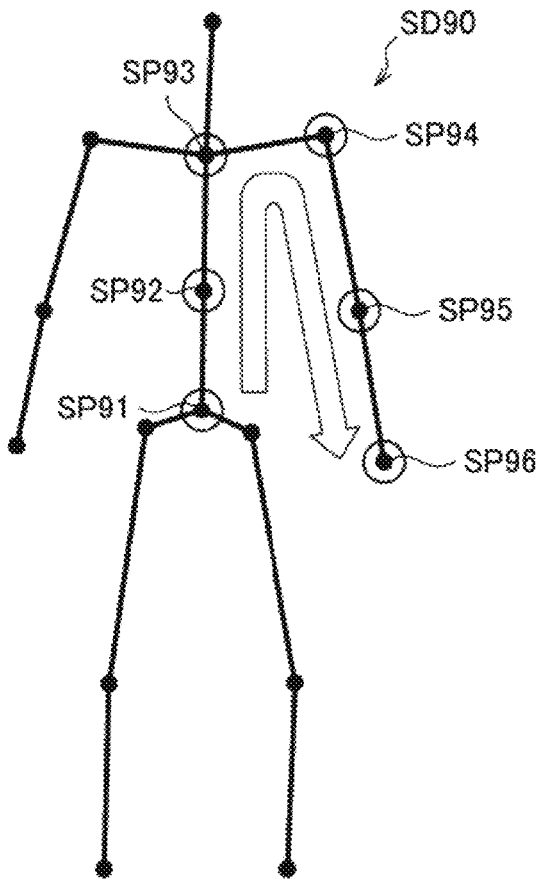
[ FIG. 3 ]
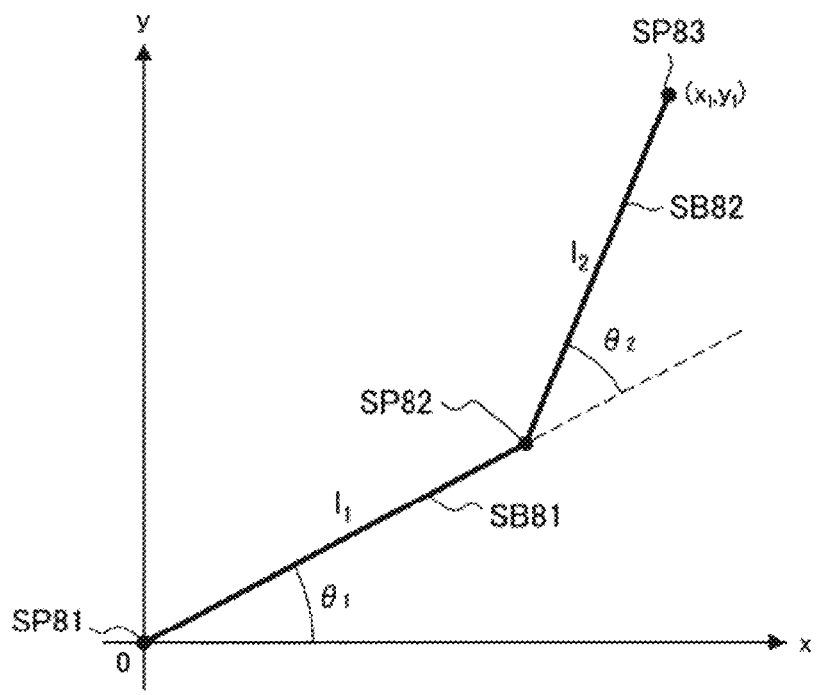

[ FIG. 4 ]
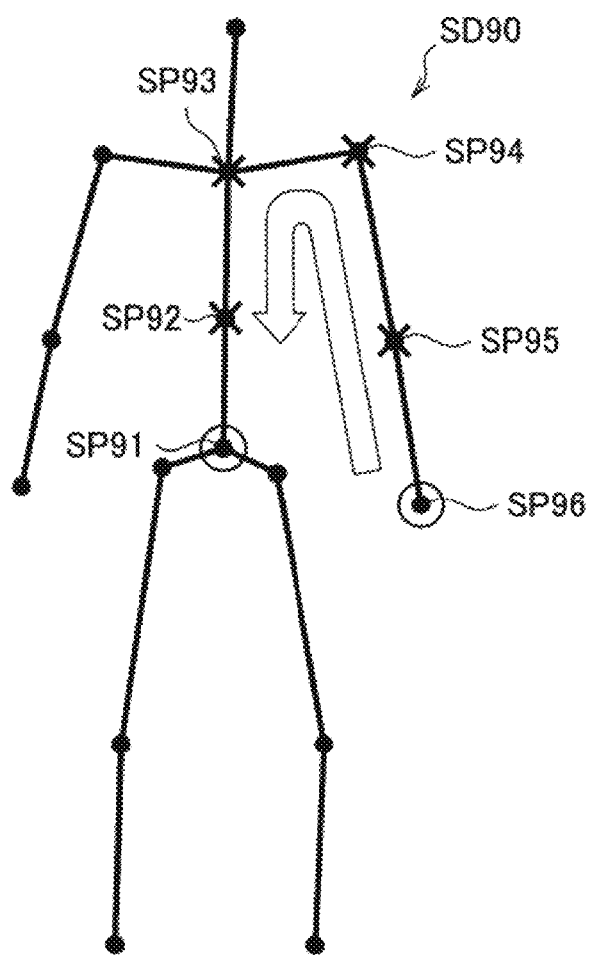

[FIG. 5]
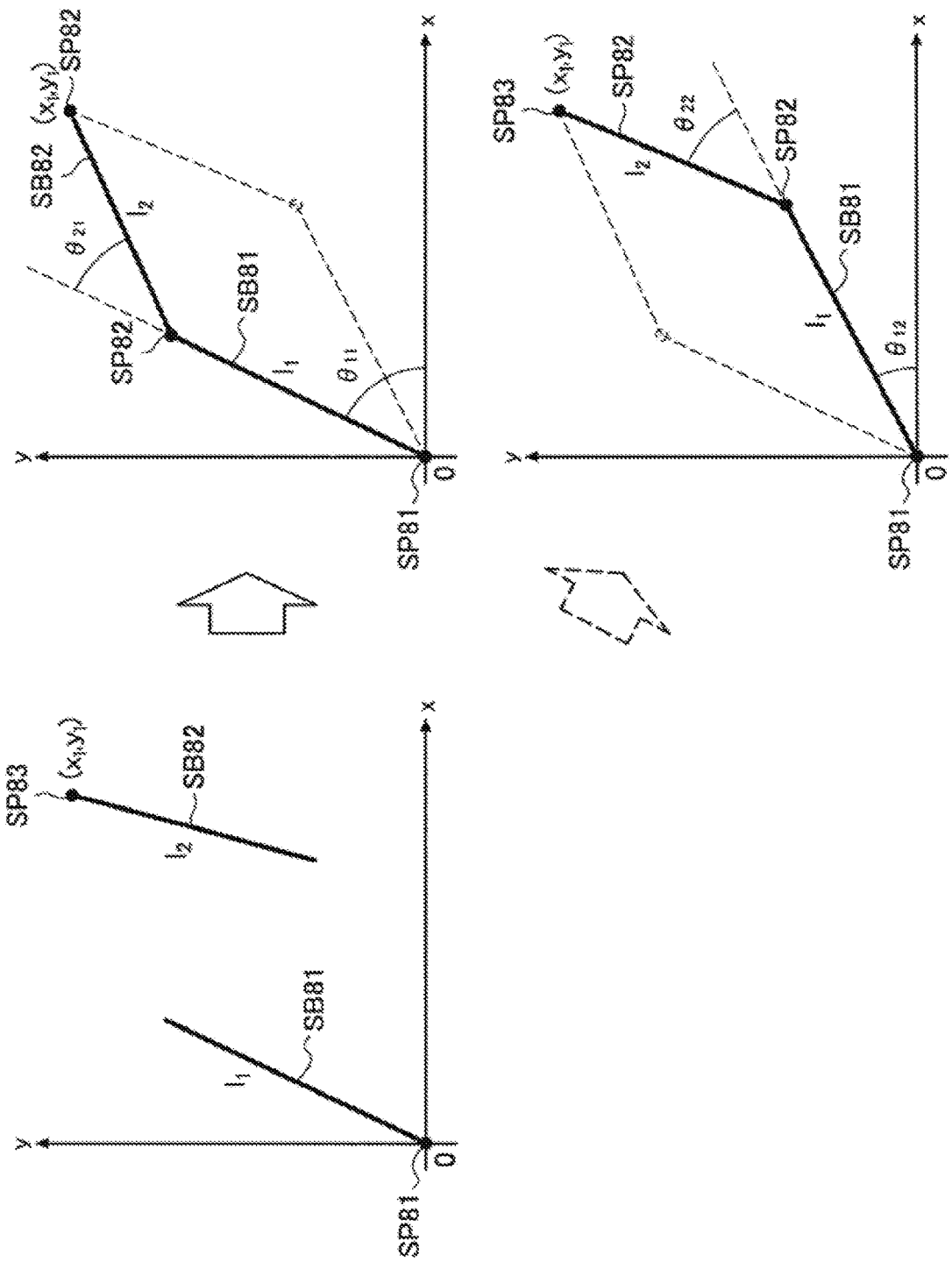

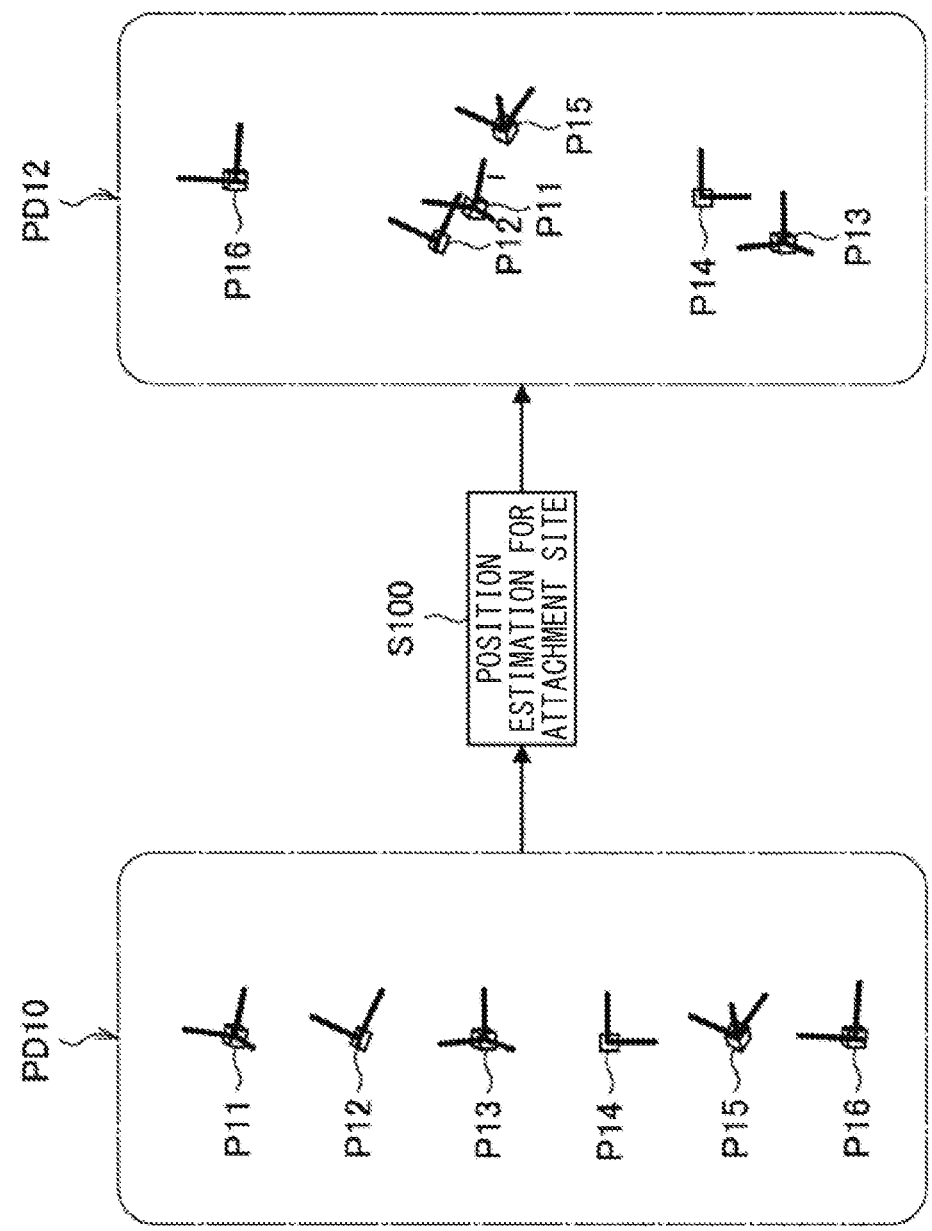

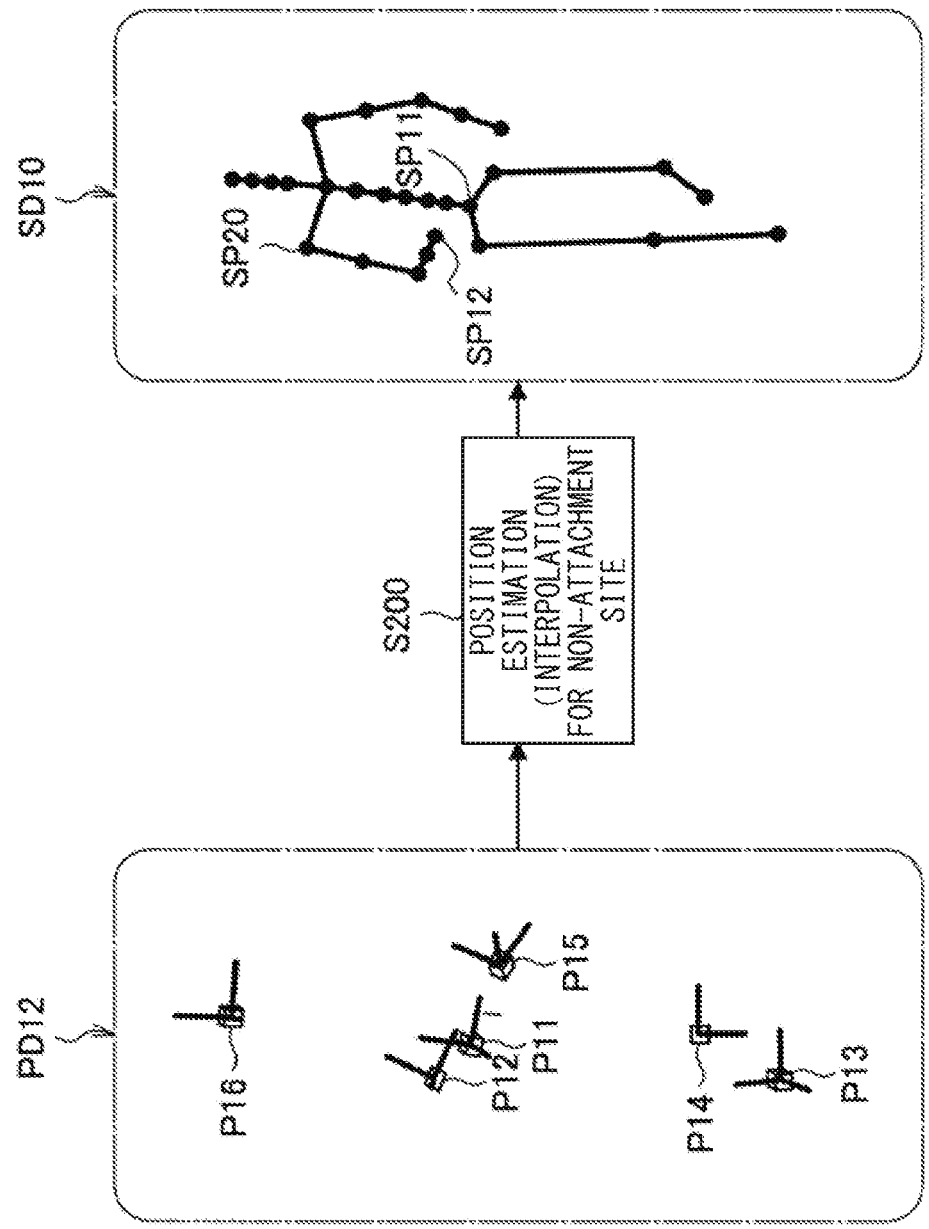

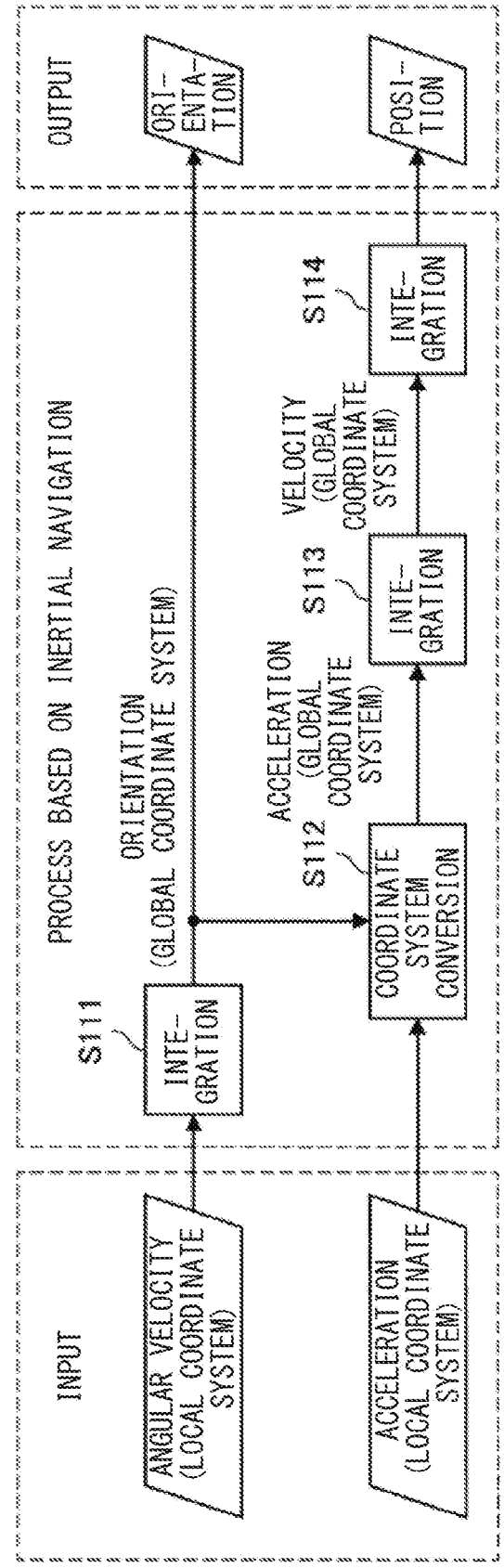
[FIG. 8]

[ FIG. 9 ]
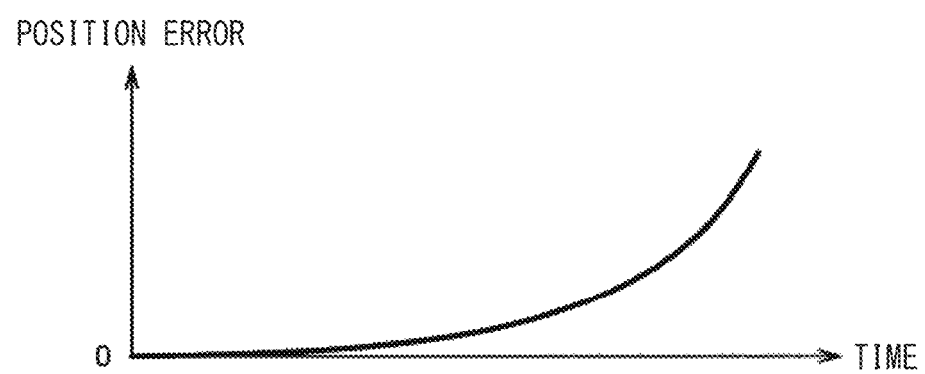

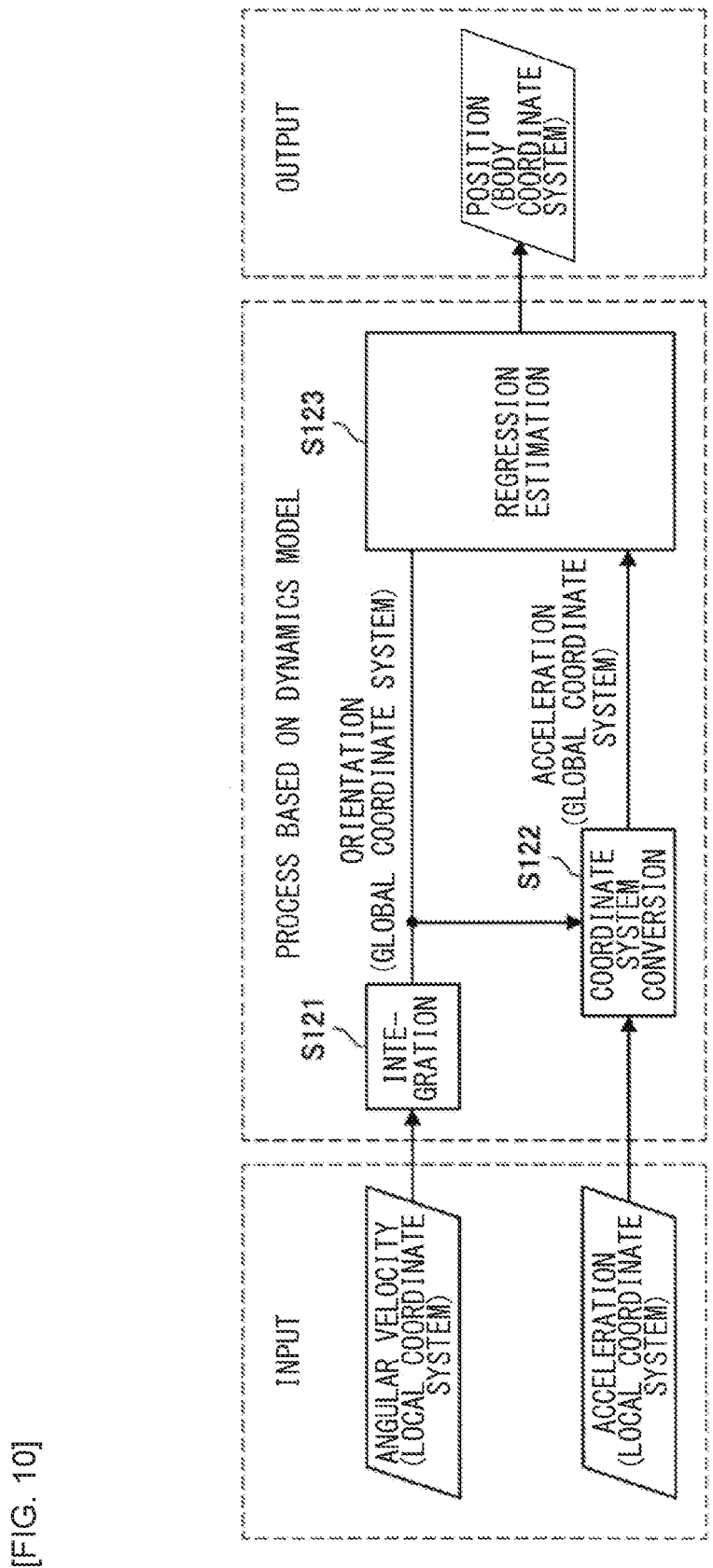
[FIG. 10]

[ FIG. 11 ]
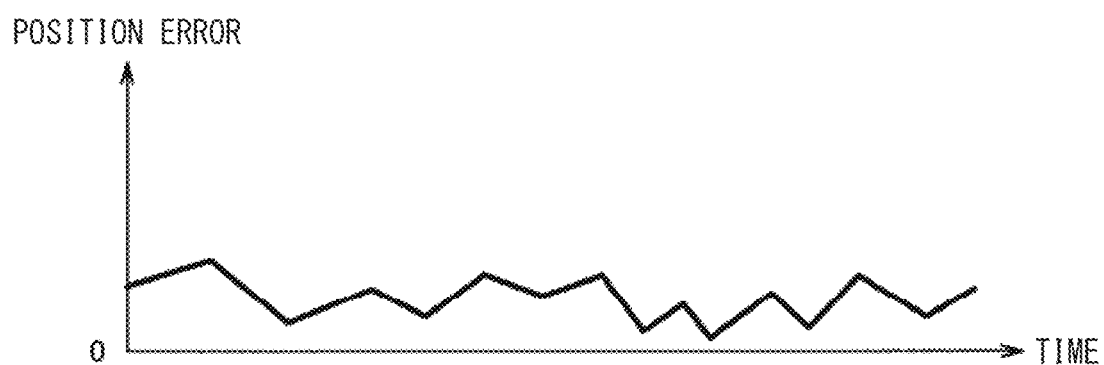

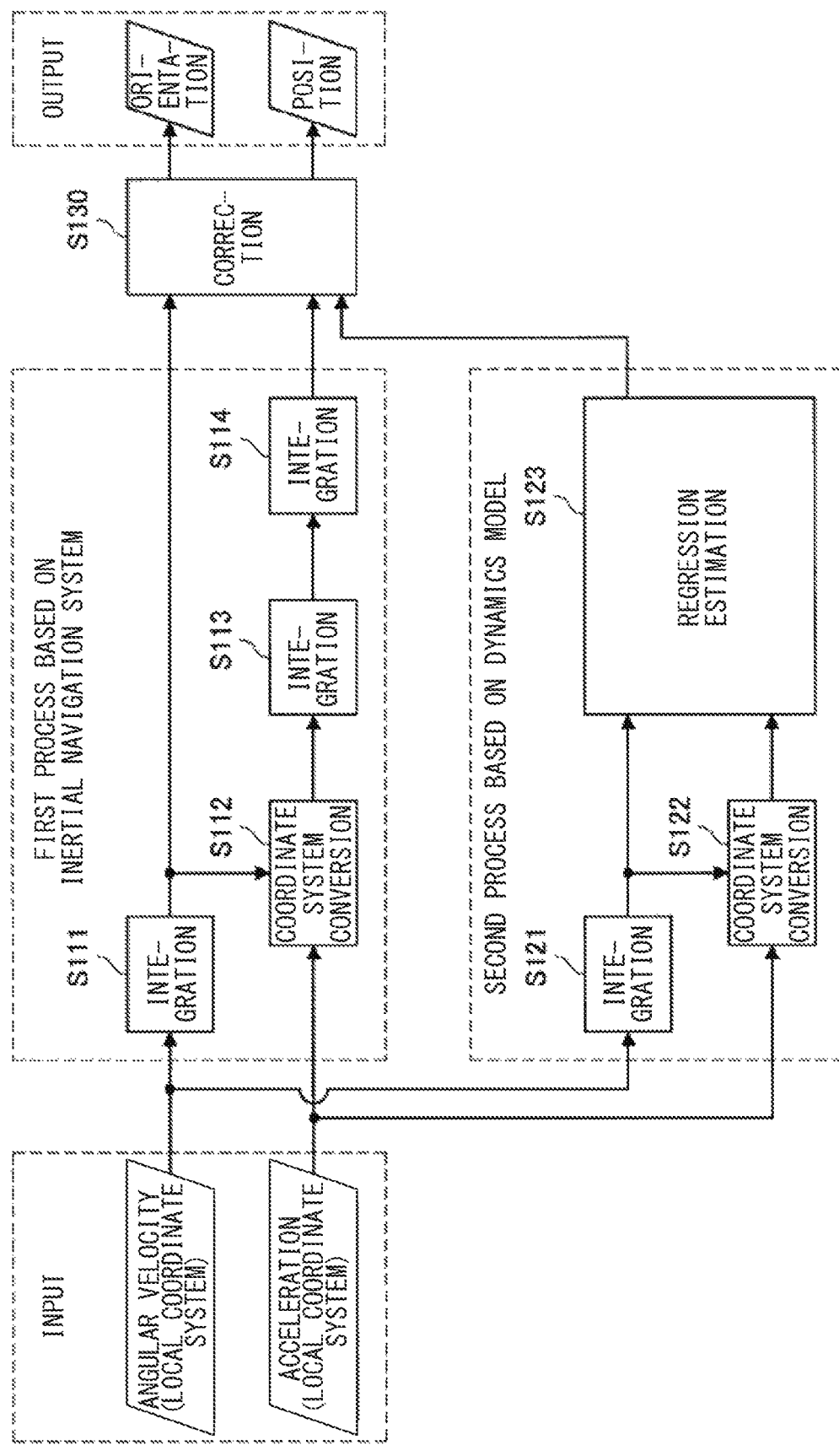
[FIG. 12]

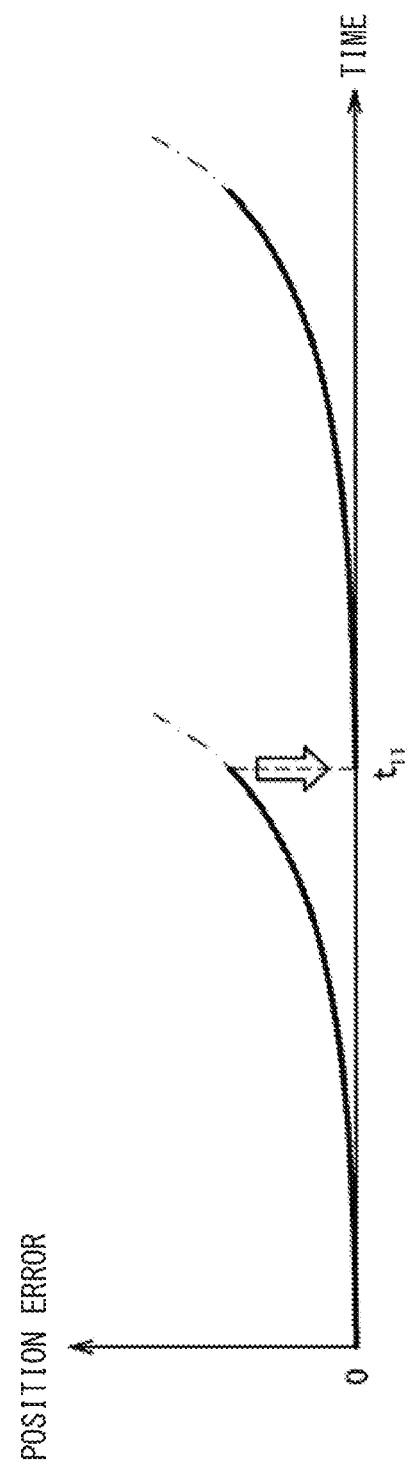
[FIG. 13]

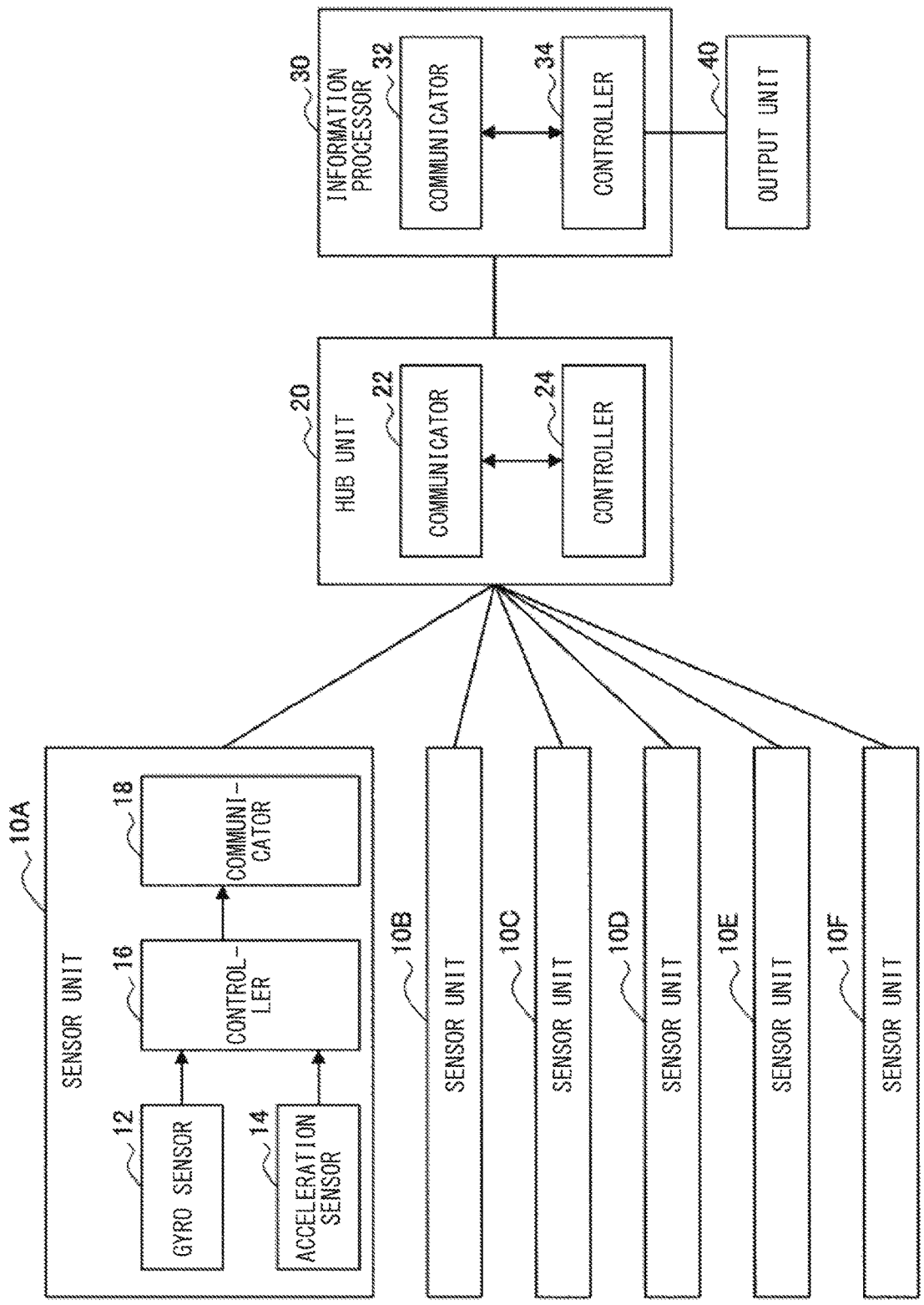

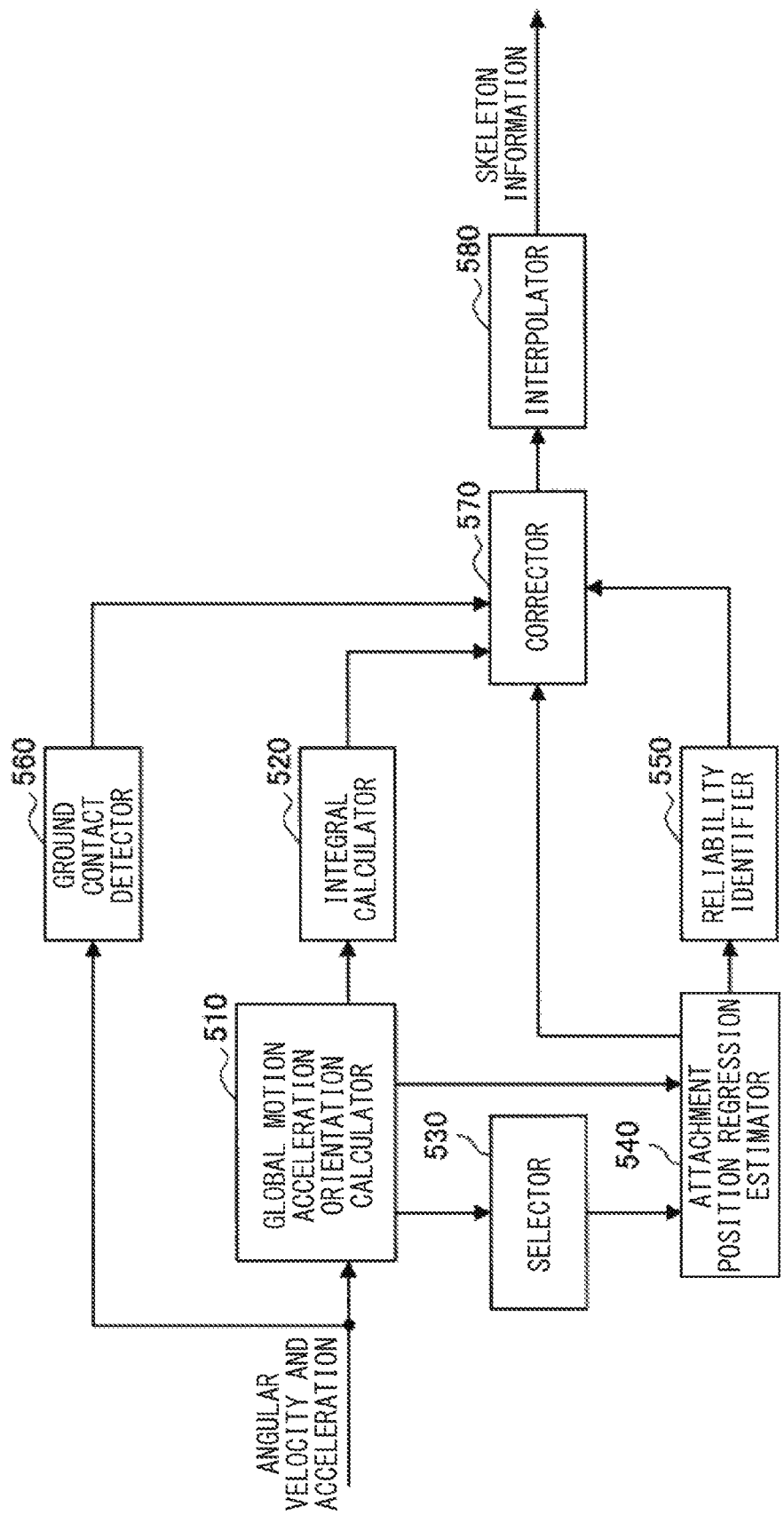
[FIG. 15]

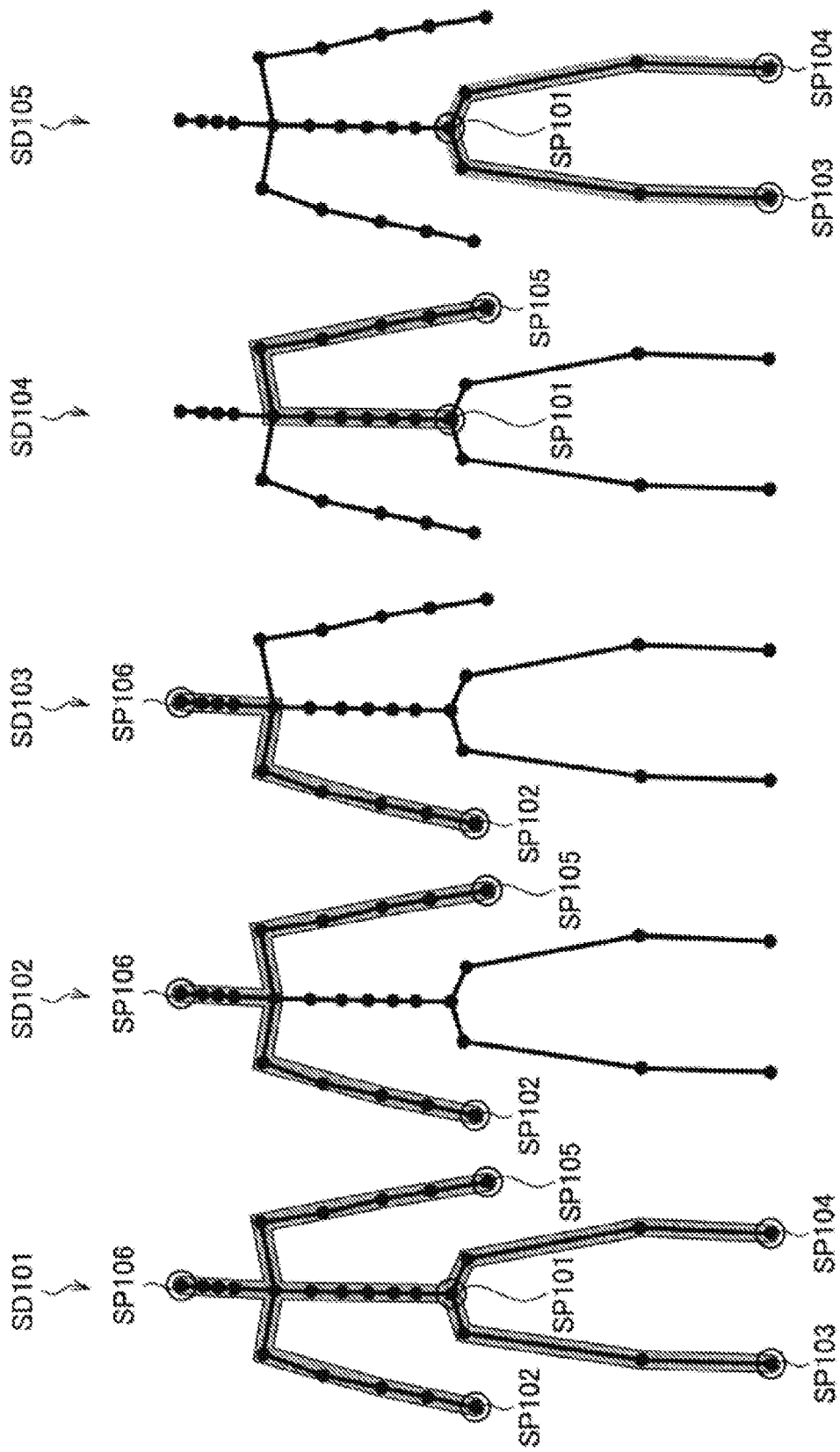

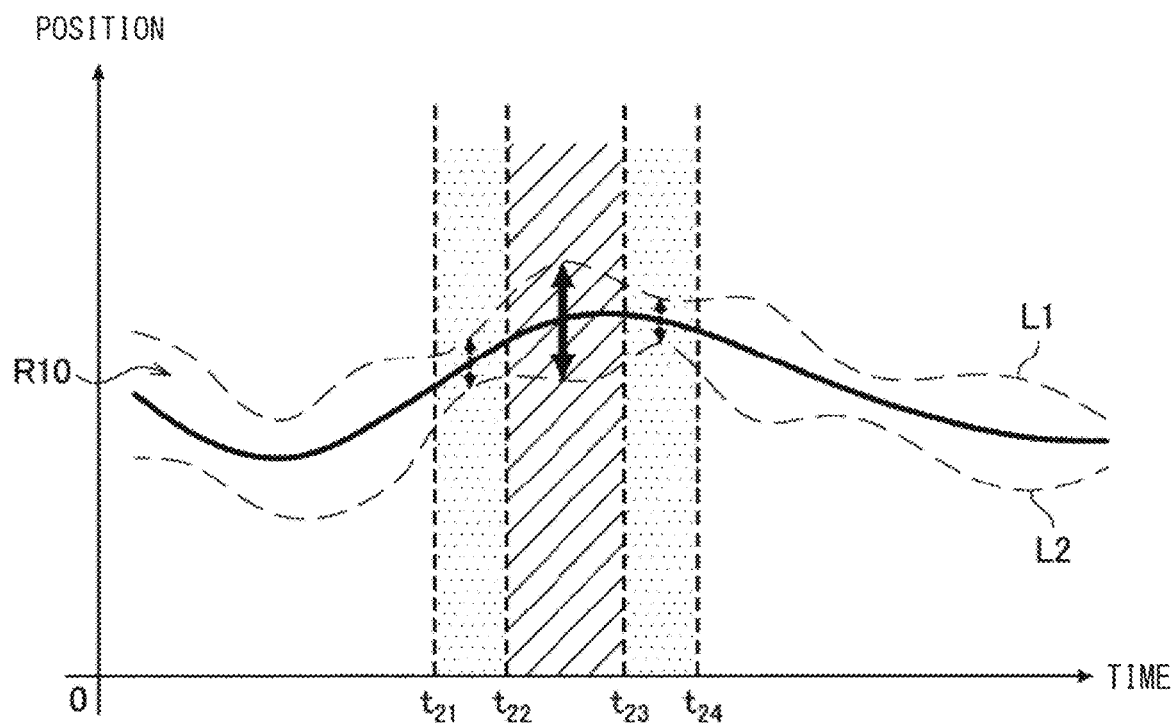
[ FIG. 17 ]

[ FIG. 18 ]
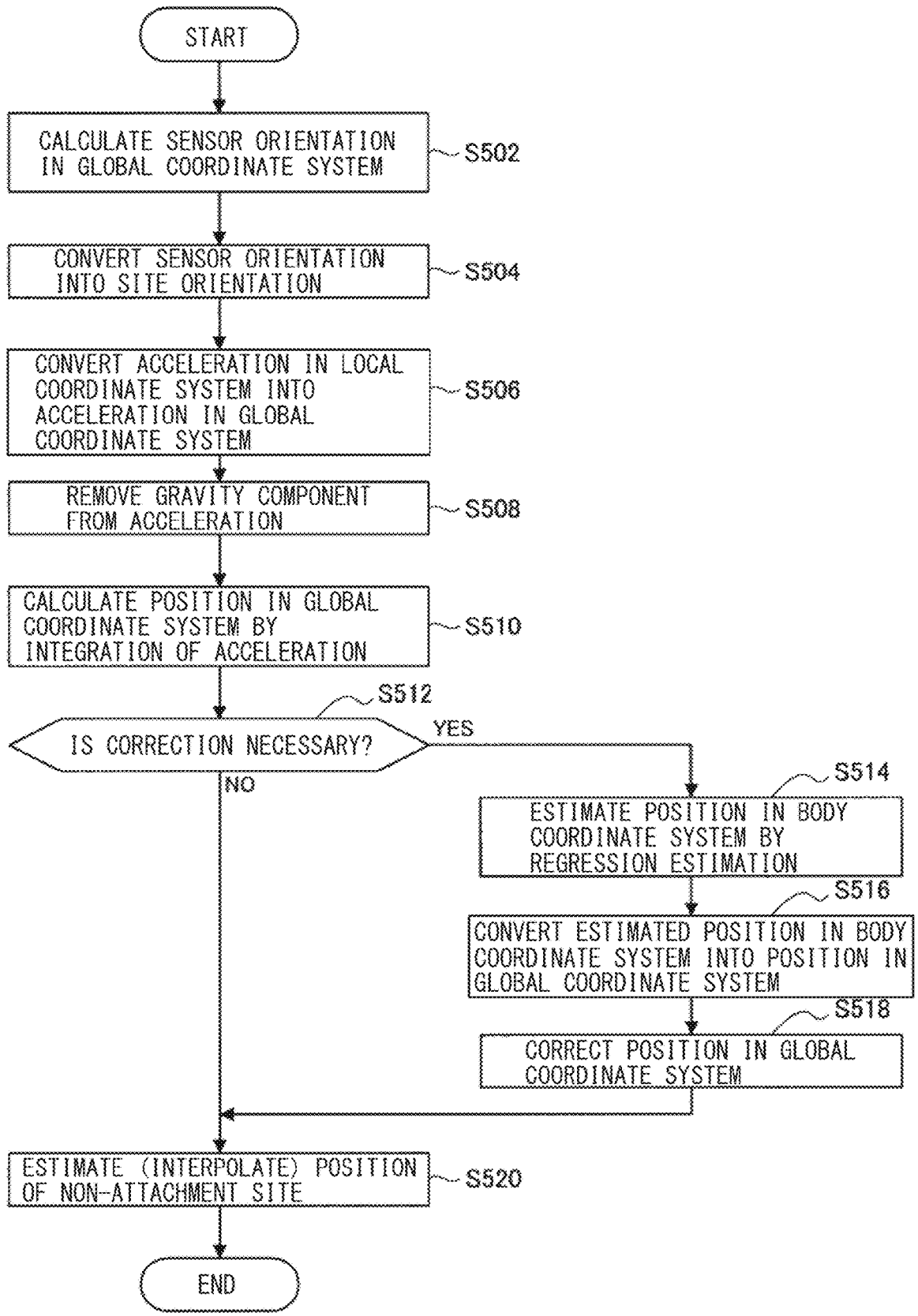

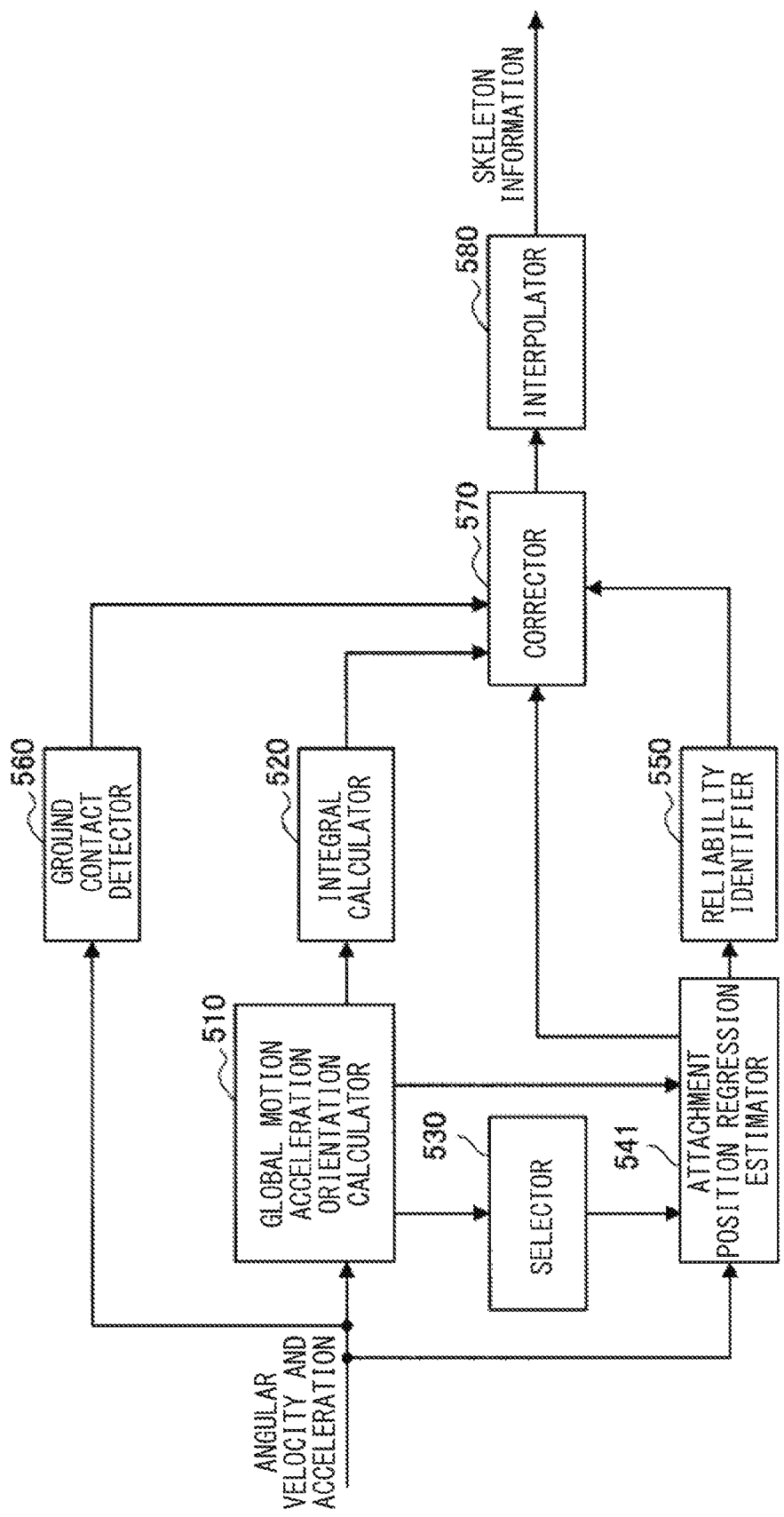

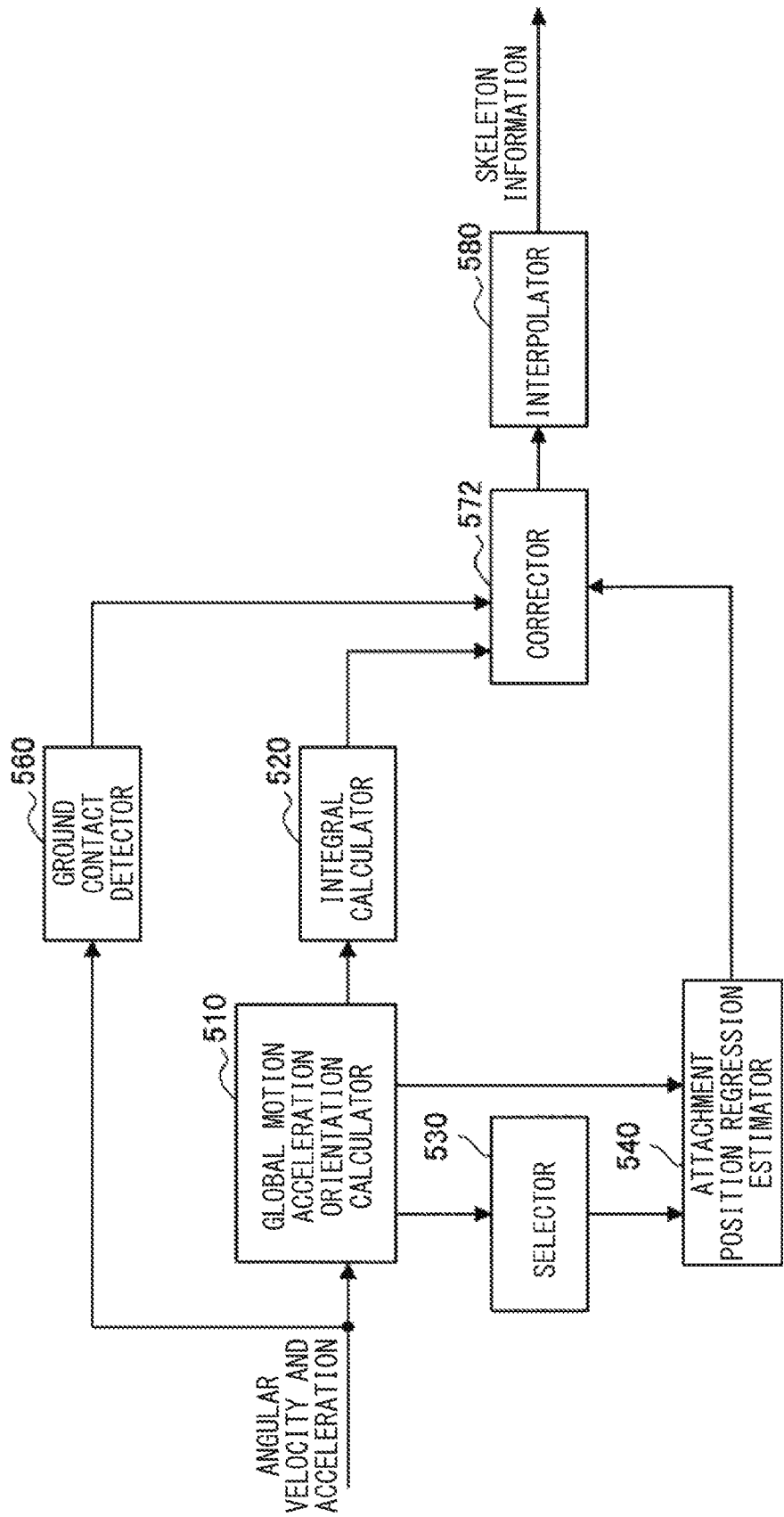

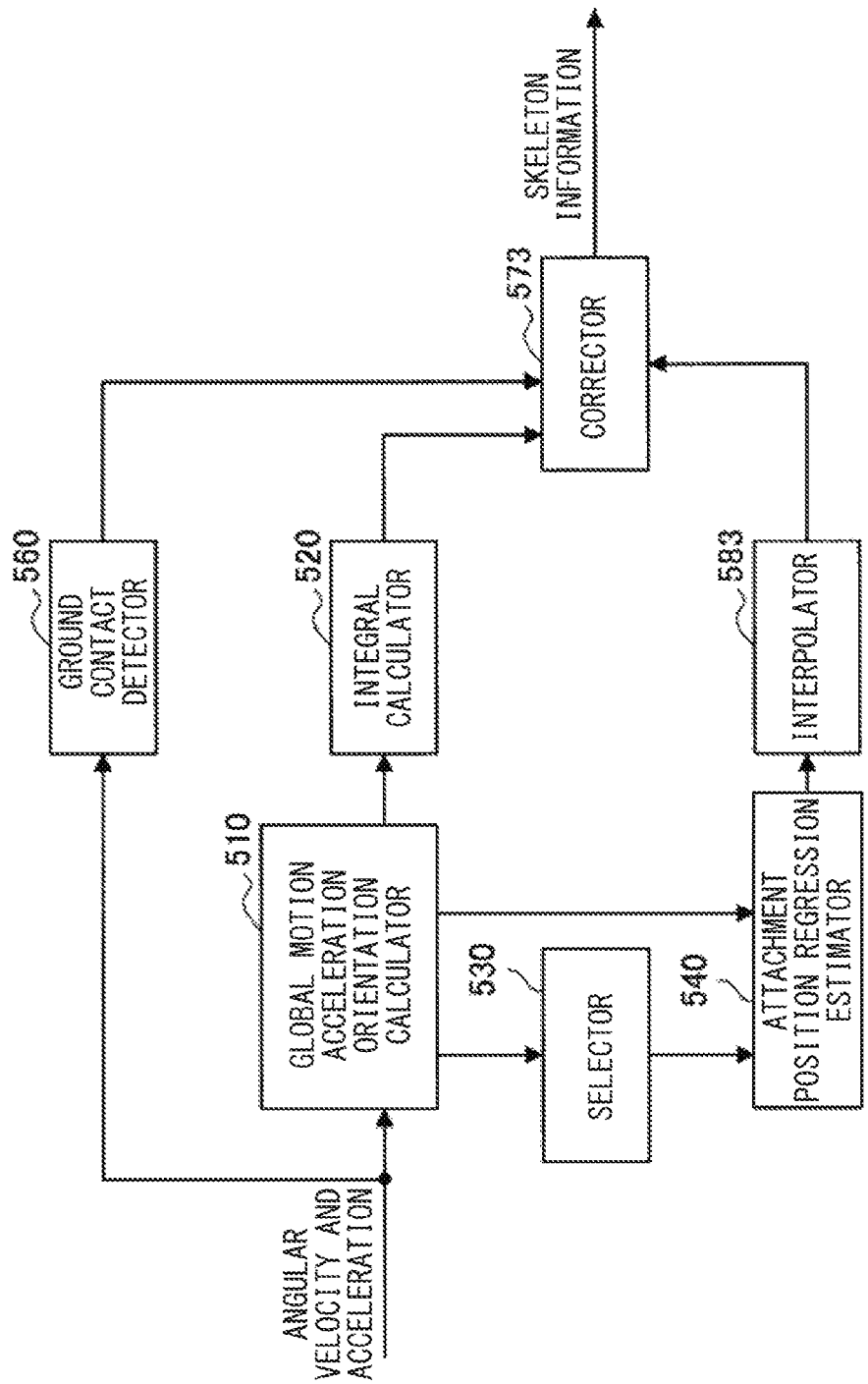
[FIG. 21]

[ FIG. 22 ]
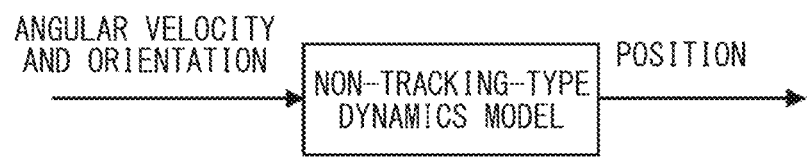
[ FIG. 23 ]
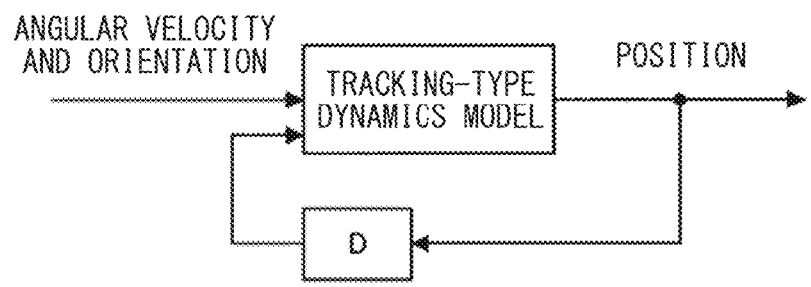

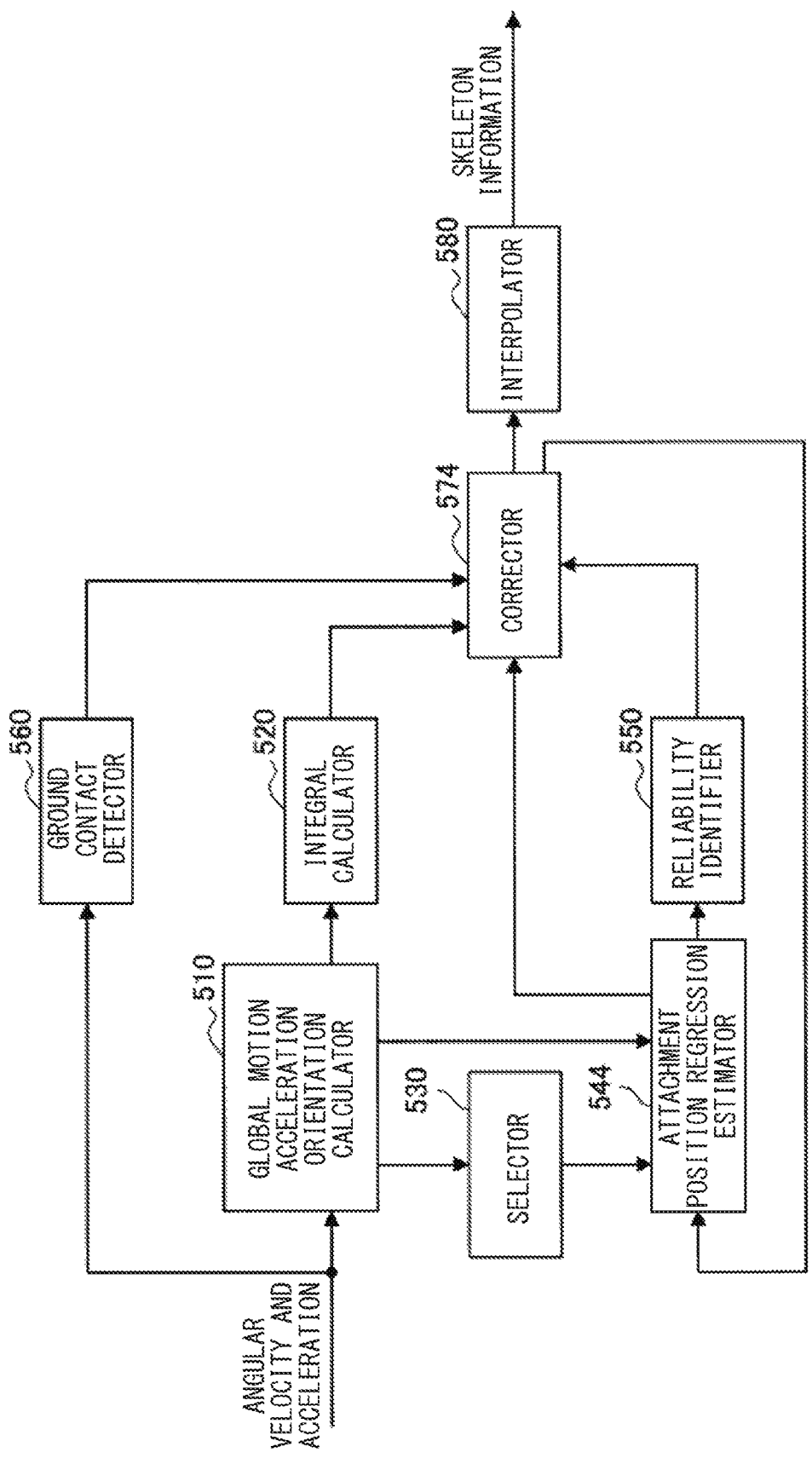
[FIG. 24]

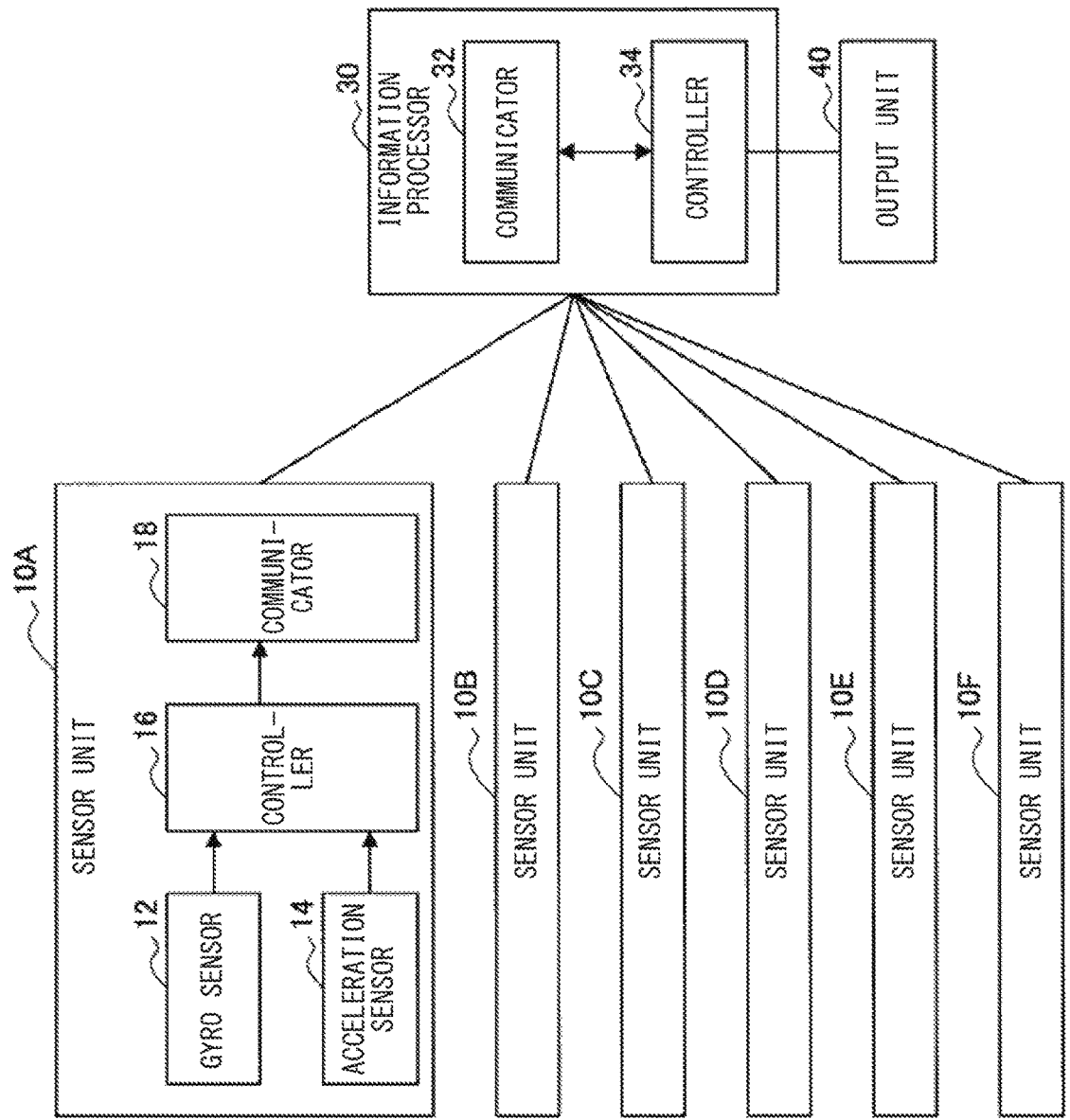
[FIG. 25]

[FIG. 26]
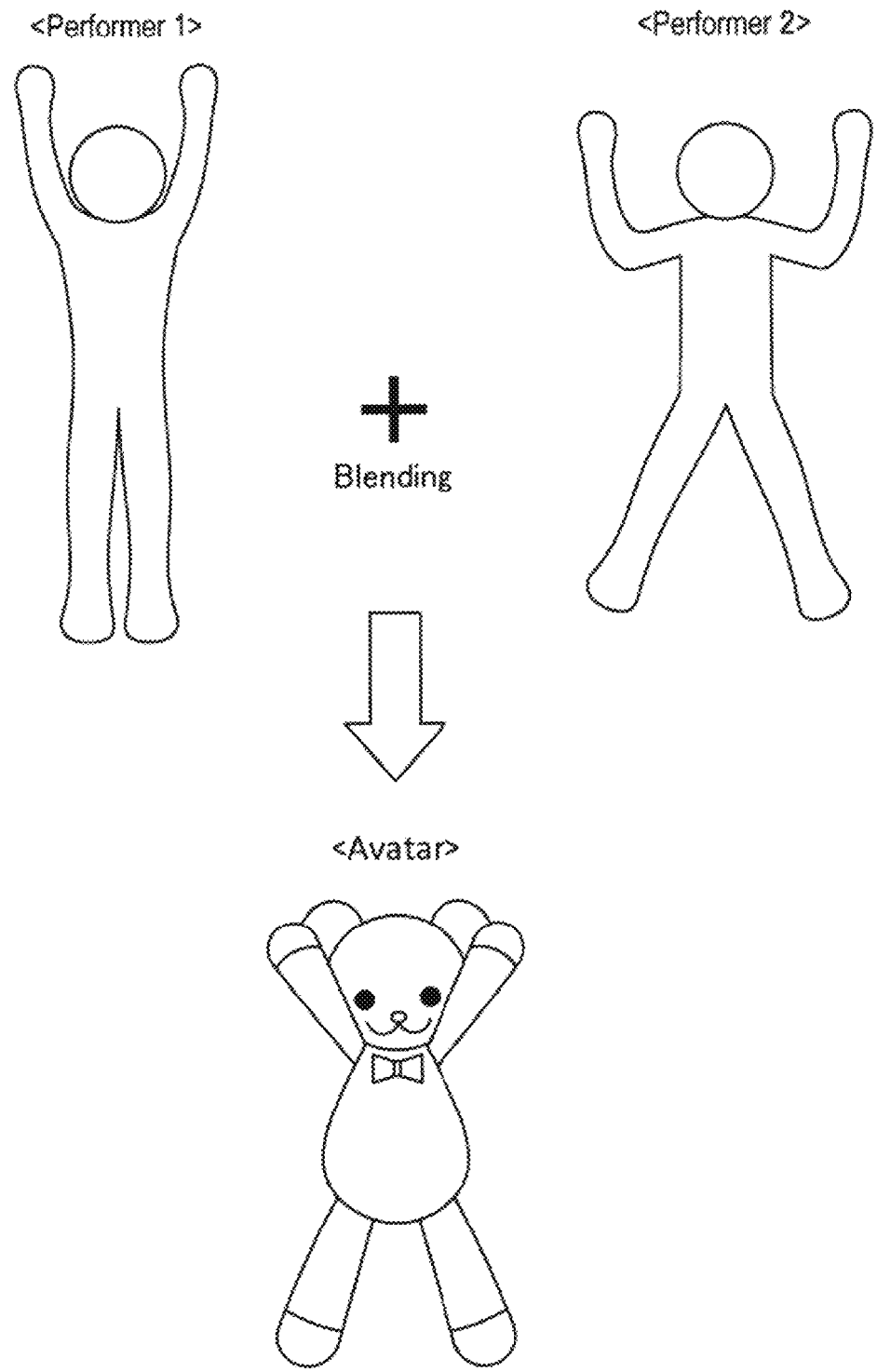

[FIG. 27]
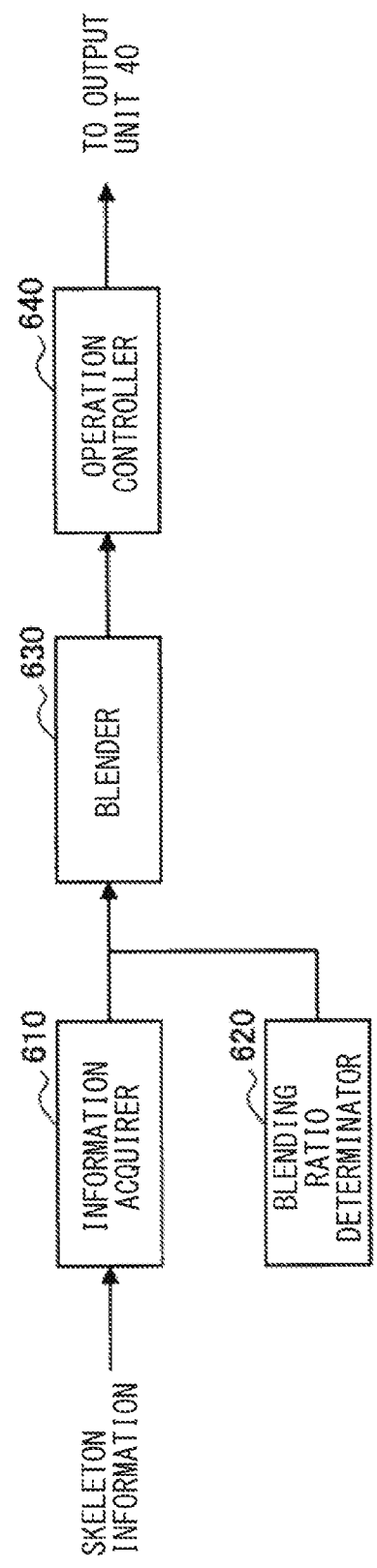

[FIG. 28]
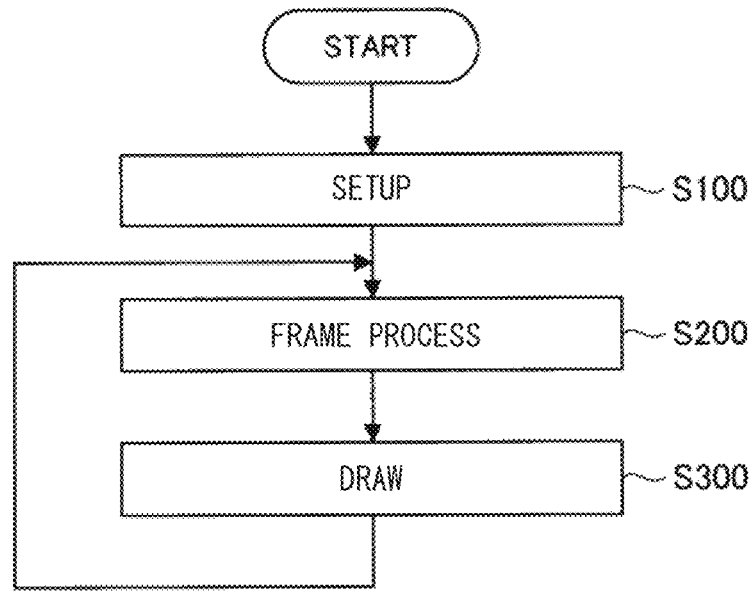
[FIG. 29]
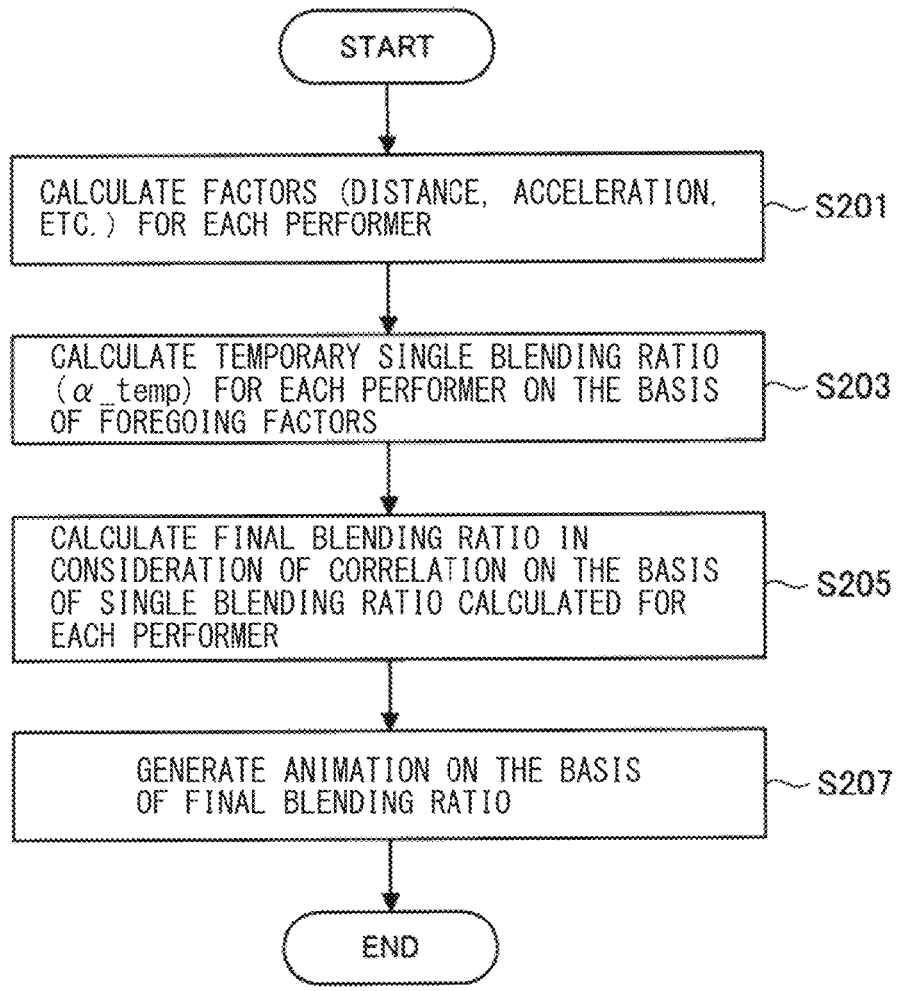

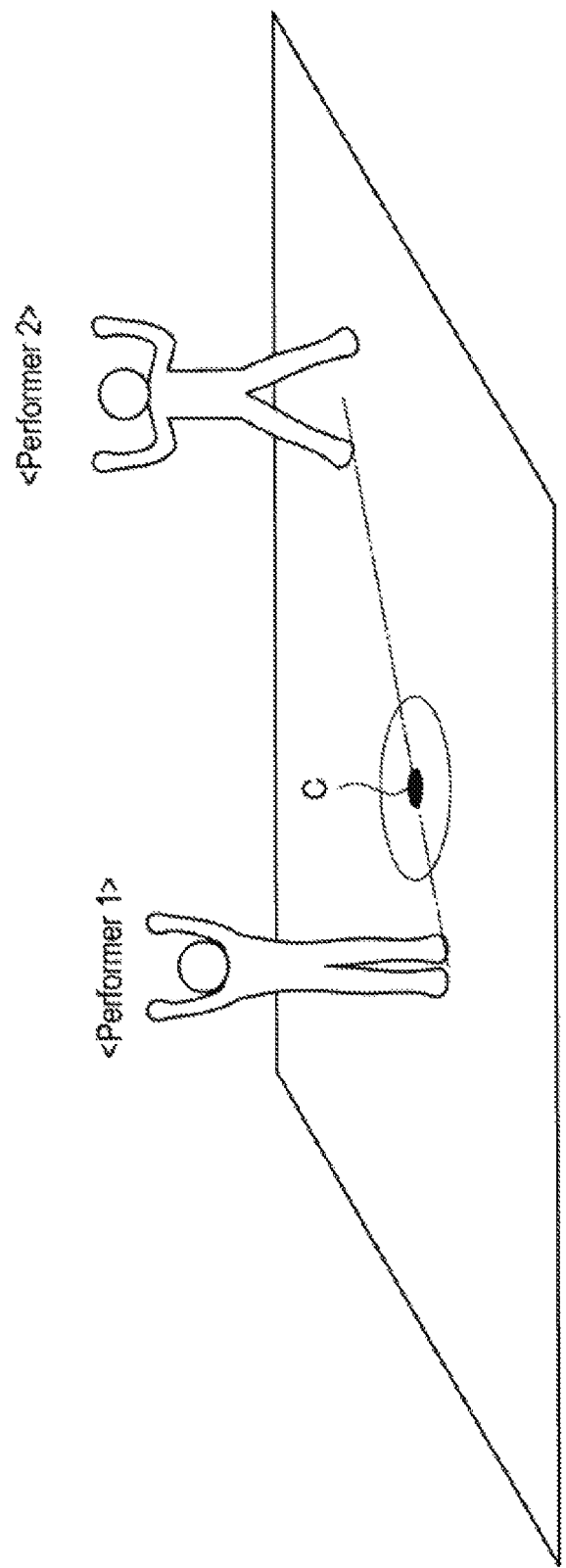
[FIG. 30]

[ FIG. 31 ]
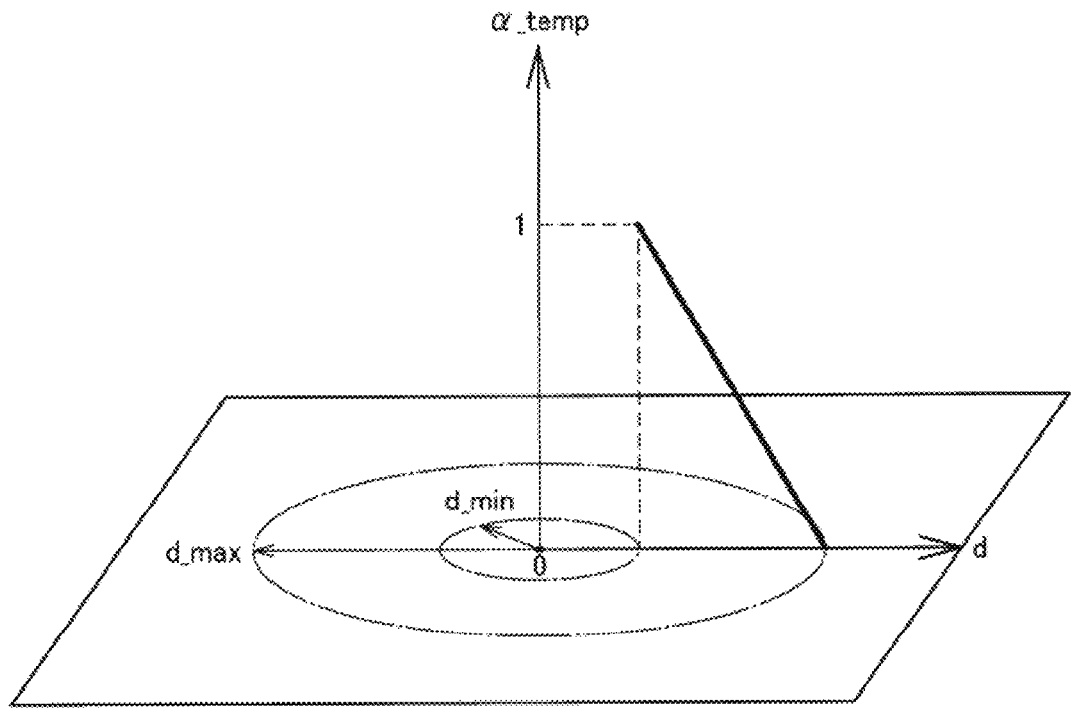
[ FIG. 32 ]
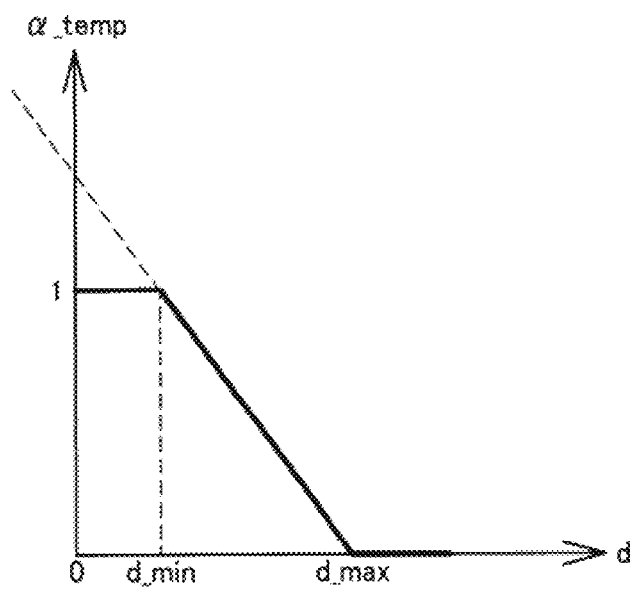

[FIG. 33]
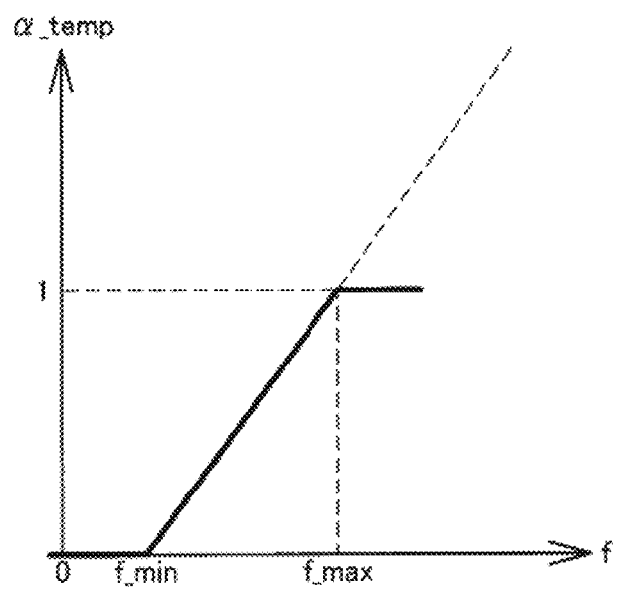

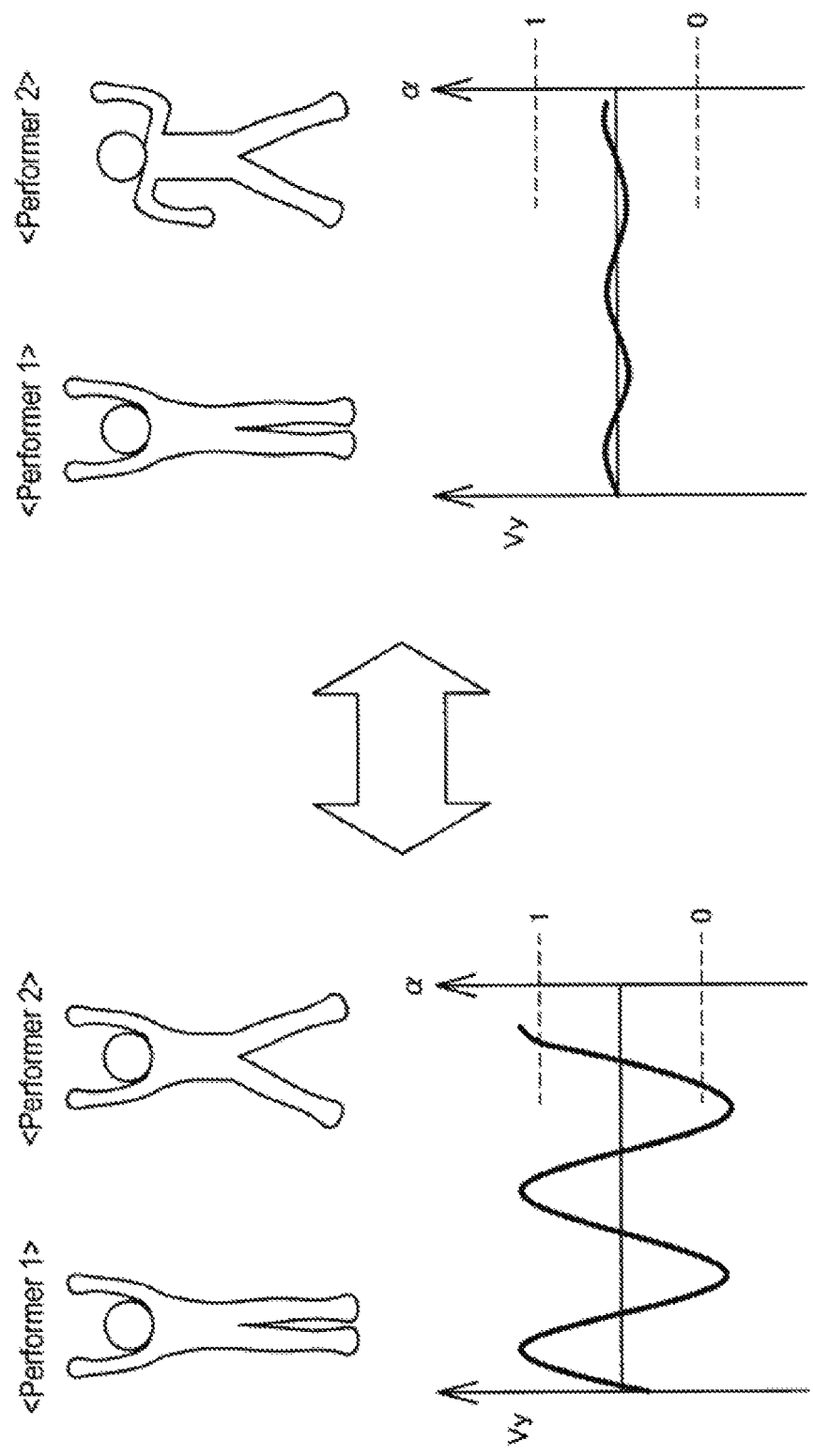
[FIG. 34]

[FIG. 35]
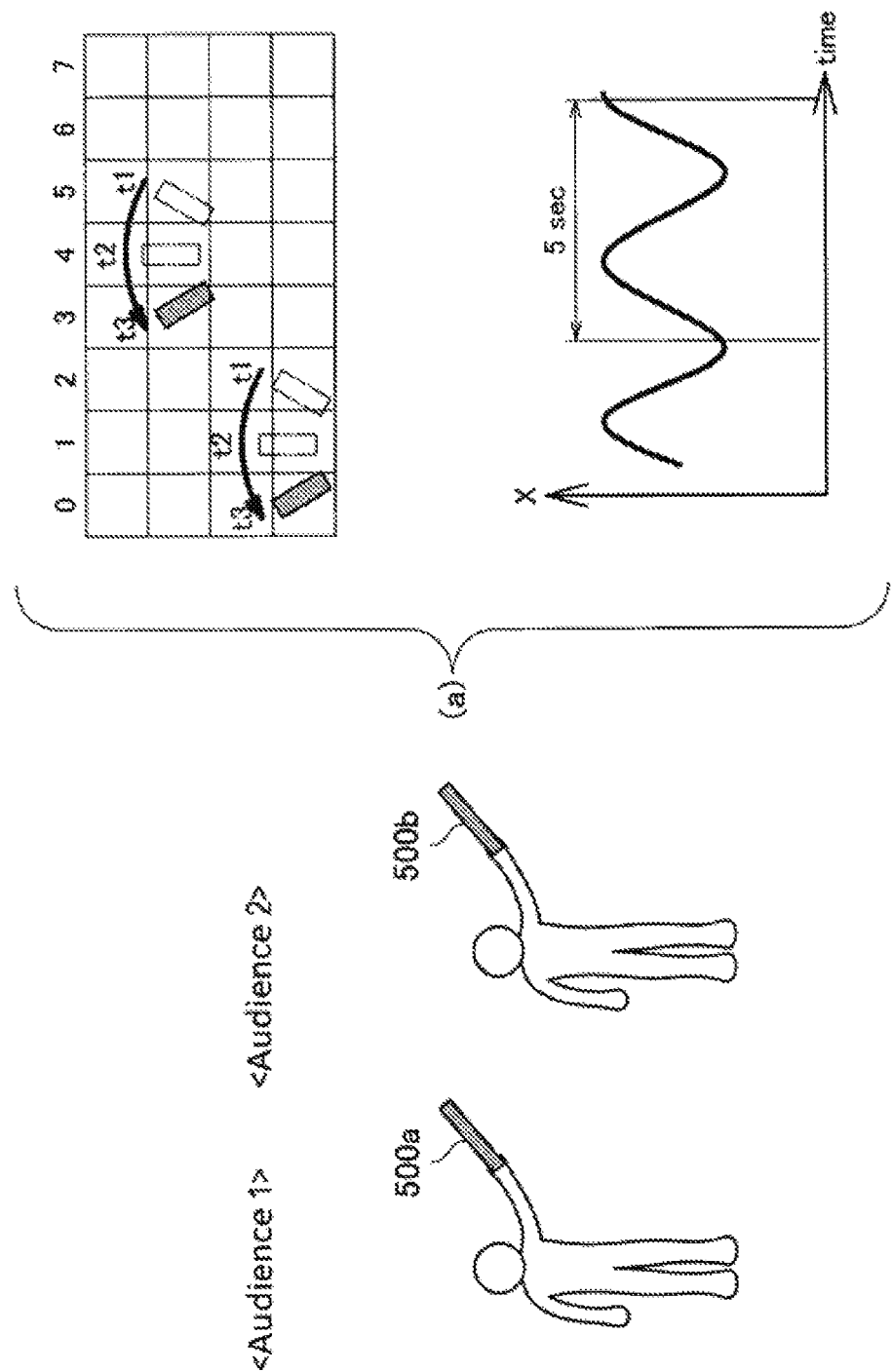

[FIG. 36]
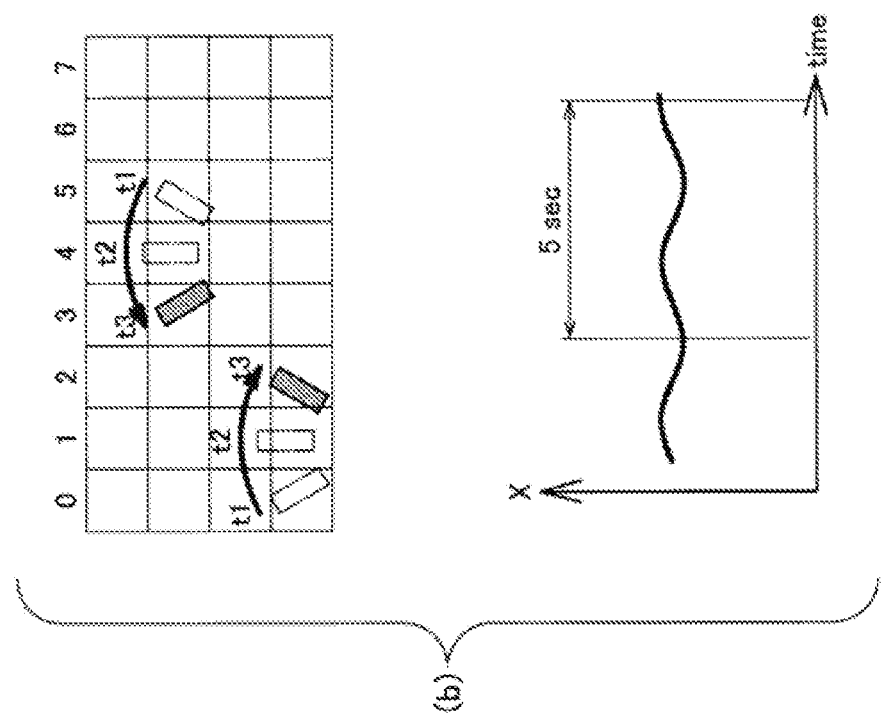
(b)
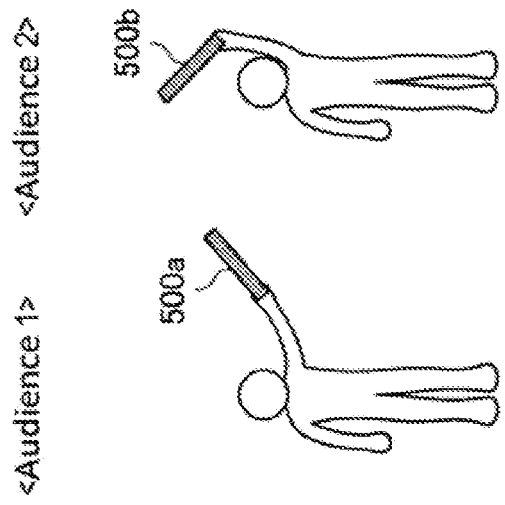
<Audience 1>  <Audience 2>

[FIG. 37]

|     | x |  |  |
| --- | --- | --- | --- |
|     | t1 | t2 | t3 |
| (a) | 5+2=7 | 4+1=5 | 3+0=3 |
| (b) | 5+0=5 | 4+1=5 | 3+2=5 |

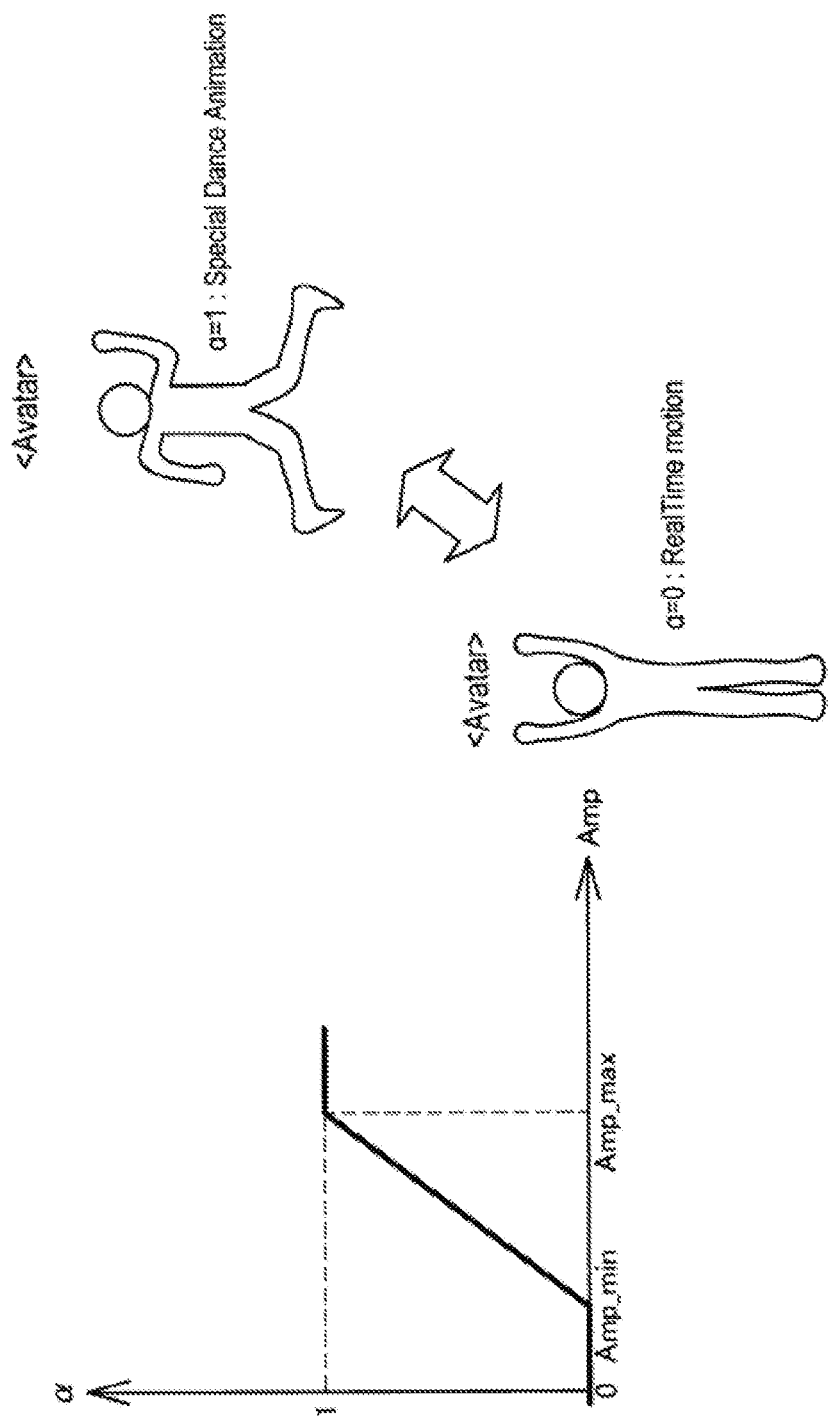

[ FIG. 39 ]
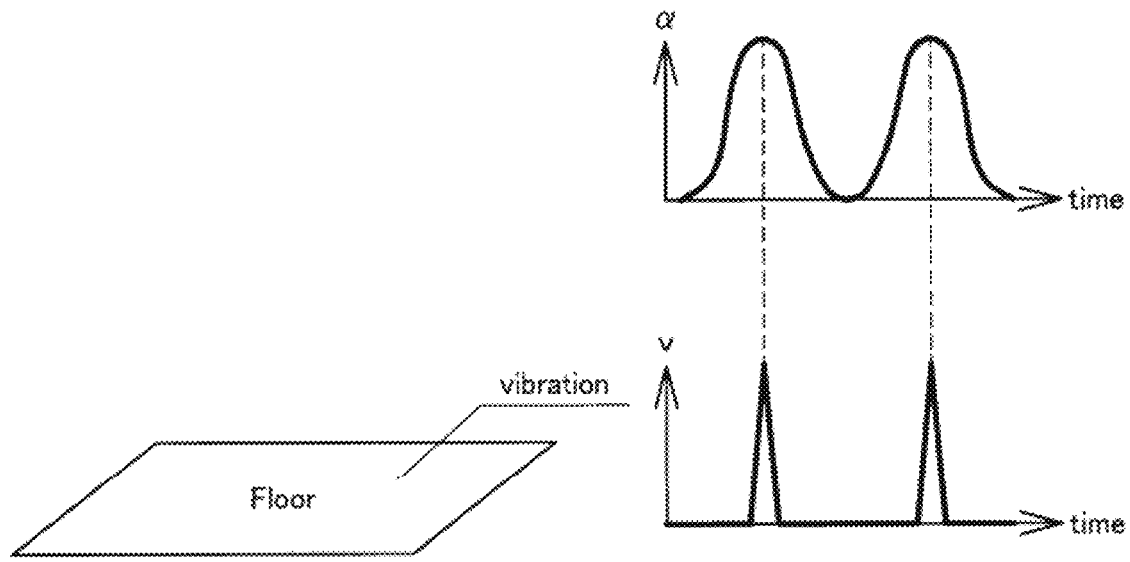
[ FIG. 40 ]
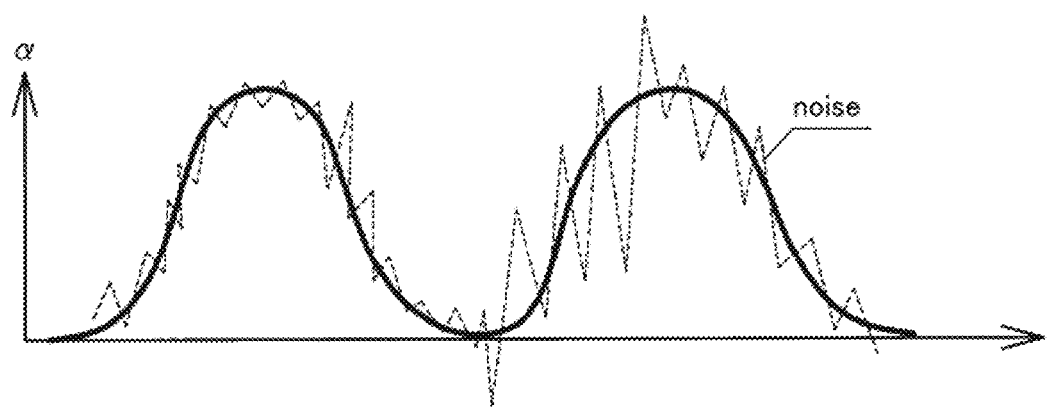

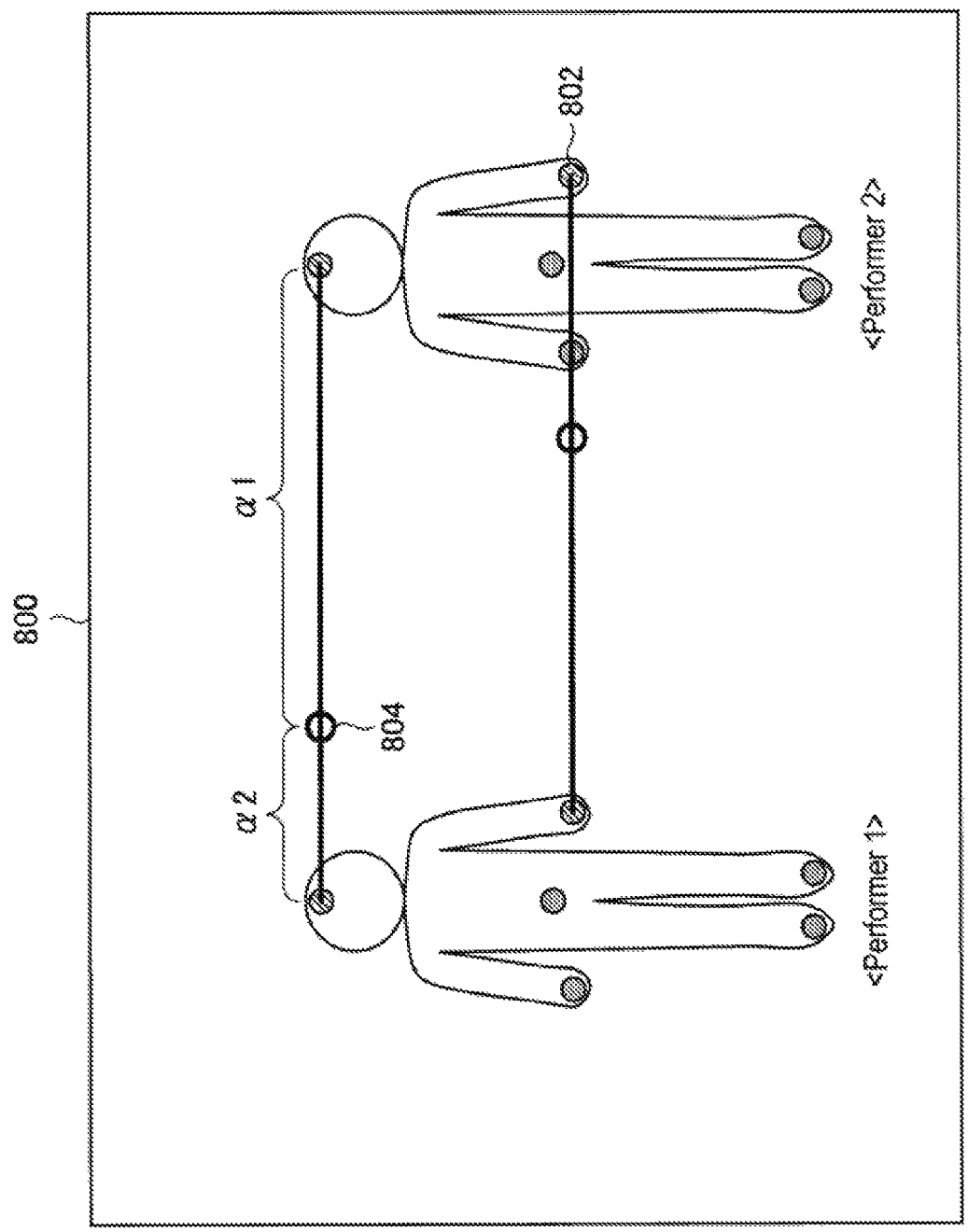

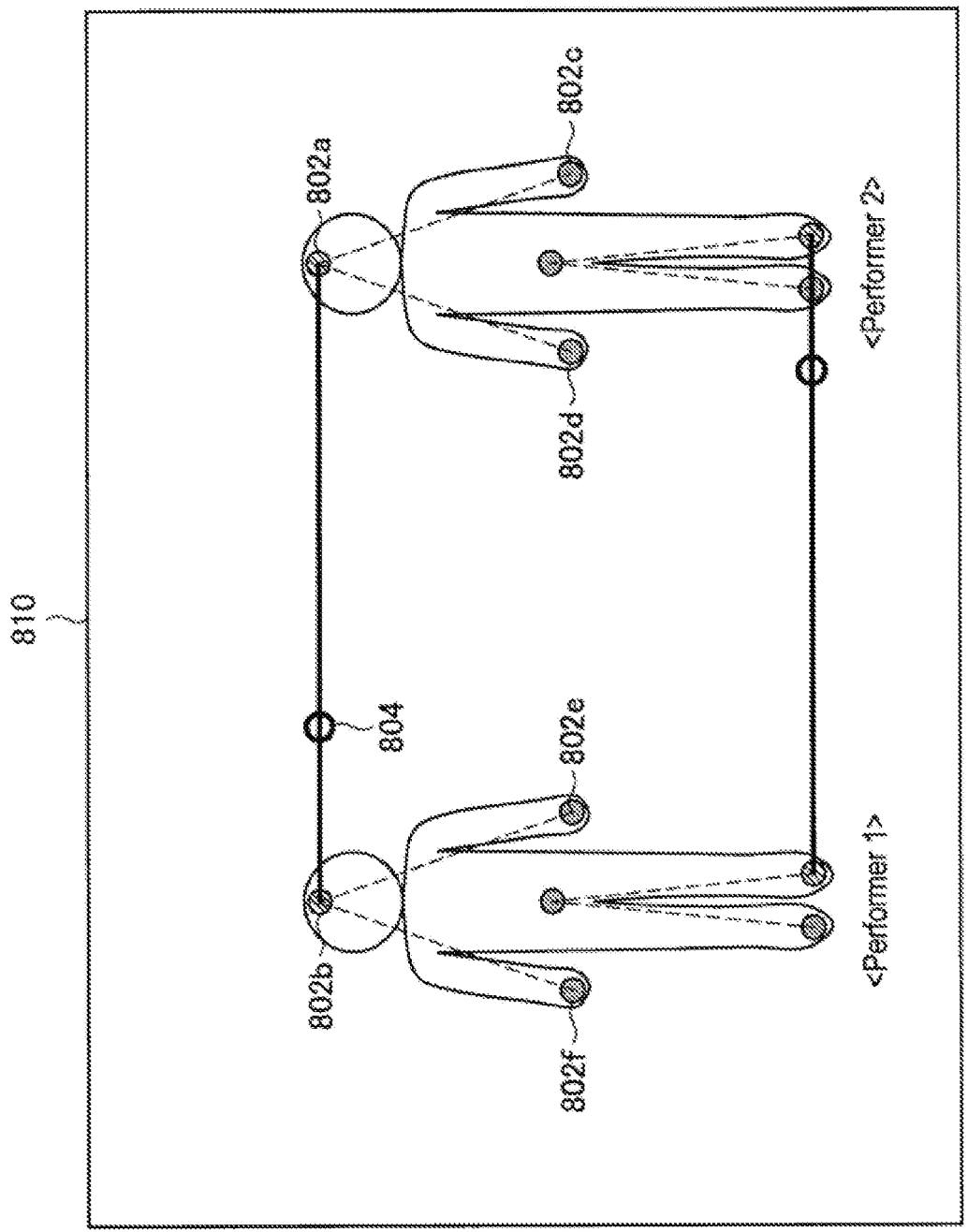
[FIG. 42]

[FIG. 43]
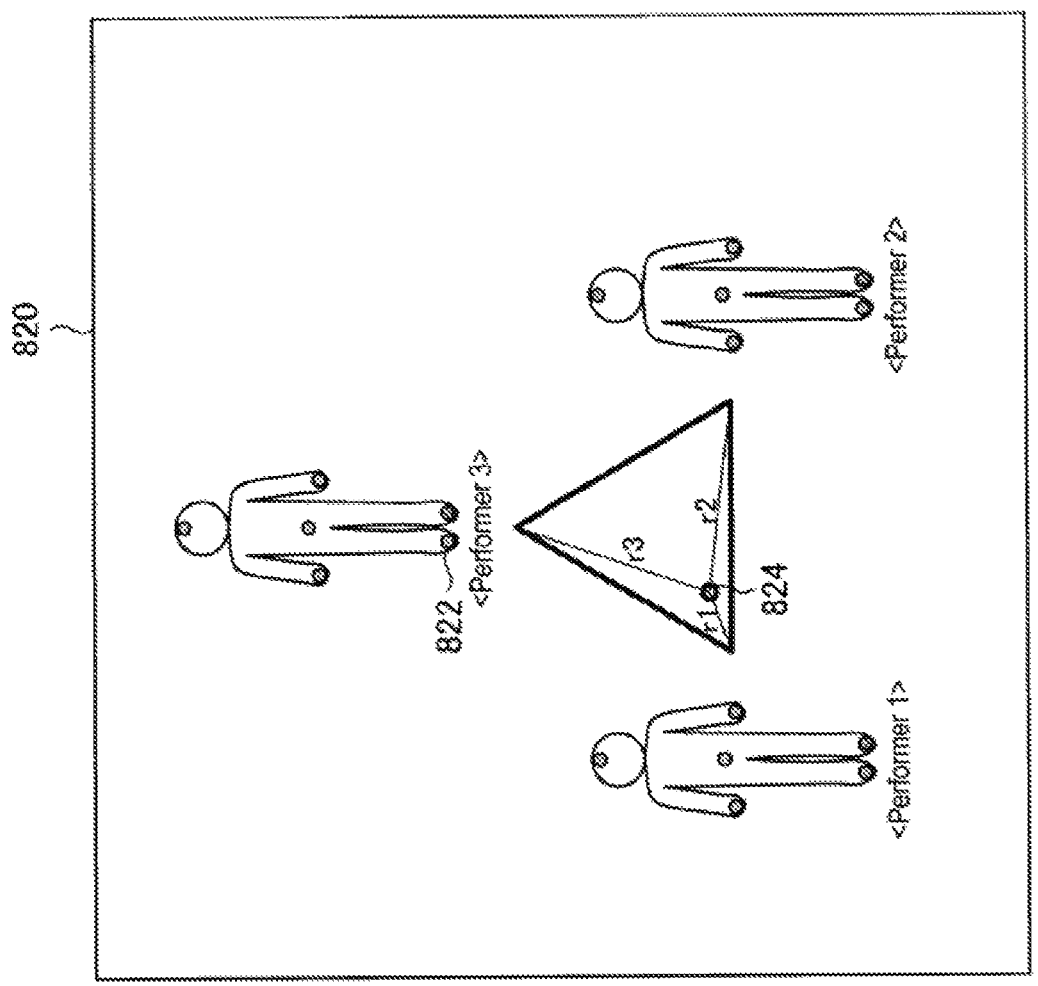

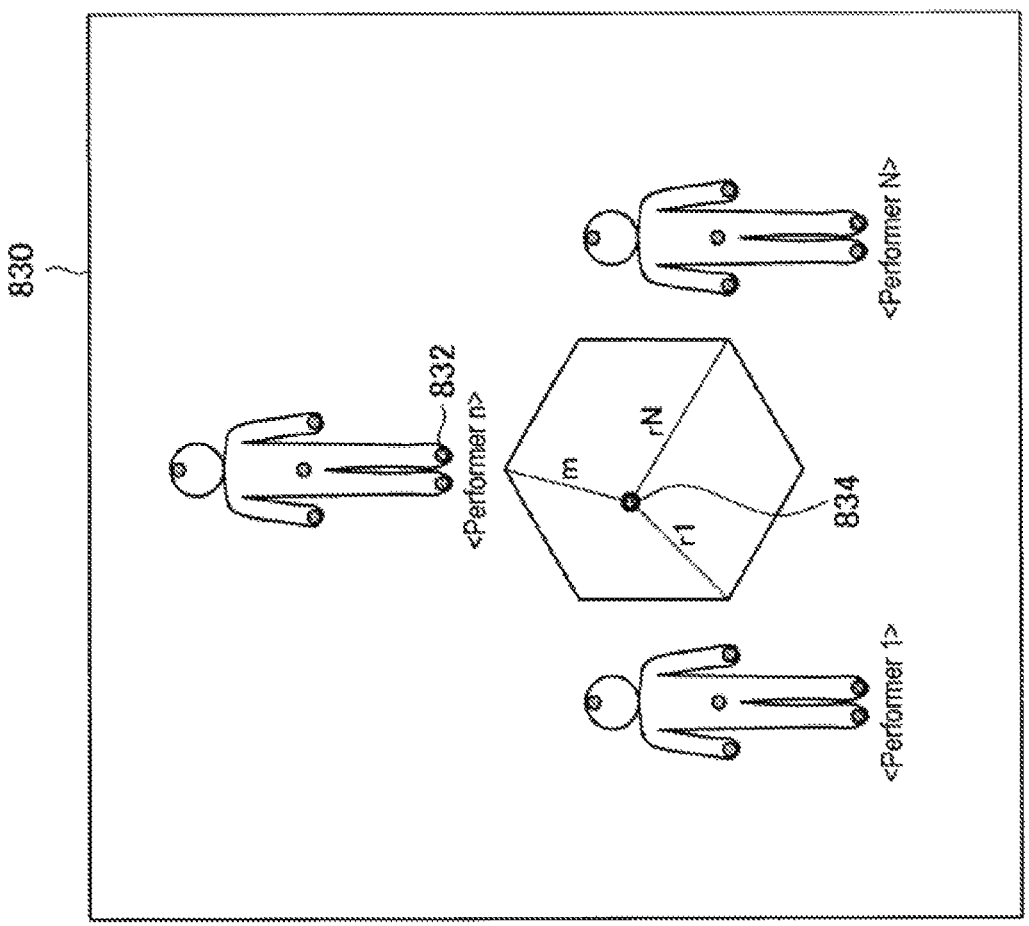
[FIG. 44]

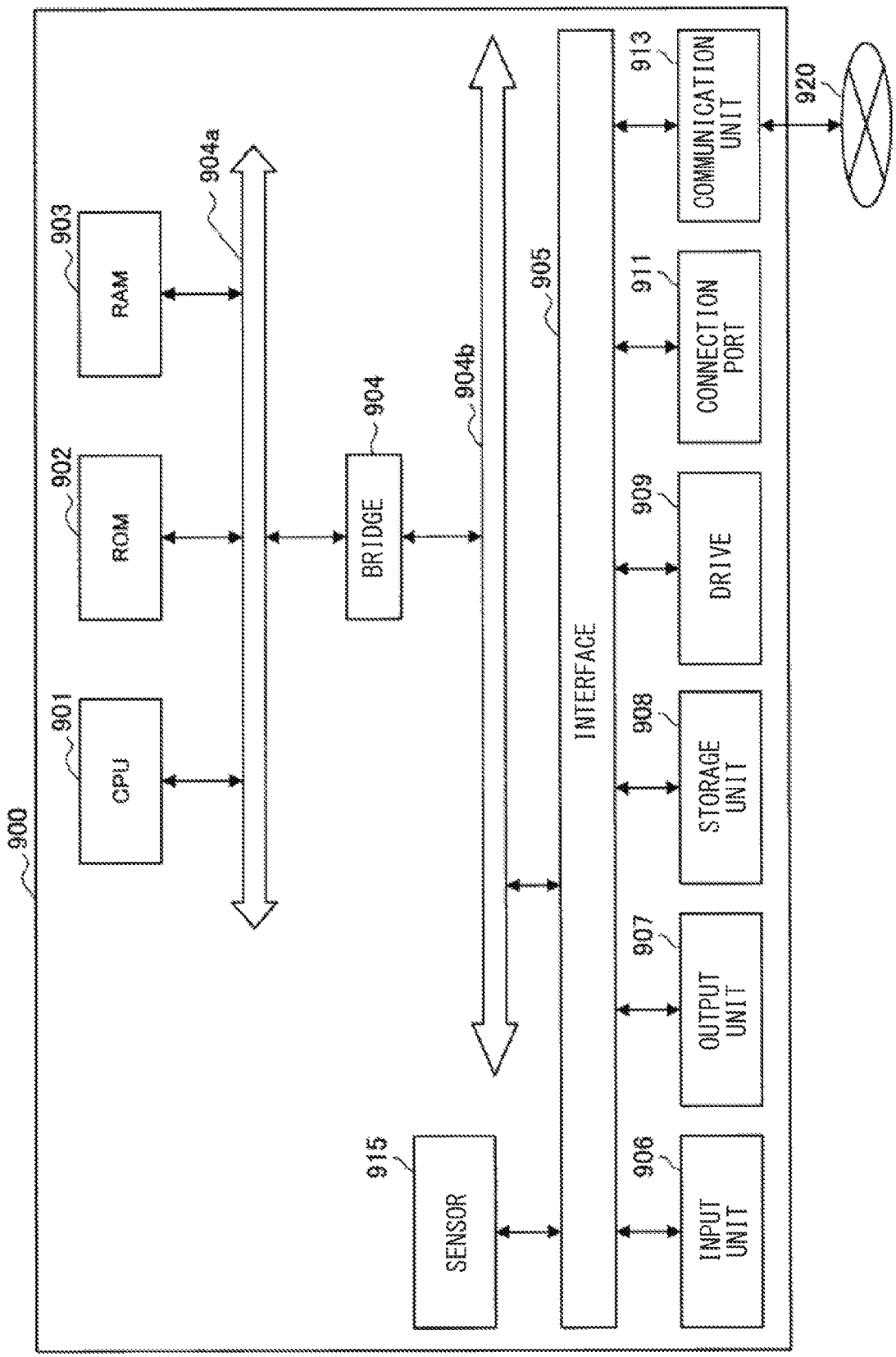
[FIG. 45]

PROGRAM, INFORMATION PROCESSOR, AND INFORMATION PROCESSING METHOD FOR BLENDING MOTIONS OF A PLURALITY OF ACTORS

CROSS REFERENCE TO PRIOR APPLICATION

This application is a National Stage Patent Application of PCT International Patent Application No. PCT/JP2019/016152 (filed on Apr. 15, 2019) under 35 U.S.C. § 371, which claims priority to Japanese Patent Application No. 2018-079335 (filed on Apr. 17, 2018), which are all hereby incorporated by reference in their entirety.

TECHNICAL FIELD

The present disclosure relates to a program, an information processor, and an information processing method.

BACKGROUND ART

In recent years, motion capture techniques for acquiring body motion information have been actively developed. The acquired body motion information is used, for example, for improvement in forms in sports, or in applications including VR (Virtual Reality) and AR (Augmented reality).

To acquire body motion information, for example, a position of a motion sensor attached to a body is calculated from sensor data (sensing data) acquired by the motion sensor by using an inertial navigation system (INS: Inertial Navigation System) (for example, PTL 1 below).

CITATION LIST

Patent Literature

PTL1: International Publication No. WO 2017/217050

SUMMARY OF THE INVENTION

Problems to be Solved by the Invention

Meanwhile, one use of motion capture techniques is to visualize motions of a user (performer, actor) acquired with the foregoing motion sensor in, for example, an avatar on a virtual space. In such a case, not only real-time reproduction of the captured motions of the user is desired but also, in a performance in a live show or the like, minimal expressions may be desired of the avatar for achieving an effective presentation.

Accordingly, in view of the above-described situation, the present disclosure proposes a new and improved program, information processor, and information processing method that make it possible to blend motions of a plurality of actors captured by using a motion capture technique and to reproduce the blended motions in real time in an avatar or the like on a virtual space.

Means for Solving the Problems

According to the present disclosure, there is provided a program that causes a computer to implement a control function of dynamically controlling a motion of an avatar in a virtual space or a robot on a real space, the control function being configured to: capture motions of a plurality of actors on the real space from respective motion sensors attached to the actors; blend the motions of the plurality of actors on the basis of a predetermined algorithm; and dynamically control the motion of the avatar or the robot on the basis of a blend result to cause the avatar or the robot to make a motion reflecting the motions of the plurality of actors.

Further, according to the present disclosure, there is provided an information processor including a controller that dynamically controls a motion of an avatar in a virtual space or a robot on a real space, the controller being configured to: capture motions of a plurality of actors on the real space from respective motion sensors attached to the actors; blend the motions of the plurality of actors on the basis of a predetermined algorithm; and dynamically control the motion of the avatar or the robot on the basis of a blend result to cause the avatar or the robot to make a motion reflecting the motions of the plurality of actors.

Further, according to the present disclosure, there is provided an information processing method including: capturing motions of a plurality of actors on a real space from respective motion sensors attached to the actors; blending the motions of the plurality of actors on the basis of a predetermined algorithm; and dynamically controlling a motion of an avatar in a virtual space or a robot on the real space on the basis of a blend result to cause the avatar or the robot to make a motion reflecting the motions of the plurality of actors.

Effect of the Invention

As described above, according to the present disclosure, it is possible to blend motions of a plurality of actors captured by using a motion capture technique and to reproduce the blended motions in real time in an avatar or the like on a virtual space.

It should be noted that the above-described effect is not necessarily limiting, and any of the effects illustrated in the present specification or other effects that may be expected from the present specification may be achieved together with or instead of the above-described effect.

BRIEF DESCRIPTION OF DRAWINGS

FIG. 1 is an image diagram that describes an overview of a first embodiment of the present disclosure.

FIG. 2 is an explanatory diagram that describes an existing motion capture technique using a forward kinematics calculation.

FIG. 3 is an explanatory diagram that describes the forward kinematics calculation.

FIG. 4 is an explanatory diagram that describes an approach using an inverse kinematics calculation.

FIG. 5 is an explanatory diagram that describes the inverse kinematics calculation.

FIG. 6 is an explanatory diagram that describes a first step according to the embodiment.

FIG. 7 is an explanatory diagram that describes a second step according to the embodiment.

FIG. 8 is a schematic diagram illustrating an overview of a position estimation process based on an inertial navigation system.

FIG. 9 is a schematic diagram illustrating a time-varying image of a position error that can occur in the position estimation process based on the inertial navigation system.

FIG. 10 is a schematic diagram illustrating an overview of a position estimation process based on a dynamics model.

FIG. 11 is a schematic diagram illustrating a time-varying image of a position error that can occur in the position estimation process based on the dynamics model.

FIG. 12 is a schematic diagram illustrating an overview of a position estimation process according to the embodiment.

FIG. 13 is a schematic diagram illustrating a time-varying image of a position error that can occur in the position estimation process according to the embodiment.

FIG. 14 illustrates an example of a unit configuration of a system according to the embodiment.

FIG. 15 illustrates an example of a functional configuration of the system according to the embodiment.

FIG. 16 is an explanatory diagram, illustrating an example of a combination of attachment sites and a dynamics model.

FIG. 17 illustrates an example of reliability identification by a reliability identifier 550.

FIG. 18 is a flowchart illustrating an operation example of the system according to the embodiment.

FIG. 19 illustrates a functional configuration example of a system according to a first modification example.

FIG. 20 illustrates a functional configuration example of a system according to a second modification example.

FIG. 21 illustrates a functional configuration example of a system according to a third modification example.

FIG. 22 is an explanatory diagram that describes an overview of a non-tracking-type dynamics model.

FIG. 23 is an explanatory diagram that describes an overview of a tracking-type dynamics model.

FIG. 24 illustrates a functional configuration example of a system according to a fourth modification example.

FIG. 25 illustrates a unit configuration example of a system according to a fifth modification example.

FIG. 26 is an image diagram that describes an overview of a second embodiment of the present disclosure.

FIG. 27 illustrates an example of a functional configuration of a system according to the embodiment.

FIG. 28 is a flowchart illustrating an operation example of the system according to the embodiment.

FIG. 29 is a flowchart that describes an operation in step S200 of FIG. 28.

FIG. 30 is an image diagram that describes an overview of example 1 of a blending ratio determination method according to the embodiment.

FIG. 31 is an image diagram (Part 1) that describes an operation of example 1 of the blending ratio determination method according to the embodiment.

FIG. 32 is an image diagram (Part 2) that describes the operation of example 1 of the blending ratio determination method according to the embodiment.

FIG. 33 is an image diagram that describes an operation of example 2 of the blending ratio determination method according to the embodiment.

FIG. 34 is an image diagram that describes an overview of example 3 of the blending ratio determination method according to the embodiment.

FIG. 35 is an image diagram (Part 1) that describes an operation of example 4 of the blending ratio determination method according to the embodiment.

FIG. 36 is an image diagram (Part 2) that describes the operation of example 4 of the blending ratio determination method according to the embodiment.

FIG. 37 is a table that describes the operation of example 4 of the blending ratio determination method according to the embodiment.

FIG. 38 is an image diagram (Part 3) that describes the operation of example 4 of the blending ratio determination method according to the embodiment.

FIG. 39 is an image diagram that describes an operation of example 5 of the blending ratio determination method according to the embodiment.

FIG. 40 is an image diagram that describes an operation of example 6 of the blending ratio determination method according to the embodiment.

FIG. 41 is an image diagram (Part 1) that describes UI example 1 according to the embodiment.

FIG. 42 is an image diagram (Part 2) that describes UI example 1 according to the embodiment.

FIG. 43 is an image diagram that describes UI example 2 according to the embodiment.

FIG. 44 is an image diagram that describes UI example 3 according to the embodiment.

FIG. 45 is an explanatory diagram illustrating a hardware configuration example.

MODES FOR CARRYING OUT THE INVENTION

Preferred embodiments of the present disclosure will be described in detail below with reference to the accompanying drawings. It is to be noted that, in the present specification and drawings, components that have substantially the same functional configurations are denoted by the same reference signs, and redundant descriptions thereof are thus omitted.

In addition, in the present specification and drawings, a plurality of components having substantially the same functional configurations is sometimes distinguished from each other by attaching different alphabets after the same reference signs. However, in a case where it is unnecessary in particular to distinguish a plurality of components having substantially the same functional configurations from each other, only the same reference signs are assigned.

It is to be noted that the description will be given in the following order.

<<1. Overview of First Embodiment>>
<<2. Principle of Present Technology>>
<<3. Configuration Example>>
<<4. Operation Example>>
<<5. Modification Examples>>
<<6. Overview of Second Embodiment>>
<<7. Hardware Configuration Example>>
<<8. Conclusion>>

1. Overview of First Embodiment

For example, skeleton information represented by a skeleton structure indicating the structure of a body is used to visualize information regarding motions of the body of a human, an animal, or the like. The skeleton structure includes information regarding sites, and bones which are line segments connecting the sites. The sites in the skeleton structure each correspond to, for example, an extremity site, a joint site, or the like. Further, the bones in the skeleton structure may correspond to, for example, human bones; however, the positions and the number of the bones may not necessarily be consistent with those in the actual human skeleton.

Site positions in the skeleton information are acquirable by, for example, attaching markers or motion sensors to respective corresponding sites of the body. For example, there exists a technique in which markers are attached to various sites of the body to acquire positions of the markers using an external camera or the like, and a technique in which motion sensors are attached to sites of the body to acquire position information of the motion sensors on the basis of sensor data acquired by the motion sensors.

Compared with the technique using markers attached to the body, the technique using motion sensors attached to the body is advantageous in that there is no need for any external camera, light source, or marker, resulting in portability and easiness of setting up. Further, the technique using motion sensors attached to the body is free from limitations by an image-capturing range of the camera, thus having an advantage in its availability even in a wide outdoor space, a space having a complicated shape that tends to generate a blind spot, a narrow- and small space, etc.

However, in order to estimate a whole-body skeleton with the technique using motion sensors attached to the body, it is necessary to attach a motion sensor to every joint, which sometimes places a heavy load on the user. Further, although dedicated suits have also been developed to suitably attach a large number of motion sensors to various sites on the user, the dedicated suits are sometimes costly to manufacture.

Accordingly, focusing on the above-described circumstances, the present inventors have created a first embodiment of the present disclosure. A system according to the first embodiment of the present disclosure makes it possible to acquire position information for a larger number of sites than the number of attached motion sensors while achieving a reduction in the number of the motion sensors to be attached. It is to be noted that in the present specification, a motion sensor is a device that senses motion of the body and may include an inertial sensor (an acceleration sensor, an angular velocity sensor), a geomagnetic sensor, a barometric sensor, an image sensor, and the like. In the following, an example in which at least an inertial sensor is attached as a motion sensor to the body will be mainly described.

An overview of the present embodiment will be described with reference to FIG. 1. FIG. 1 is an image diagram that describes the overview of the present embodiment. In the example illustrated in FIG. 1, six sensor units 10A to 10F are attached to six sites of the body of a user U1. The sensor units 10A to 10F include, for example, an inertial sensor (IMU: Inertial Measurement Unit) such as an acceleration sensor that acquires acceleration (Acceleration) or a gyro sensor (an angular velocity sensor) that acquires angular velocity (Angular Velocity). The sensor units 10A to 10F are preferably attached to a joint site (e.g., waist or head) serving as a reference in the body or to the near extremities of the body (wrist, ankle, head, etc.). In the example illustrated in FIG. 1, the sensor unit 10A is attached to the waist; the sensor units 10B and 10E are attached to the wrists; the sensor units 10C and 10D are attached to the ankles; and the sensor unit 10F is attached to the head, of the user UI. It is to be noted that in the following description, the sensor units 10A to 10F may be collectively and simply referred to as sensor units 10 in a case where it is not necessary to distinguish them from each other. Further, in the following, sites of the body to winch the sensor emits 10 are attached may also be referred to as attachment sites. In addition, the number of the sensor units 10 and attachment positions (positions of the attachment sites) are not limited to those in the example illustrated in FIG. 1.

The system according to the present embodiment acquires information regarding position (Position) and orientation (Orientation) of each of the attachment sites on the basis of sensor data acquired by the sensor units 10. As information (hereinafter also referred to as attachment site information) for the attachment sites P101 to P106 to which the sensor units 10A to 10F are attached, FIG. 1 illustrates attachment site information PD100 that includes position information and orientation information.

Further, on the basis of the position information and the orientation information for the attachment sites P101 to P106 to which the sensor units 10A to 10F are attached, the system according to the present embodiment estimates skeleton information including position information and orientation information for various sites of the skeleton structure. Here, in the present embodiment, the position information and the orientation information are estimated for, among sites of the skeleton structure, not only the attachment sites to which the sensor units 10 are attached but also a site to which none of the sensor units 10 is attached (hereinafter also referred to as a non-attachment site).

In the example of FIG. 1, skeleton information SD100 is illustrated that includes position information and orientation information for various sites in the skeleton structure. The skeleton information SD100 includes information for a non-attachment site SP107 as well as information for an attachment she SP101 corresponding to the attachment site P101 and an attachment site SP102 corresponding to the attachment site P102.

In addition to the information for the sites, the skeleton information may also include information (position information, orientation information, etc.) for bones. For example, in the example illustrated in FIG. 1, the skeleton information SD100 may include information for a bone SB101. For example, on the basis of position information and orientation information for sites in the skeleton structure, it is possible to identify information for a bone between the sites.

As described above, according to the present embodiment, information for a non-attachment site to which none of the motion sensors is attached is estimated on the basis of information for the attachment sites to which the motion sensors are attached. This makes it possible to reduce the number of the motion sensors to be attached while maintaining the number of sites for which information is to be acquired. In the following, a description is given of the technical principle according to the present embodiment for achieving the above-described effects.

2. Principle of Present Technology

2-1. Approach of Present Embodiment

As an existing motion capture technique, there is a technique of acquiring skeleton information by forward kinematics (FK: Forward Kinematics) calculation. The forward kinematics calculation is a method of calculating the position of an extremity site on that basis of orientations of joint sites.

FIG. 2 is an explanatory diagram that describes the existing motion capture technique using the forward kinematics calculation. FIG. 2 illustrates skeleton Information SD90 represented by a skeleton structure.

In the skeleton information SD90 illustrated in FIG. 2, attachment sites to which sensor units including inertial sensors are attached are marked with circles. Thus, sites SP91 to SP96 are the attachment sites. Here, in a case where the sensor units include angular velocity sensors, it is possible to identify orientation information (angle information) for the attachment sites by using an attitude measurement technique such as an AHRS (Attitude and Heading Reference System).

For example, in a case where a body coordinate system is set with the site SP91 corresponding to the waist of the body as a reference (a point of origin), it is possible to identify position information for the sites SP92 to SP96 in the body coordinate system by performing the forward kinematics calculation on the basis of orientation information for the sites SP91 to SP95. Note that in the following description, the site used as a reference in the body coordinate system will sometimes be referred to as a root site.

Here, the forward kinematics calculation will be described with reference to FIG. 3. FIG. 3 is an explanatory diagram that describes the forward kinematics calculation. For the sake of simplicity, FIG. 3 illustrates an example in which an arm is regarded as a simple linkage with two degrees of freedom.

In the example illustrated in FIG. 3, a site SP81 is the root site, and there is illustrated an xy coordinate system (a plane coordinate system) with the site SP81 as the reference (the point of origin). In the forward kinematics calculation, as described above, the orientation information for each site is known. In the example illustrated in FIG. 3, an angle (h formed between a bone SB81 and the x-axis based on the orientation of the site SP81, and an angle $\theta_2$ formed between the bone SB81 and a bone SB82 based on the orientation of a site SP82 are known. Further, in the forward kinematics calculation, the distances between sites, that is, the lengths of bones are also known. In the example illustrated in FIG. 3, the length $l_1$ of the bone SB81 and the length $l_2$ of the bone SB82 are known.

According to the forward kinematics calculation, it is possible to calculate a position $(x_1, y_1)$ of a site SP83 using the known information as described above. Specifically, the position $(x_1, y_1)$ of the site SP83 is expressed by the following equations (1) and (2).

[Math. 1]

$$x_1 = l_1 \cos \theta_1 + l_2 \cos(\theta_1 + \theta_2) \quad (1)$$

$$y_1 = l_1 \sin \theta_1 + l_2 \sin(\theta_1 + \theta_2) \quad (2)$$

While FIG. 3 illustrates an example of a planar and simple mechanism, it is also possible to perform the forward kinematics calculation in a similar manner even in a case of a three-dimensional and more complex mechanism. That is, it is possible to identify the position information for an extremity site by using the orientation information for a joint site between the root site serving as a reference and the extremity site, and information regarding the distance between the sites. In addition, not only the position information for the extremity sites but also the position information for a joint site located between the root site and an extremity site in the skeleton structure (for example, the position information for the site SP82 in the example illustrated in FIG. 3) is identified by the forward kinematics calculation.

One example of existing motion capture techniques using the forward kinematics calculation has been described above. However, as has been described with reference to FIGS. 2 and 3, identifying position information for each site by using the forward kinematics calculation necessitates orientation information for each joint site. Thus, the use of the forward kinematics calculation is a factor responsible for an increase in the number of motion sensors to be attached to the body.

Accordingly, in the present embodiment, skeleton information is acquired by using inverse kinematics (IK: Inverse Kinematics) calculation instead of the forward kinematics calculation described above. The inverse kinematics calculation is a method of calculating the orientation of each joint site on the basis of the position of an extremity site.

FIG. 4 is an explanatory diagram that describes an approach using the inverse kinematics calculation. FIG. 4 illustrates skeleton information SD90 represented by a skeleton structure similar to FIG. 2.

In the skeleton information SD90 illustrated in FIG. 4, attachment sites to which sensor units including inertial sensors are attached are marked with circles. Thus, sites SP91 to SP96 are the attachment sites. Meanwhile, in the skeleton information SD90 illustrated in FIG. 4, the sites to which any sensor units including inertial sensors are unattached are marked with crosses. Specifically, the sites SP92 to SP95, which are between the site 91 and the site 96, are the non-attachment sites.

Assume here that a body coordinate system has been set with the site SP91 corresponding to the waist of the body as the reference (the point of origin) and the position information for the site SP96 in the body coordinate system has been acquired. In such a case, it is possible to identify orientation information and position information for the sites SP92 to SP95 by performing the inverse kinematics calculation on the basis of the position information for the site SP96, which is an extremity site.

Here, the inverse kinematics calculation will be described with reference to FIG. 5. FIG. 5 is an explanatory diagram that describes the inverse kinematics calculation. For the sake of simplicity, FIG. 5 illustrates an example in which an arm is regarded as a simple linkage with two degrees of freedom.

In the example illustrated in FIG. 5, the site SP81 is the root site, and there is illustrated an xv coordinate system (a plane coordinate system) with the site SP81 as the reference (the point of origin). Here, as illustrated in the upper left in FIG. 5, assume that the length $l_1$ of the bone SB81 whose one end point is the site SP81 and the length $l_2$ of the bone SP82 whose one end point is the site SP83 are known.

In the inverse kinematics calculation, an angle formed between the bone SB81 and the x-axis and an angle formed between the bone SB81 and the bone SB82 are calculated using the known information as described above. In the inverse kinematics calculation, however, there can exist a plurality of solutions. In the example of FIG. 5, obtained are a solution that, as illustrated in the upper right in FIG. 5, an angle $\theta_{11}$ is formed between the bone SB81 and the x-axis and an angle $\theta_{21}$ is formed between the bone SB81 and the bone SB82; and a solution that, as illustrated in the lower right in FIG. 5, an angle $\theta_{12}$ is formed between the bone SB81 and the x-axis and an angle $\theta_{22}$ is formed between the bone SB81 and the bone SB82. It is to be noted that FIG. 5 illustrates an example of a planar and simple mechanism; therefore, there can exist a larger number of solutions in a case of a three-dimensional mechanism or in a case where there are a larger number of joint sites, for example.

The approach using the inverse kinematics calculation has been described above. Next, an overview of processing according to the present embodiment will be described. In the present embodiment, as described above, skeleton information (positions and orientations of joint sites) is acquired using the inverse kinematics calculation. Thus, the processing is performed in two general steps as illustrated in FIG. 6 and FIG. 7 described below.

FIG. 6 is an explanatory diagram that describes a first step according to the present embodiment. As has been described with reference to FIG. 1, in the present embodiment, information regarding acceleration and angular velocity is acquirable from two or more inertial sensors attached to two or more sites of the body. Further, it is possible to obtain information regarding acceleration (three-dimensional) and orientation (four-dimensional) in a global coordinate system from the information regarding acceleration and angular velocity acquired from the inertial sensors. It is to be noted that the global coordinate system is, for example, a coordinate system for common use by a plurality of sensors, devices, etc., and may be a coordinate system corresponding to a real space. The attachment site information PD10 illustrated in FIG. 6 includes information regarding acceleration and orientation for the attachment sites P11 to P16 acquired by the inertial sensors, and therefore includes information of 6×7=42 dimensions in total.

In the first step, position estimation for the attachment sites is performed (S100) on the basis of the attachment site information PD10, and thereby attachment site information PD12 is obtained that includes position information indicating positions (three-dimensional) of the attachment sites P11 to P16. It is to be noted that in a case where the attachment site information PD12 is represented in a body coordinate system with the attachment site P11 as a root site, the position information for the attachment site P11 is not necessary and therefore the attachment site information PD12 includes position information of 5×3=15 dimensions in total. Further, the attachment site information PD12 may include the orientation information for each of the sites in the global coordinate system included in the attachment site information PD10. In such a case, the attachment site information PD12 includes orientation information of 6×4=24 dimensions in total.

FIG. 7 is an explanatory diagram that describes a second step according to the present embodiment. Because the attachment site information PD12 illustrated in FIG. 7 is similar to the attachment site information PD12 illustrated in FIG. 6, the description thereof is omitted here.

In the second step, position estimation (interpolation) for a non-attachment site is performed (S200) on the basis of the attachment site information PD12, and thereby skeleton information SD10 is obtained that includes position information for the non-attachment site to which no inertial sensor is attached, in addition to the position information for the attachment sites. In the example illustrated in FIG. 7, for example, sites SP11 and SP12 are the attachment sites and a site SP20 is the non-attachment site.

Here, the position estimation for the non-attachment site, i.e., the second step, may be performed by the inverse kinematics calculation as described above. In order to perform the position estimation for the non-attachment site with high accuracy, it is desirable that the attachment site information PD12 serving as an input thereto be obtained with high accuracy in the first step. The first step, i.e., the position estimation for the attachment sites, may be performed by an inertial navigation system, for example. However, in a case where the position estimation for the attachment sites is performed by the inertial navigation system, an error in the estimated position can become larger with time. To cope with tins, in the present embodiment, the position information for the attachment sites estimated by the inertial navigation system is corrected to thereby acquire position information for the attachment sites with higher accuracy. The correction of position information for the attachment sites according to the present embodiment is described below.

2-2. Correction of Position Information for Attachment Site

First, a description will be given of a position estimation process based on the inertial navigation system. The inertial navigation system is a technique for calculating a sensor position by performing integration (Integration) of angular velocity and acceleration a plurality of times, and is employed in, for example, vessels, aircraft, or the like. FIG. 8 is a schematic diagram illustrating an overview of the position estimation process based on the inertial navigation system.

In the inertial navigation system, first, an orientation of a sensor unit in a global coordinate system is calculated by integrating an angular velocity (an example of sensor data) in a local coordinate system acquired by a gyro sensor included in the sensor unit (S111). Next, on the basis of the orientation of the sensor unit in the global coordinate system, an acceleration (an example of sensor data) of the sensor unit in the local coordinate system (a coordinate system set for each sensor unit) acquired by an acceleration sensor included in the sensor unit is subjected to a coordinate system conversion into an acceleration of the sensor unit in the global coordinate system (S112). Then, the acceleration of the sensor unit in the global coordinate system resulting from the coordinate system conversion is integrated (S113) to thereby calculate a velocity of the sensor unit in the global coordinate system. Next, the velocity of the sensor unit in the global coordinate system is integrated (S114) to thereby calculate a moving distance of the sensor unit. Here, by combining the moving distances in the global coordinate system for each subdivision point, it is possible to obtain relative position information with respect to an initial position as a starting point. If the initial position is known, it is possible to calculate absolute position information (i.e., three-dimensional coordinates in the global coordinate system) of the sensor unit from the above information. In the above-described manner, orientation information and position information of the sensor unit are outputted by the position estimation process based on the inertial navigation system.

The position estimation process based on the inertial navigation system illustrated in FIG. 8 is performable at a relatively low process load and a high speed.

Here, in the inertial navigation system, only one integration is applied to the angular velocity in step S111 in order to obtain the orientation information, and further, it is possible to acquire the orientation information with higher accuracy by combining a well-known technique such as AHRS. On the other hand, to obtain the position information, two integrations are applied to the acceleration in step S113 and step S114. Therefore, if the acceleration acquired by the acceleration sensor includes an error, the error can be accumulated in the outputted position information, FIG. 9 is a schematic diagram illustrating a time-varying image of a position error that can occur in the position estimation process based on the inertial navigation system. As illustrated in FIG. 9, for a short period of time after the start of estimation of the position information by the inertial navigation system, the position error is small and it is thus possible to estimate the position information with high accuracy. However, the error included in the position information estimated by the inertial navigation system can increase with time as illustrated in FIG. 9, and therefore if the estimation is performed continuously for a long time, a significantly large error can be included in the position information.

To address this, in the present embodiment, position estimation for the attachment sites is performed by regression on the basis of a dynamics model (Dynamics Model). FIG. 10 is a schematic diagram illustrating an overview of a position estimation process based on the dynamics model.

The process in steps S121 and S122 illustrated in FIG. 10 is similar to the process in steps S111 and S112 described with reference to FIG. 8, and therefore the description thereof is omitted here. As illustrated in FIG. 10, in the position estimation process based on the dynamics model, position information of the sensor units is estimated by regression (S123) without performing integration of acceleration. In the regression estimation process in step S123, position information is estimated by regression where the orientations and accelerations of the sensor units in the global coordinate system are fitted to a dynamics model prepared in advance. Here, it is possible to generate the dynamics model by, for example, learning kinematic constraint information (for example, information including a plurality of samples of positions and orientations of various sites in postures or a series of motions acquired previously) in advance. It is to be noted that various regression analysis methods are usable for the regression estimation process in step S123 and, for example, methods such as DNN (Deep Neural Network) and Random Forest may be used alone or in combination.

Here, because the process illustrated in FIG. 10 involves no integration of acceleration, a position error is likely to become larger with time as with the case with the inertial navigation system described with reference to FIGS. 8 and 9. FIG. 11 is a schematic diagram illustrating a time-varying image of a position error that can occur in the position estimation process based on the dynamics model. Although a position error also occurs in the position estimation process based on the dynamics model as illustrated in FIG. 10, it does not become larger with time. Accordingly, a large error is less likely to result even if the process is performed continuously for a long time.

Therefore, it is considered that the position estimation process based on the dynamics model illustrated in FIG. 10 makes it possible to estimate position information with higher accuracy. However, because the position estimation process based on the dynamics model performs statistical estimation by regression, variations in output (estimation result) are likely to be discontinuous even in a case where variations in input are continuous. As a result, for example, the finally obtained skeleton information as visualized can tend to give rise to a sense of strangeness. Further, when compared with the position estimation process based on the inertial navigation system illustrated in FIG. 8, the position estimation process based on the dynamics model illustrated in FIG. 10 is higher in process load, which makes it difficult to achieve higher execution speed than the position estimation process based on the inertial navigation system.

As described above, the position estimation process based on the inertial navigation system and the position estimation process based on the dynamics model have their respective features. Therefore, in the present embodiment, position information is estimated with higher accuracy by combining the position estimation process based on the inertial navigation system and the position estimation process based on the dynamics model, and correcting the estimated position information. In the following, the position estimation process based on the inertial navigation system may be referred to as a first process, and the position estimation process based on the dynamics model may be referred to as a second process.

FIG. 12 is a schematic diagram illustrating an overview of a position estimation process according to the present embodiment. It is to be noted that FIG. 12 illustrates an overview, and thus the position estimation process according to the present embodiment may further include a process unillustrated in FIG. 12.

As illustrated in FIG. 12, the position estimation process according to the present embodiment includes a correction process (S130) in addition to the first process (S111 to S114) based on the inertial navigation system and the second process (S121 to S123) based on the dynamics model. In the correction process of step S130, correction is performed by referencing an output of the first process (hereinafter, also referred to as a first output) and an output of the second process (hereinafter, also referred to as a second output). It is to be noted that the first output includes orientation information and position information for the attachment sites, and the second output includes position information therefor. Then, in step S130, the position information included in the first output is corrected on the basis of the orientation information included in the first output and the position information included in the second output. Note that in step S130, the orientation information included in the first output may be used for correcting the position information and be outputted as it is. Further, the correction process in step S130 is implementable by a Kalman filter, for example.

Moreover, as described above, the first process is executable faster than the second process. Therefore, the correction process (S130) may be executed at the time when the second output is obtained and, if the second output is not obtained but only the first output is obtained, the first output may be outputted as it is as an output of the position estimation process according to the present embodiment.

FIG. 13 is a schematic diagram illustrating a time-varying image of a position error that can occur in the position estimation process according to the present embodiment. Assume that in the example illustrated in FIG. 13, the second output is obtained and correction based on the second output is performed at a time $t_{11}$. As illustrated in FIG. 13, in the position estimation process according to the present embodiment, the position error becomes larger with time during a period from the start of the process to the time $t_{11}$; however, as a result of the correction based on the second output performed at the time $t_{11}$, the position error is suppressed.

Thus, according to the position estimation process of the present embodiment, position error is suppressed every time correction is performed. Therefore, error is less likely to become larger with time, and even if the process is performed continuously for a long period of time, a large error is less likely to result. Further, in the position estimation process according to the present embodiment, the first output is outputted as it is in the case where the second output is not obtainable. This makes it possible to estimate position information more frequently as compared with a case of performing position estimation with only the second process based on the dynamics model.

3. Configuration Example

The principle of the technology according to the present embodiment has been described above. Next, a configuration example of the present embodiment will be described. In the following, a unit configuration example and a functional configuration example of the present embodiment will be described in order.

3-1. Unit Configuration Example

FIG. 14 illustrates an example of a unit configuration of a system according to the present embodiment. As illustrated in FIG. 14, the system according to the present embodiment includes the sensor units 10A to 10F, a hub unit 20, an information processor 30, and an output unit 40.

The sensor units 10 are units that each include at least a motion sensor and are to be attached to sites of a body. The sites to which the sensor units 10A to 10F are attached have been described with reference to FIG. 1, and individual descriptions will thus be omitted. For example, as illustrated in FIG. 14, the sensor units 10 each include a gyro sensor 12, an acceleration sensor 14, a controller 16, and a communicator 18. Note that the motion sensors included in the sensor units 10 are not limited to inertial sensors (the gyro sensors 12 and the acceleration sensors 14). For example, the sensor units 10 may include motion sensors such as geomagnetic sensors, barometric sensors, image sensors or the like in place of the inertial sensors or in addition to the inertial sensors. Further, while FIG. 14 illustrates the configuration of only the sensor unit 10A, the sensor units 10A to 10F may have identical configurations.

The gyro sensor 12 is an inertial sensor that acquires angular velocity as sensor data. The angular velocity acquired, by the gyro sensor 12 may be an angular velocity of the sensor unit 10 in a local coordinate system.

Further, the acceleration sensor 14 is an inertial sensor that acquires acceleration as sensor data. The acceleration acquired by the acceleration sensor 14 may be an acceleration of the sensor unit 10 in a local coordinate system that is set for each sensor unit 10.

The controller 16 controls operations of the sensor unit 10. For example, the controller 16 may control communications performed by the communicator 18 and may cause the sensor data (angular velocity, and acceleration) acquired by the gyro sensor 12 and the acceleration sensor 14 to be transmitted to the hub unit 20. Alternatively, the controller 16 may perform processing on the sensor data acquired by the gyro sensor 12 and the acceleration sensor 14, and may cause the processing results obtained through the processing to be transmitted to the hub unit 20.

The communicator 18 is a communication module for transmitting and receiving data to and from other units in a wired manner or wirelessly. The communicator 18 communicates wirelessly with external equipment directly or via a network access point in a scheme such as a wired LAN (Local Area Network), wireless LAN, Wi-Fi (registered trademark) (Wireless Fidelity), infrared communication, Bluetooth (registered trademark), short-range/contactless communication or the like, for example.

The hub unit 20 is an information processor that receives information from a plurality of sensor units 10 and aggregates the information. It is to be noted that the sensor units 10 and the hub unit 20 may be connected to each other in a wired manner or wirelessly. The huh unit 20 includes, for example, a communicator 22 and a controller 24 as illustrated in FIG. 14.

The communicator 22 is a communication module for transmitting and receiving data to and from other units in a wired manner or wirelessly. The communicator 22 communicates wirelessly with external equipment directly or via a network access point in a scheme such as a wired LAN, wireless LAN, Wi-Fi, infrared communication, Bluetooth, short-range/contactless communication or the like, for example.

The controller 24 controls operations of the hub unit 20. For example, the controller 24 may control communications performed by the communicator 22 and may cause information received from the sensor units 10 to be transmitted as it is to the information processor 30. Alternatively, the controller 24 may perform processing on the information received from the sensor units 10, and may cause the processing results obtained through the processing to be transmitted to the information processor 30.

The information processor 30 is an information processor that receives information from the hub unit 20 and processes the information. It is to be noted that the hub unit 20 and the information processor 30 may be connected to each other in a wired manner or wirelessly. The information processor 30 includes, for example, a communicator 32 and a controller 34 as illustrated in FIG. 14.

The communicator 32 is a communication module for transmitting and receiving data to and from other units in a wired manner or wirelessly. The communicator 32 communicates wirelessly with external equipment directly or via a network access point in a scheme such as a wired LAN, wireless LAN, Wi-fi, infrared communication, Bluetooth, short-range/contactless communication or the like, for example.

The controller 34 controls operations of the information processor 30. For example, the controller 34 performs processing on information received by the communicator 32. Further, the controller 34 is able to control display of the output unit 40 by controlling and causing the communicator 32 to transmit the foregoing processing results to the output unit 40 connected to the information processor 30. For example, the controller 34 may cause the output unit 40 to display visualized skeleton information, a 3-D model reflecting the skeleton information or the like on the basis of the skeleton information obtained as a result of the processing.

The output unit 40 is a unit that has at least a display function, and performs displaying in accordance with the control by the controller 34 of the information processor 30. The output unit 40 may be, for example, an installation-type display or an HMD (Head Mounted Display) to be worn by a user. Further, the output unit 40 and the information processor 30 may be an integral unit.

3-2. Functional Configuration Example

The unit configuration example of the system according to the present embodiment has been described above. Next, a functional configuration example of the system according to the present embodiment will be described. FIG. 15 illustrates an example of the functional configuration of the system according to the present embodiment. Note that FIG. 15 illustrates only the functional configuration that mainly represents the characteristics of the present embodiment, and the system according to the present embodiment may thus include a functional configuration unit lustrated in FIG. 15.

Referring to FIG. 15, the system according to the present embodiment has functions as a global motion acceleration orientation calculator 510, an integral calculator 520, a selector 530, an attachment position regression estimator 540, a reliability identifier 550, a ground contact detector 560, a corrector 570, and an interpolator 580.

It is to be noted that each functional configuration in FIG. 15 described below may be achieved by any of the units illustrated in FIG. 14. For example, the controller 16 of the sensor unit 10 or the controller 24 of the hub unit 20 may have a function as the global motion acceleration orientation calculator 510, and the controller 34 of the information processor 30 may have other functions as the integral calculator 520 to the interpolator 580. However, which unit has which function is not limited to such an example.

The global motion acceleration orientation calculator 510 has a function of performing processing on the basis of the sensor data (angular velocities and accelerations) acquired by the sensor units 10A to 10F illustrated in FIG. 14. Note that the global motion acceleration orientation calculator 510 may process pieces of the sensor data acquired respectively by the sensor units 10A to 10F independently of each other.

For example, the global motion acceleration orientation calculator 510 performs a process of integrating the angular velocities of the sensor units 10 in the local coordinate system included in the sensor data and thereby calculating orientations of the sensor units 10 in the global coordinate system (corresponding to steps S111 and S121 in FIG. 12). The global motion acceleration orientation calculator 510 may calculate the orientations of the sensor units 10 by AHRS. Note that in a case where the sensor units 10 include geomagnetic sensors, the global motion acceleration orientation calculator 510 may use sensor data acquired by the geomagnetic sensors in calculating the orientations of the sensor units 10 by AHRS.

Further, the global motion acceleration orientation calculator 510 performs a process of converting the calculated orientations of the sensor units 10 in the global coordinate system into orientation of the attachment sites to which those sensor units 10 are attached in the global coordinate system. The global motion acceleration orientation calculator 510 may convert the orientations of the sensor units 10 into the orientations of the attachment sites by using preliminary calibration results.

Further, on the basis of the orientations of the attachment sites in the global coordinate system, the global motion acceleration orientation calculator 510 performs a process of converting the accelerations in the local coordinate system included in the sensor data into accelerations in the global coordinate system (corresponding to steps S112 and S122 in FIG. 12).

Further, the global motion acceleration orientation calculator 510 performs a process of removing gravity components from the accelerations in the global coordinate system obtained as described above. For example, the global motion acceleration orientation calculator 510 may remove the gravity components from the accelerations in the global coordinate system on the basis of the orientations of the attachment sites in the global coordinate system.

The global motion acceleration orientation calculator 510 outputs the orientation information for the attachment sites in the global coordinate system obtained by the above-described process and the accelerations in the global coordinate system, from which the gravity components have been removed, to the integral calculator 520, the selector 530, and the attachment position regression estimator 540.

The integral calculator 520 calculates position information for the attachment sites in the global coordinate system by performing a process (corresponding to steps S113 and S114 in FIG. 12) of integrating twice the accelerations in the global coordinate system, from which the gravity components have been removed, inputted from the global motion acceleration orientation calculator 510. The integral calculator 520 outputs to the corrector 570 the calculated position information for the attachment sites in the global coordinate system and the orientation information for the attachment sites in the global coordinate system inputted from the global motion acceleration orientation calculator 510.

Note that the foregoing first process based on the inertial navigation system may be performed by the global motion acceleration orientation calculator 510 and the integral calculator 520 described above. Further, the position information and the orientation information outputted from the integral calculator 520 correspond to the first output.

The selector 530 selects a dynamics model for the attachment position regression estimator 540 to estimate the positions of the attachment sites by regression. For example, a plurality of dynamics models may be prepared depending on patterns of the sites to which the sensor units 10 are attached and may be stored in a memory section (not illustrated). From among such a plurality of dynamics models, the selector 530 selects a dynamics model to be used by the attachment position regression estimator 540.

The dynamics models may be prepared in advance for each combination of the attachment sites, for example. The selector 530 may select an appropriate dynamics model by identifying the combination of the attachment sites on the basis of information inputted from the global motion acceleration orientation calculator 510. Such a configuration allows the selector 530 to dynamically select an appropriate dynamics model even in a case where, for example, one or more of the sensor units 10 are detached and re-attached by the user at some point during operation of the system or power supply from batteries (not illustrated) is lost in one or more of the sensor units 10. Note that FIG. 15 illustrates an example in which the combination of the attachment sites is identified on the basis of the information inputted from the global motion acceleration orientation calculator 510; however, the selector 530 may identify the combination of the attachment sites by using the sensor data itself as an input or by using other information.

FIG. 16 is an explanatory diagram illustrating examples of combinations of the attachment sites and the dynamics models. In each of skeleton information SD101 to SD105 illustrated in FIG. 16, the attachment sites to which the sensor units 10 are attached are marked with circles. Also, different root sites may be set for different dynamics models.

For example, in the skeleton information SD101 corresponding to a whole-body model, the attachment site SP101 corresponding to the waist is the root site, and the sensor units 10 are attached to six attachment sites SP101 to SP106. In the skeleton information SD102 corresponding to an upper limb model, the attachment site SP106 corresponding to the head is the root site, and the sensor units 10 are attached to three attachment sites SP102, P105, and SP106. Further, in the skeleton information D103 corresponding to a head-to-arm model, the attachment site SP106 corresponding to the head is the root site, and the sensor units 10 are attached to two attachment sites SP102 and SP106. Further, in the skeleton information D104 corresponding to a waist-to-arm model, the attachment site SP101 corresponding to the waist is the root site, and the sensor units 10 are attached to two attachment sites SP101 and SP105. Further, in the skeleton information D105 corresponding to a lower limb model, the attachment site SP101 corresponding to the waist is the root she, and the sensor units 10 are attached to three attachment sites SP101, SP103, and SP104.

Note that not only the attachment position regression estimator 540 to be described later but also the corrector 570 and the interpolator 580 to be described later perform processes in accordance with the combination of the attachment sites, and therefore combinations of non-attachment sites to be estimated can differ depending on the combination of the attachment sites (i.e., depending on the dynamics model). Sites for which the system according to the present embodiment is able to estimate position information and orientation information may be the attachment sites, and non-attachment sites that are located between a plurality of attachment sites in a predetermined skeleton structure. In the skeleton information SD101 to SD105 in FIG. 16, indicated by hatching are the sites (including attachment sites and non-attachment sites) for which it is possible to estimate position information and orientation information in the present embodiment, in accordance with the combinations of the attachment sites.

It should be noted that FIG. 16 illustrates an example, and combinations of the attachment sites in the dynamics models usable in the present embodiment are not limited to the example illustrated in FIG. 16.

Using the dynamics model selected by the selector 530, the attachment position regression estimator 540 performs a regression estimation process (corresponding to step S123 in FIG. 12) of estimating position information for the attachment sites by regression based on the orientation information for the attachment sites in the global coordinate system and the accelerations in the global coordinate system from which the gravity components have been removed. Note that the attachment position regression estimator 540 according to the present embodiment estimates the position information for the attachment sites in a body coordinate system with reference to the root site set for each dynamics model. The attachment position regression estimator 540 outputs the estimated position information for the attachment sites in the body coordinate system to the reliability identifier 550 and the corrector 570.

Note that the foregoing second process based on the dynamics model may be performed by the global motion acceleration orientation calculator 510 and the attachment position regression estimator 540 described above. Further, the position information outputted from the attachment position regression estimator 540 corresponds to the second output.

The reliability identifier 550 has a reliability identification function of identifying reliability of the position information for the attachment sites estimated by the attachment position regression estimator 540, which will also be referred to as position information included in the second output. The reliability identified by the reliability identifier 550 may be used in corrections by the corrector 570 to be described later. For example, in a case where the reliability of the position information included in the second output is high, the corrector 570 to be described later places greater importance on (higher reliability in) the position information included in the second output than on the position information included in the first output and performs a correction; in a case where the foregoing reliability is low, the corrector 570 places greater importance on the position information included in the first output than on the position information included in the second output and performs a correction.

For example, the reliability identifier 550 may set higher reliability in a case where the position information included in the second output exhibits a narrower likelihood distribution, FIG. 17 illustrates an example of reliability identification by the reliability identifier 550. In FIG. 17, a position estimated by the attachment position regression estimator 540 and its likelihood distribution R10 are illustrated. For example, higher reliability is identified in a case where a difference between an upper limit L1 and a lower limit L2 of the likelihood distribution R10 is smaller. In the example illustrated in FIG. 17, high reliability is identified, that is, greater importance is placed on the position information included in the second output, during an interval between a time $t_{21}$ and a time $t_{22}$ and an interval between a time $t_{23}$ and a time $t_{24}$. Further, in the example illustrated in FIG. 17, low reliability is identified, that is, greater importance is placed on the position information included in the first output, during an interval between the time $t_{22}$ and the time $t_{23}$.

The reliability identifier 550 outputs the identified reliability to the corrector 570.

The ground contact detector 560 performs a process of detecting contact of a foot of the body with the ground on the basis of the sensor data (angular velocities and accelerations) acquired by the sensor units 10A to 10F. Such a configuration makes it possible for the corrector 570 described later to convert the position information in the body coordinate system estimated by the attachment position regression estimator 540 into that in the global coordinate system.

The ground contact detector 560 may detect contact with the ground in, for example, a so-called zero velocity update (ZUPT: Zero Velocity Update). It is to be noted that ZUPT is a technique of correcting position by detecting a zero-velocity state as a contact state. In a case where ZUPT is used, the function of correcting the position information by the corrector 570 to be described later is also implementable by ZUPT. Further, methods by which the ground contact detector 560 detects contact with the ground are not limited to such an example, and another technique may be used to detect contact of a foot of the body with the ground.

The corrector 570 references the first output inputted from the integral calculator 520 and the second output inputted from the attachment position regression estimator 540, and corrects the position information for the attachment sites included in the first output. Note that in the following, the function of the corrector 570 may be referred to as a correction function. By virtue of such a correction function, error is less likely to become larger with time as described with reference to FIGS. 12 and 13, and it is therefore possible to estimate position information for the attachment sites with higher accuracy.

As described above, the corrector 570 may correct the position information for the attachment sites on the basis of the reliability identified by the reliability identifier 550. Such a configuration makes it possible to estimate the position information for the attachment sites with higher accuracy.

Further, on the basis of the results of ground contact detection by the ground contact detector 560, the corrector 570 converts the position information for the attachment sites in the body coordinate system (the second output) estimated by the attachment position regression estimator 540 into position information for the attachment sites in the global coordinate system. With such a configuration, it is possible to perform correction with the coordinate systems unified into the global coordinate system.

Note that the correction function of the corrector 570 may be implemented by a Kalman filter. Furthermore, it is possible for the integration function of the integral calculator 520 described above and the correction function of the corrector 570 to be implemented in combination by a Kalman filter. Here, for example, a Kalman filter is assumed that has the velocity and position of each attachment site as an internal state. Such a Kalman fitter integrates the accelerations of the attachment sites in the global coordinate system outputted from the global motion acceleration orientation calculator 510, and thereby predicts the velocities and positions of the attachment sites. Then, such a Kalman filter is able to correct the position information by updating the internal state using the positions obtained by converting the position information included in the second output into that in the global coordinate system as an observation.

On the basis of the position information for the attachment sites corrected by the correcting function of the corrector 570, the interpolator 580 estimates position information for non-attachment sites and generates skeleton information. The interpolator 580 may estimate the position information for a non-attachment site located between a plurality of attachment sites in a predetermined skeleton structure, as has been described with reference to FIG. 16. Note that in the following, the function of interpolator 580 may be referred to as an interpolation function. Such an interpolation function is implementable by, for example, the inverse kinematics calculation described with reference to FIGS. 4 and 5.

As has been described with reference to FIGS. 4 and 5, in the inverse kinematics calculation, there are typically a plurality of solutions, and there may be a large number of solutions depending on the number of joint sites, for example. Therefore, in order to obtain more accurate skeleton information, a mechanism is desired that makes it possible to identify a more appropriate solution from among a large number of solutions present. Thus, the interpolator 580 according to the present embodiment estimates the position information for the non-attachment sites by regression with fitting to an inverse kinematics model prepared in advance.

Here, it is possible to generate the inverse kinematics model by, for example, teaming kinematic constraint information (e.g., information including a plurality of samples of positions and orientations of various sites in postures or a series of motions acquired previously) in advance. It should be noted that various regression analysis methods are usable for the interpolation function of the interpolator 580 and, for example, methods such as DNN and Random Forest may be used alone or in combination.

Note that although it is described above that the interpolator 580 estimates position information for each site, the present embodiment is not limited to such an example. If either one of the position information and the orientation information for each site is obtained, the other is identifiable in accordance with the skeleton structure. Therefore, the interpolator 580 only has to estimate at least one of the position information or the orientation information for the non-attachment sites.

4. Operation Example

The unit configuration example and the functional configuration example of the present embodiment have been described above. Next, an operation example of the present embodiment will be described. FIG. 18 is a flowchart illustrating an operation example of the system according to the present embodiment. Note that FIG. 18 illustrates only processes that mainly represent the characteristics of the present embodiment, and the system according to the present embodiment may thus execute a process unillustrated in FIG. 18.

As illustrated in FIG. 18, first, the global motion acceleration orientation calculator 510 calculates the orientations of the sensor units 10 in the global coordinate system (S502) by AHRS on the basis on the angular velocities acquired by the gyro sensors 12. Note that step S502 corresponds to steps S111 and S121 in FIG. 12.

Subsequently, the global motion acceleration orientation calculator 510 converts the orientations of the sensor units 10 in the global coordinate system obtained in step S502 into orientations of the attachment sites to which those sensor units 10 are attached in the global coordinate system (S504).

Subsequently, the global motion acceleration orientation calculator 510 converts the accelerations in the local coordinate system acquired by the acceleration sensors 14 into acceleration in the global coordinate system (S506) on the basis of the orientations of the attachment sites in the global coordinate system obtained in step S504. Note that step S506 corresponds to steps S112 and S122 in FIG. 12.

Subsequently, the global motion acceleration orientation calculator 510 removes gravity components from the accelerations in the global coordinate system (S508) obtained in step S506 on the basis of the orientations of the attachment sites in the global coordinate system obtained in step S504.

Subsequently, the integral calculator 520 calculates the position information for the attachment sites in the global coordinate system by integrating twice the accelerations in the global coordinate system (S510), from which the gravity components are removed, obtained in step S508. Note that step S510 corresponds to steps S113 and S114 in FIG. 12.

Subsequently, whether or not to perform correction of step S510 is determined (S512). As described above, the position estimation process based on the dynamics model is higher in process load than the position estimation process based on the inertial navigation system. Accordingly, the execution frequency of the position estimation process based on the dynamics model (S514) is less than that of the position estimation process based on the inertial navigation system (S502 to S510). Thus, in step S512, it may be determined that correction is to be performed once every time the process illustrated in FIG. 18 is performed a predetermined number of times. However, the present embodiment is not limited to such an example. For example, in a case where it is determinable that the attachment sites are not stationary on the basis of the sensor data, it may be determined that correction is to be performed, whereas in a case where it is determinable that the attachment sites are stationary, it may be determined that correction is not to be performed.

In the case where it is determined that correction is to be performed (YES in S512), the attachment position regression estimator 540 estimates position information for the attachment sites in the body coordinate system by regression estimation using a dynamics model (S514). Note that step S514 corresponds to step S123 of FIG. 12.

Subsequently, the corrector 570 converts the position information for the attachment sites in the body coordinate system estimated in step S514 into position information for the attachment sites in the global coordinate system (S516) on the basis of the result of ground contact detection by the ground contact detector 560.

Then, on the basis of the position information for the attachment sites in the global coordinate system obtained in step S516, the corrector 570 corrects the position information for the attachment sites in the global coordinate system (S518) obtained in step S510.

Subsequently, the interpolator 580 estimates (interpolates) position information for the non-attachment sites (S520) by regression with fitting to an inverse kinematics model on the basis of the position information for the attachment sites in the global coordinate system. Note that the position information for the attachment sites used for the regression estimation of the position information for the non-attachment sites in step S520 may differ depending on the determination result in step S512. In the case where it is determined in step S512 that correction is to be performed, the position information for the attachment sites corrected in step S518 is used for the regression estimation in step S520, Meanwhile, in the case where it is determined in step S512 that correction is not to be performed, the position information for the attachment sites in the global coordinate system obtained in step S510 is used for the regression estimation in step S520.

The operation of the system according to the present embodiment has been described above. It is to be noted that the processing illustrated in FIG. 18 may be repeatedly executed each time sensor data is acquired by the gyro sensor 12 and the acceleration sensor 14, or at a predetermined frequency.

5. Modification Examples

One embodiment of the present disclosure has been described above. In the following, some modification examples of the present embodiment will be described. Note that the modification examples described below may be applied to the present embodiment singly or in combination. Further, each of the modification example may be applied in place of or in addition to the configuration described in the present embodiment.

5-1. First Modification Example

For the foregoing embodiment, an example has been described in which the attachment position regression estimator 540 performs the regression estimation process on the basis of the orientation information for the attachment sites in the global coordinate system calculated by the global motion acceleration orientation calculator 510 and the accelerations in the global coordinate system from which the gravity components have been removed. However, the present technology is not limited to such an example. For example, angular velocities and accelerations acquired by the gyro sensors 12 and the acceleration sensors 14 may be used as inputs to such a regression estimation process. Such an example will be described as a first modification example.

FIG. 19 illustrates a functional configuration example of a system according to the first modification example. Of the configuration illustrated in FIG. 19, components substantially the same as those illustrated in FIG. 15 are denoted by the same reference signs, and description thereof will thus be omitted here. A description will be given below of points different from the system illustrated in FIG. 15. Referring to FIG. 19, the system according to the present modification example differs from the system illustrated in FIG. 15 in that it includes an attachment position regression estimator 541 in place of the attachment position regression estimator 540.

The attachment position regression estimator 541 according to the present modification example performs the regression estimation process using angular velocities and accelerations acquired by the gyro sensors 12 and the acceleration sensors 14 as inputs, in addition to or in place of the information calculated by the global motion acceleration orientation calculator 510, A dynamics model to be used for such regression estimation may be prepared in advance by learning kinematic constraint information including the same kind of information (angular velocity and acceleration) as the information used for the regression estimation.

The first modification example has been described above. According to the present modification example, using more information makes it possible to estimate the position information for the attachment sites with higher accuracy. Note that the above description deals with an example in which the angular velocity and acceleration are used as inputs to the regression estimation process by the attachment position regression estimator 541; however, other information may further be used as inputs. For example, in a case where the sensor units 10 include geomagnetic sensors or barometric sensors in addition to the gyro sensors 12 and the acceleration sensors 14, information about geomagnetism or barometric pressure may be used as inputs to such a regression estimation process.

5-2. Second Modification Example

Next, an example in which a corrector identifies reliability will be described as a second modification example. FIG. 20 illustrates a functional configuration example of a system according to the present modification example. Of the configuration illustrated in FIG. 20, components substantially the same as those illustrated in FIG. 15 are denoted by the same reference signs, and description thereof will thus be omitted here. A description will be given below of points different from the system illustrated in FIG. 15, Referring to FIG. 20, the system according to the present modification example differs from the system illustrated in FIG. 15 in that it includes a corrector 572 in place of the reliability identifier 550 and the corrector 570.

The corrector 572 has, in addition to the function of the corrector 570 described with reference to FIG. 15, a function of identifying reliability of either the position information for the attachment sites inputted from the integral calculator 520 or that inputted from the attachment position regression estimator 540, or both. For example, such a function may be implemented by a Kalman filter, may be implemented to be performed on the basis of a rule determined in advance, or may be implemented by regression estimation using a model prepared in advance by learning.

5-3. Third Modification Example

Next, an example in which a correction process is performed after the position estimation (interpolation) process for the non-attachment sites will be described as a third modification example. FIG. 21 illustrates a functional configuration example of a system according to the present modification example. Of the configuration illustrated in FIG. 21, components substantially the same as those illustrated in FIG. 15 are denoted by the same reference signs, and description thereof will thus be omitted here. A description will be given below of points different from the system illustrated in FIG. 15. Referring to FIG. 21, the system according to the present modification example differs from the system illustrated in FIG. 15 in that it includes a corrector 573 and an interpolator 583 in place of the reliability identifier 550, the corrector 570, and the interpolator 580.

The interpolator 583 according to the present modification example estimates either position information or orientation information, or both, for the non-attachment sites by regression on the basis of the orientation information for the attachment sites in the global coordinate system calculated by the global motion acceleration orientation calculator 510 and the position information for the attachment sites estimated by the attachment position regression estimator 540. Note that the regression estimation by the interpolator 583 may be similar to the regression estimation for the non-attachment sites by the interpolator 580 except that information to be inputted is different. The position information or the orientation information for the non-attachment sites estimated by the interpolator 583 is outputted to the corrector 573.

It is to be noted that the second process according to the present modification example includes an interpolation process of estimating, by the foregoing interpolator 583, either position information or orientation information, or both, for the non-attachment sites. Then, the second output (the output of the second process) according to the present modification example includes either the position information or the orientation information, or both, for the non-attachment sites estimated by the interpolator 583. Further, the second output according to the present modification example may include the position information or the orientation information for the attachment sites obtained by the global motion acceleration orientation calculator 510 or the attachment position regression estimator 540. That is, the second output according to the present modification example includes either the position information or the orientation information, or both, for all the sites targeted for estimation.

On the basis of the first output (the orientation information and the position information for the attachment sites) inputted from integral calculator 520, the corrector 573 according to the present modification example corrects either the position information or the orientation information, or both, for the non-attachment sites included in the second output that is inputted from the interpolator 583. In the present modification example, the velocities and positions of the attachment sites and the positions or orientations of the non-attachment sites have a nonlinear relationship, and therefore the correction function of the corrector 573 according to the present modification example may be implemented by, for example, an extended Kalman filter. In the following, an example will be described in which a correction function of correcting the orientation information for the non-attachment sites is implemented by the extended Kalman filter.

Such an extended Kalman filter has, as an internal state, velocities and positions of all the attachment sites and orientations of all the sites (including the attachment sites and the non-attachment sites) targeted for estimation. Such an extended Kalman filter predicts the velocities and positions of the attachment sites by integrating the accelerations of the attachment sites in the global coordinate system outputted from the global motion acceleration orientation calculator 510. Then, the extended Kalman filter updates the internal state by using the orientation information for all the sites targeted for estimation included in the second output as an observation, thereby being able to correct the orientation information. It is to be noted that a covariance matrix of an error that the extended Kalman filter internally has may be predicted by using a Jacobian that describes the relationship between the velocities of the attachment sites and the orientations of the non-attachment sites used in the inverse kinematics calculation.

Note that FIG. 21 illustrates the attachment position regression estimator 540 and the interpolator 583 as separate functional configurations; however, the functions of the attachment position regression estimator 540 and the interpolator 583 may be unified. In such a case, position information and orientation information for all the sites targeted for estimation may be directly estimated by regression based on the information inputted from the global motion acceleration orientation calculator 510. In such a case, there is an effect that the number of models to be prepared in advance for the regression estimation is reduced.

5-4. Fourth Modification Example

In the foregoing embodiment, an example in which the attachment position regression estimator 540 performs regression estimation using a non-tracking-type dynamics model has been described; however, a tracking-type dynamics model may be used. In the following, an overview of the non-tracking-type dynamics model and the tracking-type dynamics model will be described with reference to FIGS. 22 and 23.

FIG. 22 is an explanatory diagram that describes an overview of the non-tracking-type dynamics model. As illustrated in FIG. 22, in the regression estimation using the non-tracking-type dynamics model, information about acceleration and orientation is inputted to allow position information to be outputted.

FIG. 23 is an explanatory diagram that describes an overview of the tracking-type dynamics model. As illustrated in FIG. 23, also in the regression estimation using the tracking-type dynamics model, information about acceleration and orientation is inputted to allow position information to be outputted. However, in the regression estimation using the tracking-type dynamics model, position information delayed by one sample by a delayer D (i.e., the output of a previous regression estimation process) is inputted to a next regression estimation process in addition to the information about acceleration and orientation. The tracking-type dynamics model has an advantage that the tracking ability is improvable.

An example in which position information for the attachment sites is estimated by regression using such a tracking-type dynamics model will be described as a fourth embodiment. FIG. 24 illustrates a functional configuration example of a system according to the present modification example. Of the configuration illustrated in FIG. 24, components substantially the same as those illustrated in FIG. 15 are denoted by the same reference signs, and description thereof will thus be omitted here. A description will be given below of points different from the system illustrated in FIG. 15. Referring to FIG. 24, the system, according to the present modification example differs from the system illustrated in FIG. 24 in that it includes an attachment position regression estimator 544 and a corrector 574 in place of the attachment position regression estimator 540 and the corrector 570.

The attachment position regression estimator 544 performs the regression estimation process by using, as an input, position information for the attachment sites that is corrected by the corrector 574 by using position information for the attachment sites estimated in a previous regression estimation process, in addition to the information calculated by the global motion acceleration orientation calculator 510. The dynamics model used for such regression estimation is the tracking-type dynamics model described above, and may be prepared in advance by learning kinematic constraint information including position information delayed by one sample, for example.

The fourth modification example described above provides improved capability of tracking various motions, thus making it possible to estimate position information for the attachment sites with higher accuracy.

5-5. Fifth Modification Example

In the foregoing embodiment, a unit configuration example has been described with reference to FIG. 14; however, the present technology is not limited to such an example. In the following, a unit configuration example of a system that does not include the hub unit 20 will be described as a fifth modification example. FIG. 25 illustrates a unit configuration example of a system according to the present modification example.

As illustrated in FIG. 25, the system according to the present modification example includes the sensor units 10A to 10F, the information processor 30, and the output unit 40. As illustrated in FIG. 25, in the present modification example, the sensor units 10 are directly connected to the information processor 30 without the hub unit 20 therebetween. It is to be noted that the sensor units 10 and the information processor 30 may be connected to each other in a wired manner or wirelessly. Except for such a connection relationship, each of the units illustrated in FIG. 25 may have a similar configuration to that of a corresponding unit denoted by the same reference sign in FIG. 14.

5-6. Sixth Modification Example

In the foregoing embodiment, an example in which regression estimation is performed using a dynamics model and an inverse kinematics model has been described. The estimation result of this regression estimation can vary greatly depending on the kinematic constraint information used for learning to generate the dynamics model and the inverse kinematics model. For example, in a case where kinematic constraint information obtained by sensing a characteristic posture or motion is used for learning, the estimation result tends to have a characteristic closer to the motion used for learning than to the actual motion of the body.

Examples of the characteristic posture or motion include, but are not limited to, postures unique to characters such as zombies, dynamic motions typical of fighting scenes, postures frequently appearing in games such as shooting games, choreographed motions characteristic of each genre of dance, motions based on individual rules of each sport, etc.

By appropriately preparing the kinematic constraint information as described above to suit the application and using it for learning to generate a dynamics model and an inverse kinematics model, it is possible to estimate skeleton information appropriate to the application. As a result, for example, in a case of producing an animation on the basis of skeleton information, it is possible to produce a characteristic animation without involving postprocessing on the skeleton information estimated through the series of processes described above.

6. Overview of Second Embodiments

6-1. Regarding Overview of Present Embodiment

Incidentally, the motion capture technique according to the foregoing first embodiment of the present disclosure makes it possible to obtain attachment positions of the sensor units with high accuracy while suppressing an increase in the number of the sensor units 10 to be attached to the user (actor, performer). Furthermore, this motion capture technique is low in process load and therefore suitable for capturing motions (movements and orientations) of a plurality of users in real time.

In addition, for example, in visualizing the user's motions in an avatar on a virtual space, not only real-time reproduction of the captured motions of the user is desired but also, in a performance in a live show or the like, minimal expressions may be desired of the avatar for achieving an effective presentation.

Accordingly, in view of the above-described situation, the present inventors have created a method of blending motions of a plurality of users captured by using the motion capture technique according to the foregoing first embodiment of the present disclosure and reproducing the blended motions in real time in an avatar or the like on a virtual space. The foregoing method created by the present inventors will be described below as a second embodiment of the present disclosure. First, with reference to FIG. 26, an overview of the second embodiment of the present disclosure will be described. FIG. 26 is an explanatory diagram that describes the overview of the present embodiment.

Specifically, in the present embodiment, for example, as illustrated in FIG. 26, motions (movements and orientations) of a plurality of performers (performer 1 and performer 2 in FIG. 26) (actors) doing a performance (such as a dance) on the stage are captured by the motion capture technique according to the first embodiment of the present disclosure described above. Further, in the present embodiment, the captured motions of the plurality of performers are blended on the basis of a predetermined algorithm, and the blended motions are reproduced in real time in an avatar or the like on a virtual space.

Note that in the present embodiment, what reproduces the blended motions may be an avatar (not limited to a human-shaped one) on a virtual space, i.e., an animation, or a robot on a real space, and is not specifically limited.

Further, in the present embodiment, the subject of motion capture (the actor) is not limited to a performer (for example, a dancer, a singer, or the like) who does a performance (such as a dance) on the stage, and may be the audience who enjoy the performance. Further, in the present embodiment, the actor is not limited to a human, and may be, for example, an animal, or an animation prepared in advance in which a human character or the like makes a motion, and there is no specific limitation. The details of the second embodiment of the present disclosure will be described below in order.

6-2. Functional Configuration Example

Next, a system functional configuration according to the second embodiment wall be described with reference to FIG. 27. FIG. 27 illustrates an example of the functional configuration of the system according to the present embodiment. Note that FIG. 27 illustrates only the functional configuration that mainly represents the characteristics of the present embodiment, and the system according to the present embodiment may include the functional configuration illustrated in FIG. 15.

The controller 34 of the information processor 30 of the system according to the present embodiment is able to dynamically control the motion of an avatar in a virtual space or a robot on a real space. Referring to FIG. 27, the controller 34 has functions as an information acquirer 610, a blending ratio determinator 620, a blender 630, and an operation controller 640. Further, each functional configuration of FIG. 27 described below may be implemented by any of the units illustrated in FIG. 14, and is not particularly limited.

Specifically, the information acquirer 610 captures a motion corresponding to at least one site of each of a plurality of performers (users, actors) on a real space by using the sensor units (motion sensors) 10 attached to the plurality of performers. More specifically, as described in the foregoing embodiment, for example, the information acquirer 610 uses each of a plurality of sensor units 10 attached to six sites of the body of the performer to capture the motion of each of the sites of the performer. That is, the information acquirer 610 is able to acquire the skeleton information of the foregoing first embodiment. Then, the information acquirer 610 outputs the acquired information to the blender 630 described later.

Note that in the present embodiment, the above-described sites are parts of the body of the performer, and specifically represent the upper body, the lower body, the head, a joint, the waist, a wrist, an ankle, etc. of the performer.

The blending ratio determinator 620 determines a blending ratio (weighting) dynamically applied to the motions of the sites of each performer. Then, the blending ratio determinator 620 outputs the determined blending ratio to the blender 630 described later. Here, the blending ratio refers to a mixture ratio of the motions of the sites of different performers in a motion reproduced in the avatar or the like. Note that the details of a method of determining the blending ratio will be described later.

The blender 630 blends the motions of the sites of the performers on the basis of the blending ratio determined by the blending ratio determinator 620 described above. Then, the blender 630 outputs information regarding the blended motions to the operation controller 640 described later.

The operation controller 640 dynamically controls the motion of the avatar or the robot on the basis of the information regarding the blended motions (the blend result) to cause the avatar or the robot to make a motion reflecting the motions of the sites of the plurality of performers. That is, the operation controller 640 is able to control the output unit 40 in order to dynamically control the motion of the avatar or the robot.

6-3. Operation Example

The functional configuration example according to the present embodiment has been described above. Next, an operation example (an information processing method) according to the present embodiment will be described with reference to FIGS. 28 and 29. FIG. 28 is a flowchart illustrating an operation example of the system according to the present embodiment. Note that FIG. 28 illustrates only processes that mainly represent the characteristics of the present embodiment, and the system according to the present embodiment may thus execute a process unillustrated in FIG. 28. Further, FIG. 29 is a flowchart that describes an operation in step S200 of FIG. 28.

Specifically, the system according to the present embodiment dynamically controls the motion of the avatar or the robot in generally three steps as illustrated in FIG. 28. Specifically, in the present embodiment, first, a blending ratio (weighting) for a motion of a site of each performer or a determination method for the blending ratio is set in advance (S100). Next, in the present embodiment, in order to reproduce the motion of the avatar or the like, the motion of the site of each performer is captured on the basis of setting conditions set in step S100 described above, and a process of blending the motions of the sites of the performers is executed for each frame (S200). Further, in the present embodiment, the avatar is drawn (S300) on the basis of the result of the process of step S200 described above. Note that in a case of a robot, for example, the operation of the robot is controlled in the present embodiment.

More specifically, in the present embodiment, the orientation (θ) and the position (P) of a site (a joint) of the avatar or the like are expressible by the following equations (3) with the blending ratios α and β. Note that the following equations (3) represent a case of blending the motions of the sites of two performers.

[Math. 2]

$$\theta[n] = \alpha_1 \times \theta_1[n] + \alpha_2 \times \theta_2[n]$$

$$P[n] = \beta_1 \times P_1[n] + \beta_2 \times P_2[n] \quad (3)$$

θ[n]: Orientation of n-th joint of avatar $\theta_1[n], \theta_2[n]$: Orientations of n-th joints of performers 1 and 2

P[n]: Position of n-th joint of avatar $P_1[n], P_2[n]$: Positions of n-th joints of performers 1 and 2

It is to be noted that in view of correlation, the blending ratios α and β preferably satisfy the following equations (4). Note that the details of the determination method for the blending ratio will be described later.

[Math. 3]

$$1 = \alpha_1 + \alpha_2$$

$$\beta_1 = \alpha_1$$

$$\beta_2 = \alpha_2 \quad (4)$$

Further, in a case where, for example, the blending ratios $\alpha_1$ and $\beta_2$ become zero in the site motions of the two performers, the system according to the present embodiment stops calculations of the orientations (θ) and positions (P) of the sites of the avatar or the like. Further, in a case where the foregoing blending ratios $\alpha_1$ and $\beta_2$ become other than zero, the system according to the present embodiment restarts calculating the orientations (θ) and positions (P) of the sties of the avatar or the like. In the present embodiment, this makes it possible to reduce load of the process relating to the calculations of the orientations (θ) and positions (P) of the sties of the avatar or the like.

Further, in the present embodiment, the process load in the system according to the present embodiment may be reduced in the following manner. For example, suppose that in a case where the blending ratio is to be set by an operator in advance, the operator makes settings to cause the upper body of the avatar or the like to reproduce a blend of the motions of the upper bodies of performer 1 and performer 2 and to cause the lower body of the avatar or the like to reproduce only the motion of the lower body of performer 1. In such a case, in the present embodiment, stopping the motion capture of the lower body of performer 2 makes it possible to reduce the process load in the system according to the present embodiment.

Note that the present embodiment is not limited to blending the motions of sites of two performers, and the motions of sites of M performers may be blended. In such a case, the orientation (θ) and the position (P) of a site (a joint) of the avatar or the like are expressible by the following equations (5) and (6) with the blending ratios α and β.

[Math. 4]

$$\theta[n] = \alpha_1 \times \theta_1[n] + \alpha_2 \times \theta_2[n] + \alpha_3 \times \theta_3[n] + \ldots + \alpha_M \times \theta_M[n]$$

$$P[n] = \beta_1 \times P_1[n] + \beta_2 \times P_2[n] + \beta_3 \times P_3[n] + \ldots + \beta_M \times P_M[n] \quad (5)$$

θ[n]: Orientation of n-th joint of avatar
θ$_1$[n], θ$_2$[n], ... θ$_M$[n]: Orientation of n-th joint of performer m
P[n]: Position of n-th joint of avatar
P$_1$[n], P$_2$[n], ... P$_M$[n]: Position of n-th joint of performer m

[Math. 5]

$$\theta[n]=\alpha_1(t)\times\theta_1[n]+\alpha_2(t)\times\theta_2[n]$$

$$P[n]=\beta_1(t)\times P_1[n]+\beta_2(t)\times P_2[n] \quad (6)$$

Further, in the present embodiment, the blending ratios α and β may not be of fixed values but may be of, for example, values that vary dynamically with time. In such a case, the orientation (θ) and the position (P) of a site (a joint) of the avatar or the like are expressible by the following equations (7) with the blending ratios α and β.

[Math. 6]

$$\theta[n]=\alpha_1(t)\times\theta_1[n]+\alpha_2(t)\times\theta_2[n]$$

$$P[n]=\beta_1(t)\times P_1[n]+\beta_2(t)\times P_2[n] \quad (7)$$

Next, the details of step S200 in FIG. 28 of determining the blending ratio and determining the motion of the avatar or the like will be described with reference to FIG. 29. Specifically, the system according to the present embodiment captures motions of the sites of each of the performers and, on the basis of the captured information, calculates various factors (distance, acceleration, etc.) for determining the blending ratio (S201). Next, the system calculates a temporary single blending ratio (α_temp) for each of the performers on the basis of the foregoing factors (S203). Further, on the basis of the temporary single blending ratio (α_temp) calculated for each of the performers, the system calculates a final blending ratio α in consideration of correlation (S205). Then, the system performs a process of blending the motions of the sites of the performers on the basis of the final blending ratio α, and generates an animation of the avatar for reproduction (S207).

Note that in the present embodiment, as described above, what reproduces the blended motions may be an avatar on a virtual space or a robot on a real space, and is not specifically limited. In addition, in a case of using an avatar, the avatar may be either human-shaped or animal-shaped, and may be represented in a manner in which every several-minute-old motions are overlaid and displayed (for example, in a particle display or the like).

In the present embodiment, various examples are listable for the method of determining the blending ratio α. A description will thus be given of some examples of the method of determining the blending ratio α below. Note that the present embodiment is not limited to the following methods of determining the blending ratio α.

6-4. Example 1 of Blending Ratio Determination Method

An algorithm according to a blending ratio determination method in example 1 of the blending ratio determination method dynamically determines the blending ratio α applied to the motion of a site of each of performers in accordance with a distance from a reference point that is set in advance on a real space to the performer, and blends the motions of the sites of the performers on the basis of the determined blending ratios α. Details of such example 1 of the blending ratio determination method will be described with reference to FIGS. 30 to 32. FIG. 30 is an image diagram that describes an overview of example 1 of the blending ratio determination method according to the present embodiment. FIGS. 31 and 32 are image diagrams that describes an operation of example 1 of the blending ratio determination method according to the present embodiment.

For example, in this method, assumed is a case of causing the avatar's motion to approach the motion of a performer moving to the center of the stage of a dance battle or the like, or a case of causing the avatar's motion to approach the motion of a member of an idol group who stands at the center of the stage when the group changes formation (arrangement) of the members while singing in its live show.

(Preliminary Preparation)

For example, in this method, as illustrated in FIG. 30, a reference point C on a stage (for example, the center point of the stage) on a real space is set in advance. Further, in this method, as illustrated in FIG. 31, a minimum distance d_min and a maximum distance d_max from the reference point C on the stage on the real space are set in advance. Specifically, it is possible for the minimum distance d_min to be set with reference to the step length or the like of the performer and, for example, to be set to about 1 m. It is possible for the minimum distance d_max to be set with reference to the size of the stage or the like and, for example, to be set to about 10 m. Then, in this method, as illustrated in FIG. 31, for example, in a case where the distance from the reference point C to a performer is the minimum distance d_min, the temporary single blending ratio α_temp to be applied to the motion of the performer may be set to 1, and in a case where the distance from the reference point C to a performer is the maximum distance d_max, the temporary single blending ratio α_temp to be applied to the motion of the performer may be set to 0.

(Frame Process)

For example, in this method, distances d_n from the reference point C to all the performers are obtained. It should be noted that while there is no specific limitation, it is possible to obtain the distances d using the foregoing sensor units 10, imaging units, positioning sensors (for example, incorporated in the sensor units 10) attached to the performers, a pressure sensor provided on the stage, or the like. Note that the positioning sensors may be, for example, GNSS (Global Navigation Satellite System) receivers or the like. In this case, the positioning sensors are able to generate sensing data indicating latitudes and longitudes of the current locations of the performers on the basis of signals from GNSS satellites. Further, in this method, the relative positional relationship between the performers is detectable from, for example, RFID (Radio Frequency Identification), an access point of Wi-Fi, information from a radio base station, or the like, and therefore such a communication unit is also usable as the foregoing positioning sensors.

Further, in this method, on the basis of the obtained distance d, a temporary single blending ratio α_temp_n to be applied to the motion of the performer is calculated with reference to the graph illustrated in FIG. 32. A formula for the calculation is expressible by, for example, the following equations (8).

[Math. 7]

$$\alpha\_temp\_1 = \mathrm{Map}(d\_1, d\_\min, d\_\max, 1, 0, \mathrm{true})$$

$$\alpha\_temp\_n = \mathrm{Map}(d\_n, d\_\min, d\_\max, 1, 0, \mathrm{true}) \quad (8)$$

In this method, in a case where the distance n falls outside the range from the minimum distance d_min to the maximum distance d_max, the temporary single blending ratio $\alpha\_temp\_n$ is assumed to be 1 or 0, as illustrated in FIG. 32.

Then, in this method, in a case where the calculated single blending ratios $\alpha\_temp\_n$ are all zero, the display of the avatar or the like is stopped. On the other hand, in this method, in a case where the calculated single blending ratios $\alpha\_temp\_n$ are not all zero, respective final blending ratios $\alpha_n$ are calculated in consideration of correlation on the basis of the calculated single blending ratios $\alpha\_temp\_n$. More specifically, in this method, the respective final blending ratios $\alpha_n$ are calculated on the basis of the following equations (9).

[Math. 8]

$$\alpha\_total = \Sigma \alpha\_temp$$

$$\alpha_1 = \alpha\_temp\_1 / \alpha\_total$$

$$\alpha_n = \alpha\_temp\_n / \alpha\_total \quad (9)$$

Further, in this method, on the basis of the calculated respective final blending ratios $\alpha_n$, the process of blending motions of the sites of the respective performers is performed with reference to the foregoing equations (5) or the like.

6-5. Example 2 of Blending Ratio Determination Method

An algorithm according to a blending ratio determination method in example 2 of the blending ratio determination method dynamically determines the blending ratio $\alpha$ applied to the motion of a site of each of performers in accordance with the acceleration, velocity, or displacement amount of the site of the performer on a real space, and blends the motions of the sites of the performers on the basis of the determined blending ratios $\alpha$. Details of such example 2 of the blending ratio determination method will be described with reference to FIG. 33. FIG. 33 is an image diagram that describes an operation of example 2 of the blending ratio determination method according to the present embodiment.

For example, in this method, assumed is a case of causing the avatar's motion to approach the motion of a performer who makes vigorous movements on the stage of a dance battle or the like. That is, a description will be given below of an example in which the blending ratio $\alpha$ is dynamically determined in accordance with the acceleration of a predetermined site of the performer. However, in this method, acceleration is a non-limiting example, and the blending ratio $\alpha$ may thus be dynamically determined in accordance with the velocity or displacement amount of a predetermined site of the performer, (Preliminary Preparation)

For example, in this method, a minimum acceleration f_min and a maximum acceleration f_max are set in advance. Then, in this method, for example, in a case where the acceleration f of a predetermined site of a performer is the minimum acceleration f_min, the temporary single blending ratio $\alpha\_temp$ to be applied to the motion of the site of the performer may be set to 0, and in a case where the acceleration f of a predetermined site of a performer is the maximum acceleration f_max, the temporary single blending ratio $\alpha\_temp$ to be applied to the motion of the site of the performer may be set to 1, (Frame Process)

For example, in this method, accelerations f of the sites of all the performers are obtained. It should be noted that while there is no specific limitation, it is possible to obtain the accelerations f by using the foregoing sensor units 10 or the like. Further, in this method, on the basis of the obtained acceleration f, a temporary single blending ratio $\alpha\_temp\_n$ to be applied to the motion of the performer is calculated with reference to the graph illustrated in FIG. 33. A formula for the calculation is expressible by, for example, the following equations (10). Note that in equations (10), a maximum value of the accelerations of 17 joints (0 to 16) of one performer is taken as the acceleration f of the performer.

[Math. 9]

$$\begin{bmatrix} f1 = \max([a1[0]], [a1[1]], \ldots [a1[16]]) \\ \alpha\_temp\_1 = \text{Map} \ (f1, f\_min, f\_max, 0, 1, \text{true}) \end{bmatrix}$$

$$\begin{bmatrix} f2 = \max([a2[0]], [a2[1]], \ldots [a2[16]]) \\ \alpha\_temp\_2 = \text{Map} \ (f2, f\_min, f\_max, 0, 1, \text{true}) \end{bmatrix}$$

$$\vdots$$

$$\begin{bmatrix} fn = \max([an[0]], [an[1]], \ldots [an[16]]) \\ \alpha\_temp\_n = \text{Map} \ (fn, f\_min, f\_max, 0, 1, \text{true}) \end{bmatrix} \quad (10)$$

Note that in this method, in a case where the acceleration fn fails outside the range from the minimum acceleration f_min to the maximum acceleration f_max, the temporary single blending ratio $\alpha\_temp\_n$ is assumed to be 1 or 0, as illustrated in FIG. 33.

It should be noted that in the above description, the maximum value of the accelerations of 17 joints of one performer is assumed as the acceleration f of the performer; however, this is non-limiting in this method, and the acceleration f may be an acceleration of a predetermined site or an average value of accelerations of a plurality of sites.

Then, in this method, in a case where the calculated single blending ratios $\alpha\_temp\_n$ are all zero, the display of the avatar or the like is stopped. On the other hand, in this method, in a case where the calculated single blending ratios $\alpha\_temp\_n$ are not ail zero, respective final blending ratios $\alpha_n$ are calculated in consideration of correlation on the basis of the calculated single blending ratios $\alpha\_temp\_n$. More specifically, also in this method, the respective final blending ratios $\alpha_n$ are calculated on the basis of the foregoing equations (9).

Further, in this method, on the basis of the calculated respective final blending ratios $\alpha_n$, the process of blending motions of the sites of the respective performers is performed with reference to the foregoing equations (5) or the like.

6-6. Example 3 of Blending Ratio Determination Method

In example 3 of the blending ratio determination method described below, the blending ratio may be determined in accordance with motion synchronousness between the audience who enjoy the performance of the performers, instead of the performers on the stage. That is, an algorithm according to a blending ratio determination method in example 3 of the blending ratio determination method dynamically determines the blending ratios $\alpha$ applied to the motions of sites of two performers in accordance with motion synchronousness between the audience on a real space, and blends the motions of the sites of the respective performers on the basis of the determined blending ratios $\alpha$. Details of such example 3 of the blending ratio determination method will be described with reference to FIG. 34. FIG. 34 is an image diagram that describes an overview of example 3 of the blending ratio determination method according to the present embodiment.

For example, in this method, accelerations a of the sites of ail the audience are obtained. It should be noted that while there is no specific limitation, it is possible to obtain the accelerations a by having the audience to wear the foregoing sensor units 10 or the like on their body parts. Then, in this method, after obtaining the accelerations a of the sites of ail the audience, each of the accelerations a is integrated to be converted into velocity, and an average value $V_y$ of y components of the velocities is calculated by the following equation (11).

[Math. 10]

$$V_y = [(\int a_1 dt)y + (\int a_2 dt)y + \ldots + (\int a_N dt)y]/N \tag{11}$$

Further, in this method, the final blending ratio α is calculated on the basis of the calculated average value $V_y$ of the y components of the velocities. Note that in the present method, it is possible to experimentally determine in advance a correlation between the average value $V_y$ of the y components of the velocities and the final blending ratio α. Then, also in the present method, the process of blending the motions of the sites of the performers is performed with reference to the foregoing equations (3), (4), etc. on the basis of the calculated final blending ratio.

More specifically, for example, in a case where the jumps of the audience are synchronous in timing, as illustrated in the left side of FIG. 34, the average value $V_y$ of the y components of the velocities becomes large in amplitude, and the final blending ratio α varies largely. As a result, the avatar's motion largely switches between performer 1 and performer 2, and thus comes into a dynamic state.

Further, for example, in a case where the timing of jumping differs between the audience or in a case where the jump height is small, as illustrated in the right side of FIG. 34, the average value $V_y$ of the y components of the velocities becomes small in amplitude. As a result, the final blending ratio α settles to around 0.5, and the avatar's motion does not largely switch between performer 1 and performer 2, thus coming into a calm state.

6-7. Example 4 of Blending Ratio Determination Method

Figure 37:
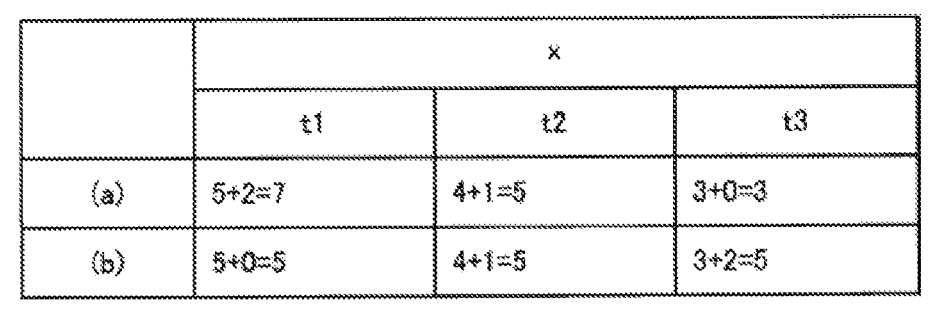

Also in example 4 of the blending ratio determination method described below, the blending ratio may be determined in accordance with motion synchronousness between the audience who enjoy the performance of the performers, instead of the performers on the stage. Note that in this method, the motion of a performer on a real space and an animation (Special Dance Animation) prepared in advance in which a human character or the like makes a motion are blended, instead of blending the motions of sites of two performers. Details of such example 4 of the blending ratio determination method will be described with reference to FIGS. 35 to 38. FIGS. 35, 36, and 38 are image diagrams that describe an operation of example 4 of the blending ratio determination method according to the present embodiment. Further, FIG. 37 is a table that describes the operation of example 4 of the blending ratio determination method according to the present embodiment.

For example, in this method, movements of glow sticks (an instrument that emits a fluorescent color by a chemical reaction) held by all the audience are captured with an imaging unit installed in the venue. Note that in this method, the avatar's motion gradually approaches Special Dance Animation when the movements of the glow sticks held by the audience become synchronous throughout the venue. On the other hand, in this method, the avatar's motion gradually approaches the motion of the performer on the real space when the movements of the glow sticks become out of synchronousness in the entire venue or the movements of the glow sticks themselves become small.

Specifically, in this method, in a case where a point P having a brightness equal to or greater than a predetermined threshold value is detected at each pixel of the imaging unit, an x coordinate position of the point P, i.e., an X coordinate of the pixel is obtained in accordance with the following equation (12). Note that in the following description, as illustrated in the upper right in FIGS. 35 and 36, the imaging unit is assumed to include pixels provided in an 8×4 matrix.

[Math. 11]

$$X = px \tag{12}$$

px: x coordinate of point P

More specifically, in the example of FIG. 35, assume that both of glow sticks 500a and 500b held by audience members 1 and 2 move from right to left, and the movements of the glow slicks 500a and 500b are synchronous. In such a case, in this method, a summation calculation of the X coordinates of the glow sticks 500a and 500b is performed at each of times t1, t2, and t3.

For example, in the example of FIG. 35, at time t1, the X coordinates of the glow sticks 500a and 500b are 5 and 2, and therefore the sum of the X coordinates is 7, as illustrated in the upper part of the table of FIG. 37. Further, in the example of FIG. 35, at time t2, the X coordinates of the glow sticks 500a and 500b are 4 and 1, and therefore the sum of the X coordinates is 5, as illustrated in the upper part of the table of FIG. 37, Further, in the example of FIG. 35, at time t2, the X coordinates of the glow sticks 500a and 500b are 3 and 0, and therefore the sum of the X coordinates is 3, as illustrated in the upper part of the table of FIG. 37.

Then, in this method, a difference between a maximum value X_max and a minimum value X_min of the sums at times t1 to t3 is calculated in accordance with the following equation (13). In this method, the calculated difference is a variable Amp, which is 4 in the example of FIG. 35.

[Math. 12]

$$Amp = X\_\text{max} - X\_\text{min} \tag{13}$$

Further, in the example of FIG. 36, it is assumed that the glow sticks 500a and 500b held by the audience members 1 and 2 move from right to left and from left to right independently of each other, and the movements of the glow sticks 500a and 500b are not synchronous. Also in such a case, a summation calculation of the X coordinates of the glow sticks 500a and 500b is performed at each of times t1, t2, and t3.

For example, in the example of FIG. 36, at time t1, the X coordinates of the glow sticks 500a and 500b are 5 and 0, and therefore the sum of the X coordinates is 5, as illustrated in the lower part of the table of FIG. 37. Further, in the example of FIG. 36, at time t2, the X coordinates of the glow sticks 500a and 500b are 4 and 1, and therefore the sum of the X coordinates is 5, as illustrated in the lower part of the table of FIG. 37. Further, in the example of FIG. 36, at time t2, the X coordinates of the glow sticks 500a and 500b are 3 and 2, and therefore the sum of the X coordinates is 5, as illustrated in the lower part of the table of FIG. 37.

Then, in this method, a difference between the maximum value X_max and the minimum value X_min of the sums at times t1 to t3 is calculated in accordance with the foregoing equation (13). In this method, the calculated difference is a variable Amp, which is 0 in the example of FIG. 36.

Further, in this method, the final blending ratio α is calculated on basis on the calculated variable Amp with reference to the graph illustrated in FIG. 38. Then, in this method, for example, in a case where the variable Amp is a minimum variable Amp_min set in advance, the final blending ratio α is set to 0, and the avatar's motion is caused to approach the performer's motion (real-time motion). On the other hand, in this method, for example, in a case where the variable Amp is a maximum variable Amp_max set in advance, the final blending ratio α is set to 1, and the avatar's motion is caused to approach Special Dance Animation.

In the above description, the final blending ratio α is calculated on the basis of the movements of the glow sticks 500a and 500b from time t1 to time t3; however, in this method, this is non-limiting, and the final blending ratio α may be calculated on the basis of the movements of the glow sticks 500a and 500b for a predetermined past time range, for example, 5 seconds.

6-8. Example 5 of Blending Ratio Determination Method

An algorithm according to a blending ratio determination method in example 5 of the blending ratio determination method dynamically determines the blending ratio α applied to the motion of a site of each of performers in accordance with environmental information around the performer, and blends the motions of the sites of the performers on the basis of the determined blending ratio α. Details of such example 5 of the blending ratio determination method will be described with reference to FIG. 39. FIG. 39 is an image diagram that describes an operation of example 5 of the blending ratio determination method according to the present embodiment.

In this method, for example, as illustrated in FIG. 39, vibrations v of the entire floor on which the audience enjoying the performance of the performers stand may be detected as the environmental information, and the final blending ratio α may be determined in accordance with the vibrations v.

In this method, the algorithm of the final blending ratio α may be set in advance to vary in accordance with music (rhythm, frequency, volume, etc.), and the final blending ratio α may be dynamically changed in synchronization with the music played back during the performance of the performers. Further, in this method, the synchronization may be with the cheer sound in the venue, instead of the music.

Note that the environmental information in this method may include information regarding the sound, light, temperature, humidity, and the like around the performers.

In this method, the final blending ratio α may be dynamically changed by an operation of an operator.

6-9. Example 6 of Blending Ratio Determination Method

An algorithm according to a blending ratio determination method in example 6 of the blending ratio determination method described below dynamically determines the blending ratio α applied to the motion of a site of each of performers in accordance with biological information of the performer on the real space, and blends the motions of the sites of the performers on the basis of the determined blending ratio α. Details of such example 6 of the blending ratio determination method will be described with reference to FIG. 40. FIG. 40 is an image diagram that describes an operation of example 6 of the blending ratio determination method according to the present embodiment.

Specifically, in this method, an algorithm of the final blending ratio α is set in advance to vary in accordance with music (rhythm, frequency, volume, etc.). For example, the final blend ratio α is set to vary as indicated by the solid line in FIG. 40. Furthermore, in this method, the blood alcohol concentration, which is biological information, of the audience is superimposed as Perlin noise (dotted line in FIG. 40) on the preset variations. In this method, this causes the avatar's motions to also sway with drunkenness of the audience.

Note that in the above description, the blood alcohol concentration of the audience is used as the biological information; however, in this method, this is non-limiting and other biological information of the performers or the audience may be used. In this method, while there is no specific limitation, it is possible to obtain the biological information by having the performers or the audience to wear various biological information sensors listed below on their body parts. For example, the foregoing biological information sensors may be biological information sensors such as myoelectric sensors, heart rate sensors, pulse sensors (blood flow sensors (including blood pressure sensors)), blood alcohol concentration sensors, respiration sensors, brain wave sensors, skin temperature sensors, skin conductivity sensors, or perspiration sensors, for example.

Further, in this method, the noise to be superimposed on the preset variations is not particularly limited, and may be, for example, a random number or the like to which a fractal property is added.

6-10. UI Example 1

As described above, in the present embodiment, the final blending ratio α may be dynamically changed by the operation of the operator. Accordingly, m the following, various examples of a user interface (UI) (a predetermined setting screen) for dynamically changing the final blending ratio α will be described. Note that the present embodiment is not limited to the UI examples described below.

First, UI example 1 to dynamically change the blending ratio α applied to the motions of sites of two performers will be described with reference to FIGS. 41 and 42. FIGS. 41 and 42 are image diagrams that describe UI example 1 according to the present embodiment.

For example, in this UI example, a screen 800 as illustrated in FIG. 41 is displayed on a display unit superimposed on a touch panel of a smartphone or tablet or the like held by the operator. On the screen 800, the sites (a first site and a second site) of performers 1 and 2 (a first actor and a second actor) that may be blended are indicated with markers 802. In this UI example, the operator is able to change the final blending ratio α by performing an operation of connecting the sites of performers 1 and 2 to be blended to create a line segment and moving a cursor 804 on the line segment.

Note that in this UI example, moving the cursor 804 may change the color or size of the markers 802, or may change the color or size of the markers 802 connected by the operator, which are non-limiting. In addition, this UT example is not necessarily limited to blending motions of the same sites of performers 1 and 2, and motions of different sites may be blended.

Further, in this UI example, a plurality of sites may be grouped as illustrated in FIG. 42, and in such a case, the motions of a plurality of sites grouped in performer 1 and the motions of a plurality of sites grouped in performer 2 are blended. In tins case, for example, a screen 810 as illustrated in FIG. 42 is displayed on the display unit in this UI example. On the screen 810, markers 802*b*, 802*f*, and 802*e* indicating respective sites of performer 1 are grouped by being connected by broken lines. Further, on the screen 810, markers 802*a*, 802*c*, and 802*d* indicating respective sites of performer 2 are grouped by being connected by broken lines.

6-11. UI Example 2

Next, UI example 2 to dynamically change the blending ratio α applied to the motions of sites of three performers will be described with reference to FIG. 43. FIG. 43 is an image diagram that describes UI example 2 according to the present embodiment.

For example, in this UI example, a screen 820 as illustrated in FIG. 43 is displayed on the foregoing display unit. On the screen 820, the sites of performers 1, 2, and 3 that may be blended are indicated with markers 822, and the operator is able to specify which sites are to be blended by changing the color of the markers.

Further, on the screen 820, it is possible to change the final blending ratio α by performing an operation of moving a cursor 824 in a triangle connecting performers 1, 2, and 3. More specifically, the vertexes of the triangle are associated with respective performers 1, 2, and 3, and the distances from the respective vertexes to the cursor 824 are $r_1$, $r_2$, and $r_3$. Then, in this UI example, the final blending ratios $\alpha 1$, $\alpha 2$, and $\alpha 3$ for the motions of performers 1, 2, and 3 are calculated in accordance with the following expressions (14).

[Math. 13]

$$\alpha_1 \propto (r_2+r_3)/(r_1+r_2+r_3)$$

$$\alpha_2 \propto (r_1+r_3)/(r_1+r_2+r_3)$$

$$\alpha_3 \propto (r_1+r_2)/(r_1+r_2+r_3) \qquad (14)$$

6-12. UI Example 3

Further, UI example 3 to dynamically change the blending ratio α applied to the motions of sites of a plurality of performers will be described with reference to FIG. 44. FIG. 44 is an image diagram that describes UI example 3 according to the present embodiment.

For example, in this UI example, a screen 830 as illustrated in FIG. 44 is displayed on the foregoing display unit. On the screen 830, the sites of the plurality of performers that may be blended are indicated with markers 832, and the operator is able to specify which sites are to be blended by changing the color of the markers.

Further, on the screen 830, it is possible to change the final blending ratio α by performing an operation of moving a cursor 834 inside a polygon connecting the plurality of performers 1, 2, and 3. More specifically, the vertexes of the polygon are associated with respective performers, and the distance from each vertex to the cursor 834 is $r_n$. Then, in this UI example, the final blending ratios $\alpha_n$ for the motions of the performers are calculated in accordance with the following expression (15).

[Math. 14]

$$a_n \propto (r_1+r_2+ \ldots +r_{n-1}+r_{n+1}+ \ldots +r_N)/(r_1+ \ldots +r_N) \qquad (15)$$

As described above, according to the present embodiment, it is possible to blend motions of a plurality of users captured by using a motion capture technique, and to reproduce the blended motions in real time in an avatar or the like on a virtual space.

7. Hardware Configuration Example

The embodiments of the present disclosure have been described above. Finally, with reference to FIG. 45, a description will be given of a hardware configuration of an information processor according to an embodiment of the present disclosure. FIG. 45 is a block diagram illustrating an example of the hardware configuration of the information processor according to the embodiment of the present disclosure. It is to be noted that the information processor 900 illustrated in FIG. 45 is able to implement, for example, the sensor unit 10, the hub unit 20, and the information processor 30 illustrated in FIG. 14. Information processing by the sensor unit 10, the hub unit 20, and the information processor 30 according to the embodiment of the present disclosure is implemented by cooperation of software and hardware described below.

As illustrated in FIG. 45, the information processor 900 includes a CPU (Central Processing Unit) 901, a ROM (Read Only Memory) 902, a RAM (Random Access Memory) 903, and a host bus 904*a*. Further, the information processor 900 includes a bridge 904, an external bus 904*b*, an interface 905, an input unit 906, an output unit 907, a storage unit 908, a drive 909, a connection port 911, a communication unit 913, and a sensor 915. The information processor 900 may include a processing circuit such a DSP or an ASIC in place of or in conjunction with the CPU 901.

The CPU 901 functions as an arithmetic processing unit and a control unit, and controls overall operations in the information processor 900 in accordance with various programs. Further, the CPU 901 may be a microprocessor. The ROM 902 stores programs, arithmetic parameters, etc. that the CPU 901 uses. The RAM 903 temporarily stores a program that is used in execution of the CPU 901, parameters that change appropriately in execution thereof, and the like. The CPU 901 may form, for example, the controller 16, the controller 24, and the controller 34.

The CPU 901, the ROM 902, and the RAM 903 are connected to each other by the host bus 904*a* including a CPU bus and the like. The host bus 904*a* is connected to the external bus 904*b* such as a PCI (Peripheral Component Interconnect/Interface) bus via, the bridge 904. Note that the host bus 904*a*, the bridge 904, and the external bus 904*b* are not necessarily configured separately, and these functions may be packaged in a single bus.

The input unit 906 is implemented by, for example, a unit through which the user inputs information, such as a mouse, a keyboard, a touch panel, a button, a microphone, a switch, and a lever. Further, the input unit 906 may be a remote-control unit that uses infrared ray or other electromagnetic waves, or may be external connection equipment such as a mobile phone or a PDA compatible with operations of the information processor 900. Further, the input unit 906 may include, for example, an input control circuit or the like that generates an input signal on the basis of information inputted by the user using the input means described above and outputs the generated input signal to the CPU 901. It is possible for the user of the information processor 900 to input various data or provide instructions for a processing operation to the information processor 900 by operating the input unit 906.

The output unit 907 is formed by a unit that is able to notify the user of acquired information visually or audibly. Examples of such a unit include displays such as a CRT display, a liquid crystal display, a plasma display, an EL display and a lamp, sound output units such as a speaker and a headphone, printer units, etc. The output unit 907 outputs, for example, results obtained through various processes performed by the information processor 900. Specifically, the display visually displays the results obtained through various processes performed by the information processor 900 in a variety of formats, such as text, images, tables, graphs, etc. Meanwhile, the sound output unit converts audio signals including reproduced sound data, acoustic data or the like into analog signals and outputs the analog signals audibly.

The storage unit 908 is a data storing unit formed as an example of a memory section of the information processor 900. The storage unit 908 is implemented by, for example, a magnetic memory section device such as an HDD, a semiconductor memory device, an optical memory device, a magneto-optical memory device or the like. The storage unit 908 may include a storage medium, a recording unit for recording data on the storage medium, a reading unit for reading data from the storage medium, a deletion unit for deleting data recorded on the storage medium, etc. The storage unit 908 stores a program to be executed by the CPU 901, various data, and various externally acquired data, etc.

The drive 909 is a reader/writer for a storage medium, and is incorporated in or externally attached to the information processor 900. The drive 909 reads information recorded on a removable storage medium mounted thereon, such as a magnetic disk, an optical disk, a magneto-optical disk, or a semiconductor memory, and outputs the information to the RAM 903. The drive 909 is also able to write information on the removable storage medium.

The connection port 911 is an interface to be connected to external equipment, and is a connector to the external equipment that is able to transmit data through, for example, a USB (Universal Serial Bus) or the like.

The communication unit 913 is, for example, a communication interface formed by a communication device or the like for connection to a network 920. The communication unit 913 may be, for example, a communication card or the like for wired or wireless LAN (Local Area Network), LTE (Long Term Evolution), Bluetooth (registered trademark), or WUSB (Wireless USB). Further, the communication unit 913 may be a router for optical communication, a router for ADSL (Asymmetric Digital Subscriber Line), modems for various types of communications, or the like. The communication unit 913 is able to transmit and receive signals or the like to and from the Internet or other communication equipment in accordance with predetermined protocols such as TCP/IP, for example. The communication unit 913 may form, for example, the communicator 18, the communicator 22, and the communicator 32.

The sensor 915 is a sensor of any type such as an acceleration sensor, a gyro sensor, a geomagnetic sensor, an optical sensor, a sound sensor, a range-finding sensor, or a force sensor, for example. The sensor 915 acquires information about the state of the information processor 900 itself, such as the orientation, moving speed or the like of the information processor 900, and information about a surrounding environment of the information processor 900, such as brightness or noise around the information processor 900. Further, the sensor 915 may include a GPS sensor that receives a GPS signal to measure the latitude, longitude, and altitude of the unit. The sensor 915 may form, for example, the gyro sensor 12 and the acceleration sensor 14.

Note that the network 920 is a wired or wireless transmission path for information transmitted from units connected to the network 920. For example, the network 920 may include a public network such as the Internet, a telephone network or a satellite communication network, various LANs (Local Area Networks) including Ethernet (registered trademark), WAN (Wide Area Network), and the like. Further, the network 920 may include a dedicated line network such as an IP-VPN (Internet Protocol-Virtual Private Network).

An example of a hardware configuration that is able to implement the functions of the information processor 900 according to the embodiment of the present disclosure has been described above. Each of the above-described components may be implemented by using a general-purpose member, or may be implemented by hardware specialized for the function of the component. Accordingly, it is possible to appropriately change the hardware configuration to be used in accordance with the technical level at the time of carrying out the embodiments of the present disclosure.

It is to be noted that it is possible to create a computer program for implementing each of the functions of the information processor 900 according to the embodiments of the present disclosure as described above and to install the computer program in a PC, etc. Further, it is also possible to provide a computer-readable recording medium in which such a computer program is stored. The recording medium is, for example, a magnetic disk, an optical disk, a magneto-optical disk, a flash memory, or the like. In addition, the computer program described above may be distributed via a network, for example, without using a recording medium.

8. Conclusion

As described above, according to an embodiment of the present disclosure, it is possible to obtain, with higher accuracy, position information for the sites of the body to which the motion sensors are attached. Further, according to the embodiments of the present disclosure, it is also possible to obtain position information and orientation information for the sites to which no motion sensors are attached. This makes it possible to obtain skeleton information using a smaller number of motion sensors.

Further, according to an embodiment of the present disclosure, it is possible to blend motions of a plurality of actors captured by using a motion capture technique and to reproduce the blended motions in real time in an avatar or the like on a virtual space.

Preferred embodiments of the present disclosure have been described above in detail with reference to the accompanying drawings; however, the technical scope of the present disclosure is not limited to such examples. It is apparent that those skilled in the art of the present disclosure may conceive various alterations or modifications within the scope of the technical idea described in the claims, and it should be understood that such alterations and modifications are also within the technical scope of the present disclosure.

For example, in the foregoing embodiments, an example in which an inertial sensor is attached to the body as the motion sensor has been mainly described; however, the present technology is not limited to such an example. The motion sensor only has to be a sensor that senses movements of a body, and may be a geomagnetic sensor, a barometric sensor, an image sensor, or the like as described above.

In addition, the steps in the foregoing embodiments may not necessarily be processed on a time-series basis in accordance with the order described herein as the flowchart. For example, the steps in the processes of the foregoing embodiments may be processed in an order different from the order described as the flowchart, or may be processed in parallel.

In addition, the effects described herein are merely illustrative or exemplary, and are non-limiting. That is, the technology according to the present disclosure may achieve other effects that are apparent to those skilled in the art from the description herein, in addition to the effects described above or in place of the effects described above.

It is to be noted that the following configurations are also encompassed by the technical scope of the present disclosure.

(1)

A program that causes a computer to implement a control function of dynamically controlling a motion of an avatar in a virtual space or a robot on a real space, the control function being configured to:

capture motions of a plurality of actors on the real space from respective motion sensors attached to the actors;

blend the motions of the plurality of actors on the basis of a predetermined algorithm; and dynamically control the motion of the avatar or the robot on the basis of a blend result to cause the avatar or the robot to make a motion reflecting the motions of the plurality of actors.

(2)

The program according to (1), in which the control function is configured to:

capture a motion corresponding to at least one site of each of the actors from the motion sensors attached to the each of the actors;

blend the motions of the sites of the plurality of actors on the basis of the predetermined algorithm; and dynamically control the motion of the avatar or the robot on the basis of the blend result.

(3)

The program according to (2), in which the site includes a part of a body of the actor.

(4)

The program according to (3), in which the part of the body includes at least one of upper body, lower body, head, a joint, waist, a wrist, or an ankle.

(5)

The program according to any one of (1) to (4), in winch the actors include at least one person among performers and an audience.

(6)

The program according to (2), in which the predetermined algorithm blends the motions of the plurality of actors on the basis of a weighting that is applied to each of the actors in advance.

(7)

The program according to any one of (1) to (5), in which the predetermined algorithm blends the motions of the plurality of actors on the basis of a weighting that is dynamically applied to each of the actors in accordance with a distance from a reference point set in advance on the real space to the each of the actors.

(8)

The program according to any one of (1) to (5), in which the predetermined algorithm blends the motions of the plurality of actors on the basis of a weighting that is dynamically applied to each of the actors in accordance with an acceleration, a velocity, or a displacement amount of the each of the actors on the real space.

(9)

The program according to any one of (1) to (5), in which the predetermined algorithm blends the motions of the plurality of actors on the basis of a weighting that is dynamically applied to each of the actors in accordance with a degree of movement synchronousness between the actors on the real space.

(10)

The program according to any one of (1) to (5), in which the predetermined algorithm blends the motions of the plurality of actors on the basis of a weighting that is dynamically applied to each of the actors in accordance with biological information of the each of the actors.

(11)

The program according to any one of (1) to (5), in which the predetermined algorithm blends the motions of the plurality of actors on the basis of a weighting that is dynamically applied to each of the actors in accordance with environmental information around the each of the actors.

(12)

The program according to (6), in which the weighting is set in advance by operating a predetermined setting screen by an operator.

(13)

The program according to (12), in which the weighting is set by performing, by the operator, an operation of moving a cursor on a line segment connecting a first site of a first one of the actors and a second site of a second one of the actors on the setting screen.

(14)

The program according to (12), in which the weighting is set by performing, by the operator, an operation of moving a cursor in a polygon that connects respective predetermined sites of the actors to each other.

(15)

The program according to (2), causing the computer to implement a correction function of, when capturing the motion of each of the actors, referencing a first output obtained by performing a first process on sensor data acquired by two or more of the motion sensors attached to two or more of the sites of each of the actors and a second output obtained by performing a second process on the sensor data, and correcting position information for the sites to which the motion sensors are attached.

(16)

An information processor including a controller that dynamically controls a motion of an avatar in a virtual space or a robot on a real space, the controller being configured to:

capture motions of a plurality of actors on the real space from respective motion sensors attached to the actors;

blend the motions of the plurality of actors on the basis of a predetermined algorithm; and dynamically control the motion of the avatar or the robot on the basis of a blend result to cause the avatar or the robot to make a motion reflecting the motions of the plurality of actors.

(17)

An information processing method including:

capturing motions of a plurality of actors on a real space from respective motion sensors attached to the actors;

blending the motions of the plurality of actors on the basis of a predetermined algorithm: and dynamically controlling a motion of an avatar in a virtual space or a robot on the real space on the basis of a blend result to cause the avatar or the robot to make a motion reflecting the motions of the plurality of actors.

REFERENCE SIGNS LIST

10, 10A, 10B, 10C, 10D, 10E, 10F: Sensor unit
12: Gyro sensor
14: Acceleration sensor
16: Controller
18, 32: Communicator
20: Hub unit
22: Communicator
24, 34: Controller
30: Information processor
40: Output unit
500a, 500b: Glow stick
510: Global motion acceleration orientation calculator
520: Integral calculator
530: Selector
540, 541, 544: Attachment position regression estimator
550: Reliability identifier
560: Ground contact detector
570, 572, 573, 574: Corrector
580, 583: Interpolator
610: Information acquirer
620: Blending ratio determinator
630: Blender
640: Operation controller
800, 810, 820, 830: Screen
802, 822, 832: Marker
804, 824, 834: Cursor
900: Information processor
901: CPU
902: ROM
903: RAM
904: Bridge
904a: Host bus
904b: External bus
905: Interface
906: Input unit
908: Storage unit
909: Drive
911: Connection port
913: Communication unit
915: Sensor
920: Network

The invention claimed is:

1. A non-transitory computer-readable medium having embodied thereon a program, which when executed by a computer causes the computer to execute an information processing method, the method comprising:

capturing motions of a plurality of actors on a real space from respective motion sensors attached to the plurality of actors, each motion sensor being attached to a same site of each actor of the plurality of actors;

blending the motions of the plurality of actors on a basis of a predetermined algorithm; and dynamically controlling a motion of an avatar in a virtual space or a robot on a basis of a result of the blending to cause the avatar or the robot to make a motion reflecting the motions of the plurality of actors, wherein the predetermined algorithm blends the motions of the plurality of actors on a basis of a weighting that is applied to the same site of each actor of the plurality of actors and combining the weighted sites of the each actor of the plurality of actors with each other, and wherein the weighting is set in advance by operating a predetermined setting screen by an operator.

2. The non-transitory computer-readable medium according to claim 1, wherein the method further comprises:

capturing a motion corresponding to at least one site of each actor of the plurality of actors from the motion sensors attached to the each actor of the plurality of actors;

blending the motions of the sites of the plurality of actors on the basis of the predetermined algorithm; and dynamically controlling the motion of the avatar or the robot on the basis of the result of the blending.

3. The non-transitory computer-readable medium according to claim 2, wherein the site comprises a part of a body of the actor.

4. The non-transitory computer-readable medium according to claim 3, wherein the part of the body includes at least one of upper body, lower body, head, a joint, waist, a wrist, or an ankle.

5. The non-transitory computer-readable medium according to claim 2, wherein the method further comprises:

when capturing the motion of each actor of the plurality of actors, referencing a first output obtained by performing a first process on sensor data acquired by two or more of the motion sensors attached to two or more of the sites of each actor of the plurality of actors and a second output obtained by performing a second process on the sensor data, and correcting position information for the sites to which the motion sensors are attached.

6. The non-transitory computer-readable medium according to claim 1, wherein the plurality of actors include at least one person among performers and an audience.

7. The non-transitory computer-readable medium according to claim 1, wherein the predetermined algorithm blends the motions of the plurality of actors on the basis of the weighting that is dynamically applied to each actor of the plurality of actors in accordance with a distance from a reference point set in advance on the real space to the each actor of the plurality of actors.

8. The non-transitory computer-readable medium according to claim 1, wherein the predetermined algorithm blends the motions of the plurality of actors on the basis of the weighting that is dynamically applied to each actor of the plurality of actors in accordance with an acceleration, a velocity, or a displacement amount of the each actor of the plurality of actors on the real space.

9. The non-transitory computer-readable medium according to claim 1, wherein the predetermined algorithm blends the motions of the plurality of actors on the basis of the weighting that is dynamically applied to each actor of the plurality of actors in accordance with a degree of movement synchronousness between the plurality of actors on the real space.

10. The non-transitory computer-readable medium according to claim 1, wherein the predetermined algorithm blends the motions of the plurality of actors on the basis of the weighting that is dynamically applied to each actor of the plurality of actors in accordance with biological information of the each actor of the plurality of actors.

11. The non-transitory computer-readable medium according to claim 1, wherein the predetermined algorithm blends the motions of the plurality of actors on the basis of the weighting that is dynamically applied to each actor of the plurality of actors in accordance with environmental information around the each actor of the plurality of actors.

12. The non-transitory computer-readable medium according to claim 1, wherein the weighting is set by performing, by the operator, an operation of moving a cursor on a line segment connecting a first site of a first actor of the plurality of actors and a second site of a second actor of the plurality of actors on the setting screen.

13. The non-transitory computer-readable medium according to claim 1, wherein the weighting is set by performing, by the operator, an operation of moving a cursor in a polygon that connects respective predetermined sites of the plurality of actors to each other.

14. An information processor comprising
a controller that dynamically controls a motion of an avatar in a virtual space or a robot on a real space, the controller being configured to:
capture motions of a plurality of actors on the real space from respective motion sensors attached to the plurality of actors, each motion sensor being attached to a same site of each actor of the plurality of actors;
blend the motions of the plurality of actors on a basis of a predetermined algorithm; and
dynamically control the motion of the avatar or the robot on a basis of a result of the blending to cause the avatar or the robot to make a motion reflecting the motions of the plurality of actors,
wherein the predetermined algorithm blends the motions of the plurality of actors on a basis of a weighting that is applied to the same site of each actor of the plurality of actors and combining the weighted sites of the each actor of the plurality of actors with each other, and
wherein the weighting is set in advance by operating a predetermined setting screen by an operator.

15. An information processing method comprising:
capturing motions of a plurality of actors on a real space from respective motion sensors attached to the plurality of actors, each motion sensor being attached to a same site of each actor of the plurality of actors;
blending the motions of the plurality of actors on a basis of a predetermined algorithm; and
dynamically controlling a motion of an avatar in a virtual space or a robot on the real space on a basis of a result of the blending to cause the avatar or the robot to make a motion reflecting the motions of the plurality of actors,
wherein the predetermined algorithm blends the motions of the plurality of actors on a basis of a weighting that is applied to the same site of each actor of the plurality of actors and combining the weighted sites of the each actor of the plurality of actors with each other, and
wherein the weighting is set in advance by operating a predetermined setting screen by an operator.

* * * * *